(12) United States Patent
Nishimura et al.

(10) Patent No.: US 9,644,010 B2
(45) Date of Patent: May 9, 2017

(54) LY6K EPITOPE PEPTIDES FOR TH1 CELLS AND VACCINES CONTAINING THE SAME

(71) Applicant: ONCOTHERAPY SCIENCE, INC., Kanagawa (JP)

(72) Inventors: Yasuharu Nishimura, Kumamoto (JP); Yusuke Tomita, Kumamoto (JP); Ryuji Osawa, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 4 days.

(21) Appl. No.: 14/413,416

(22) PCT Filed: Jul. 9, 2013

(86) PCT No.: PCT/JP2013/004249
§ 371 (c)(1),
(2) Date: Jan. 7, 2015

(87) PCT Pub. No.: WO2014/010232
PCT Pub. Date: Jan. 16, 2014

(65) Prior Publication Data
US 2015/0191516 A1 Jul. 9, 2015

Related U.S. Application Data

(60) Provisional application No. 61/669,995, filed on Jul. 10, 2012.

(51) Int. Cl.
| | |
|---|---|
| C07K 14/435 | (2006.01) |
| C12N 5/078 | (2010.01) |
| A61K 38/00 | (2006.01) |
| C07K 14/47 | (2006.01) |
| A61K 39/00 | (2006.01) |
| C07K 16/28 | (2006.01) |
| C07K 16/18 | (2006.01) |

(52) U.S. Cl.
CPC ............ *C07K 14/435* (2013.01); *A61K 38/00* (2013.01); *A61K 39/0011* (2013.01); *C07K 14/4748* (2013.01); *C07K 16/18* (2013.01); *C07K 16/2833* (2013.01); *C12N 5/0634* (2013.01); *A61K 39/00* (2013.01); *A61K 2039/5154* (2013.01); *A61K 2039/55566* (2013.01); *A61K 2039/57* (2013.01); *A61K 2039/70* (2013.01)

(58) Field of Classification Search
None
See application file for complete search history.

(56) References Cited

U.S. PATENT DOCUMENTS

| | | | | |
|---|---|---|---|---|
| 7,847,060 B2 * | 12/2010 | Tahara | ................ | C12N 9/1211 530/300 |
| 8,614,176 B2 * | 12/2013 | Tahara | ................ | C12N 9/1211 514/1.1 |
| 2006/0024692 A1 | 2/2006 | Nakamura et al. | | |
| 2009/0175844 A1 | 7/2009 | Nakamura et al. | | |
| 2009/0202576 A1 | 8/2009 | Tahara et al. | | |
| 2010/0040641 A1 | 2/2010 | Tsunoda et al. | | |
| 2010/0291091 A1 | 11/2010 | Nakamura et al. | | |
| 2011/0027302 A1 * | 2/2011 | Tahara | ................ | C12N 9/1211 424/185.1 |
| 2011/0243973 A1 | 10/2011 | Tsunoda et al. | | |
| 2012/0014996 A1 | 1/2012 | Nakamura et al. | | |
| 2012/0321649 A1 | 12/2012 | Tsunoda et al. | | |
| 2013/0011933 A1 | 1/2013 | Nakamura et al. | | |
| 2013/0189291 A1 | 7/2013 | Tsunoda et al. | | |
| 2014/0141027 A1 | 5/2014 | Tsunoda et al. | | |
| 2014/0248300 A1 | 9/2014 | Tsunoda et al. | | |

FOREIGN PATENT DOCUMENTS

| | | |
|---|---|---|
| WO | 2004/031413 A2 | 4/2004 |
| WO | 2006/085684 A2 | 8/2006 |
| WO | 2006/090810 A2 | 8/2006 |
| WO | 2008/102557 A1 | 8/2008 |
| WO | 2009/016691 A1 | 2/2009 |
| WO | 2010/021112 A1 | 2/2010 |

OTHER PUBLICATIONS

Bowie et al (Science, 1990, 257:1306-1310).*
Rudikoff et al. (PNAS, USA, 1982, 79: 1979-1983).*
Coleman et al. (Research in Immunology, 1994; 145(1): 33-36).*
George et al. (2005, Trends in Immunology 26(12):653-659).*
Burgess et al (J of Cell Bio. 111:2129-2138, 1990).*
Naylor, et al., "Peptide Based Vaccine Approaches for Cancer—A Novel Approach Using a WT-1 Synthetic Long Peptide and the IRX-2 Immunomodulatory Regimen," *Cancers*, vol. 3 (4), pp. 3991-4009 (Oct. 25, 2011).
International Search Report dated Sep. 24, 2013 for International Patent Application PCT/JP2013/004249, 5 pages.

(Continued)

*Primary Examiner* — Peter J Reddig
(74) *Attorney, Agent, or Firm* — Kilpatrick Townsend & Stockton LLP

(57) ABSTRACT

Isolated LY6K-derived epitope peptides having Th1 cell inducibility are disclosed herein. Such peptides can be recognized by MHC class II molecules and induce Th1 cells. In preferred embodiments, such a peptide of the present invention can be promiscuously bind to MHC class II molecules and induce LY6K-specific cytotoxic T lymphocytes (CTLs) in addition to Th1 cells. Such peptides are thus suitable for use in enhancing immune response in a subject, and accordingly find use in cancer immunotherapy, in particular, as cancer vaccines. Also disclosed herein are polynucleotides that encode any of the aforementioned peptides, APCs and Th1 cells induced by such peptides and methods of induction associated therewith. Pharmaceutical compositions that comprise any of the aforementioned components as active ingredients find use in the treatment and/or prevention of cancers or tumors.

8 Claims, 34 Drawing Sheets

(56) References Cited

OTHER PUBLICATIONS

Balsara et al., "Comparative Genomic Hybridization Analysis Detects Frequent, Often High-Levl, Overrepresentation of DNA Sequences at 3q, 5p, 7p, and 8q in Human Non-Small Cell Lung Carcinomas", *Cancer Research*, vol. 57(11), pp. 2116-2120 (1997).
Bamezai et al., "Overexpressed Ly-6A.2 mediates cell-cell adhesion by binding a ligand expressed on lymphoid cells", *Proc Natl Acad Sci USA*, vol. 92(10), pp. 4294-4298 (1995).
Belli et al., "Vaccination of Metastatic Melanoma Patients with Autologous Tumor-Derived Heat Shock Protein gp96-Peptide complexes: Clinical and Immunologic Findings", *J Clin Oncol.*, vol. 20(20), pp. 4169-4180 (2002).
Bevan, "Helping the CD8+ T-Cell Response", *Nat Rev Immunol.*, vol. 4(8), pp. 595-602 (2004).
Boon, "Tumor Antigens Recognized by Cytolytic T Lymphocytes: Present Perspectives for Specific Immunotherapy," *Int J Cancer*, vol. 54(2), pp. 177-180 (1993).
Boon et al., "Human Tumor Antigens Recognized by T Lymphocytes," *J Exp Med.*, vol. 183(3), pp. 725-729 (1996).
Bos et al., "CD4+ T cell help in the tumor milieu is required for recruitment and cytolytic function of CD8+ T lymphocytes", Cancer Res., vol. 70(21), pp. 8368-8377 (2010).
Butterfield et al., "Generation of Human T-cell Responses to an HLA-A2.1-restricted Peptide Epitope Derived from α—Fetoprotein," *Cancer Res.*, vol. 59(13), pp. 3134-3142 (1999).
Chamoto Immunotherapy Cancer Res., et al., "Potentiation of Tumor Eradication by Adoptive Immunotherapy with T-cell Receptor Gene-Transduced T-Helper Type 1 Cells", *Cancer Res.*, vol. 64(1), pp. 386-390 (2004).
Coulie et al., "Cytolytic T-cell Responses of cancer patients vaccinated with a MAGE antigen" *Immunol Rev.*, vol. 188, pp. 33-42 (2002).
De Nooij-Van Dalen et al., "Characterization of the Human LY-6 Antigens, the Newly Annotated Member LY-6K Included, as Molecular Markers for the Head-and-Neck Squamous Cell Carcinoma", Int. J. Cancer, vol. 103(6), pp. 768-774 (2003).
Fujie et al., "A *Mage-1*-Encoded HLA-A24-Binding Synthetic Peptide Induces Specific Anti-tumor Cytotoxic T Lymphocytes", *Int. J. Cancer.*, vol. 80(2), pp. 169-172 (1999).
Harris, "Structure and Function of the p53 Tumor Suppresssor Gene: Clues for Rational Cancer Therapeutic Strategies," *J Natl Cancer Inst.*, vol. 88(20), pp. 1442-1455 (1996).

Iwahashi et al., "Vaccination with peptides derived from cancer-testis antigens in combination with CpG-7909 elicits strong specific CD8+ T cell response in patients with metastatic esophageal squamous cell carcinoma", *Cancer Science*, vol. 101(12), pp. 2510-2517 (2010).
Kikuchi et al., "Identification of a Sart-1-Derived Peptide Capable of Inducing HLA-A24-Restricted and Tumor-Specific Cytotoxic T Lymphocytes", *Int. J Cancer*, vol. 81(3), pp. 459-466 (1999).
Melief et al., "Immunotherapy of established (pre)malignant disease by synthetic long peptide vaccines", *Nat Rev Cancer*, vol. 8(5), pp. 351-360 (2008).
Oiso et al., "A Newly Identified *Mage-3*-Derived Epitope Recognized by HLA-A24-Restricted Cytotoxic T Lymphocytes", *Int J Cancer*, vol. 81(3), pp. 387-394 (1999).
Rosenberg, et al., "Cancer immunotherapy: moving beyond current vaccines", *Nat. Med*, vol. 10(9 ), pp. 909-915 (2004).
Shedlock et al., "Requirement for CD4 Cell Help in Generating Functional CD8 T Cell Memory", *Science*, vol. 300(5617), pp. 337-339 (2003).
Street et al., "Perforin and interferon-γ activities independenctly control tumor initiation, growth, and metastasis" *Blood*, vol. 97(1), pp. 192-197 (2001).
Suda et al., "Identification of human leukocyte antigen-A24-restricted epitope peptides derived from gene products upregulated in lung and esophageal cancers as novel targets for immunotherapy," *Cancer Sci.*, vol. 98(11), pp. 1803-1808 (2007).
Tanaka et al., "Induction of Antitumor Cytotoxic T Lymphocytes with a MAGE-3-encoded Synthetic Peptide Presented by Human Leukocytes Antigen-A24", *Cancer Res.*, vol. 57( 20), pp. 4465-4468 (1997).
Van Der Burg, et al., "Immunogenicity of Peptides Bound to MHC Class I Molecules Depends on the MHC-Peptide Complex Stability," *J. Immunol.*, vol. 156(9), pp. 3308-3314 (1996).
Vissers et al., "The Renal Cell Carcinoma-associated Antigen G250 Encodes a Human Leukocyte Antigen (HLA)-A2.1-restricted Epitope Recognized by Cytotoxic T Lymphocytes", *Cancer Res.*, vol. 59( 21), pp. 5554-5559 (1999).
Wang et al., "A systematic Assessment of MHC Class II Peptide Binding Predictions and Evaluation of a Consensus Approach", *PLos Comput Biol.*, vol. 4(4), e1000048, 10 pages (2008).
U.S. Appl. No. 14/989,741, filed Jan. 6, 2016, 127 pages.
Tomita et al., "Identification of Immunogenic LY6K Long Peptide Encompassing both CD4[+] and CD8[+] T-Cell Epitopes and Eliciting CD4[+] T-Cell Immunity in Patients with Malignant Disease," *OncoImmunology* 3, e28100; Feb. 1-15, 2014.

* cited by examiner

Fig. 1B
B

1. LY6K (119-142): KWTEPYCVIAAVKIFPRFFMVAKQ (SEQ ID NO: 1)

2. LY6K (172-191): KCCKIRYCNLEGPPINSSVF (SEQ ID NO: 2)
   HLA-A24

Fig. 2A
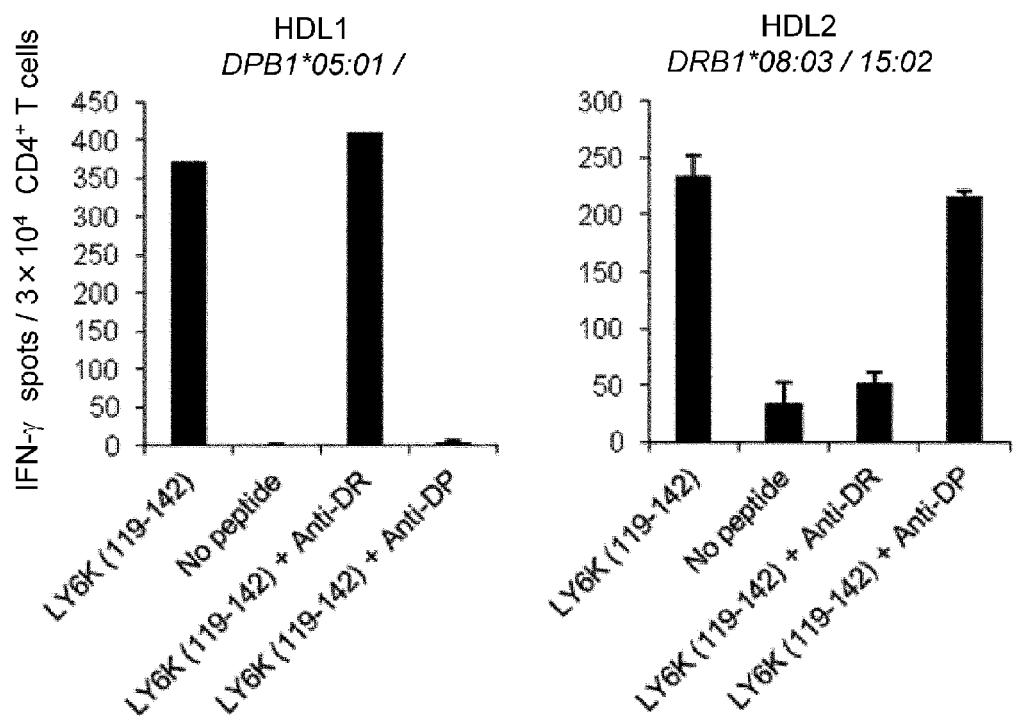
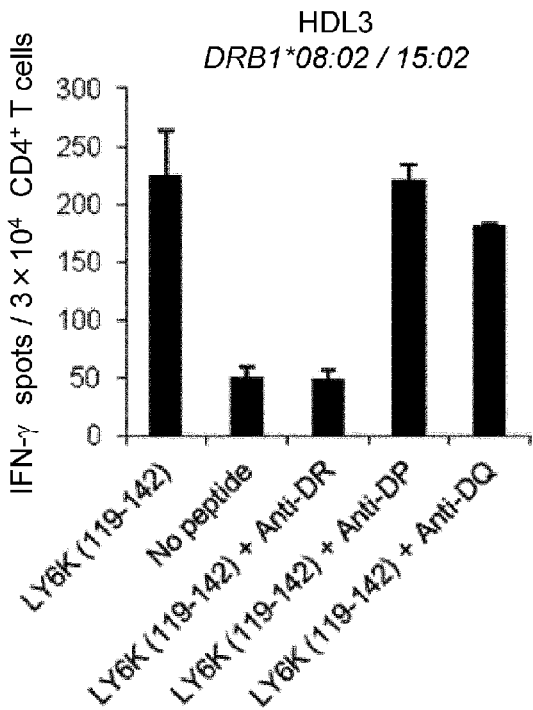

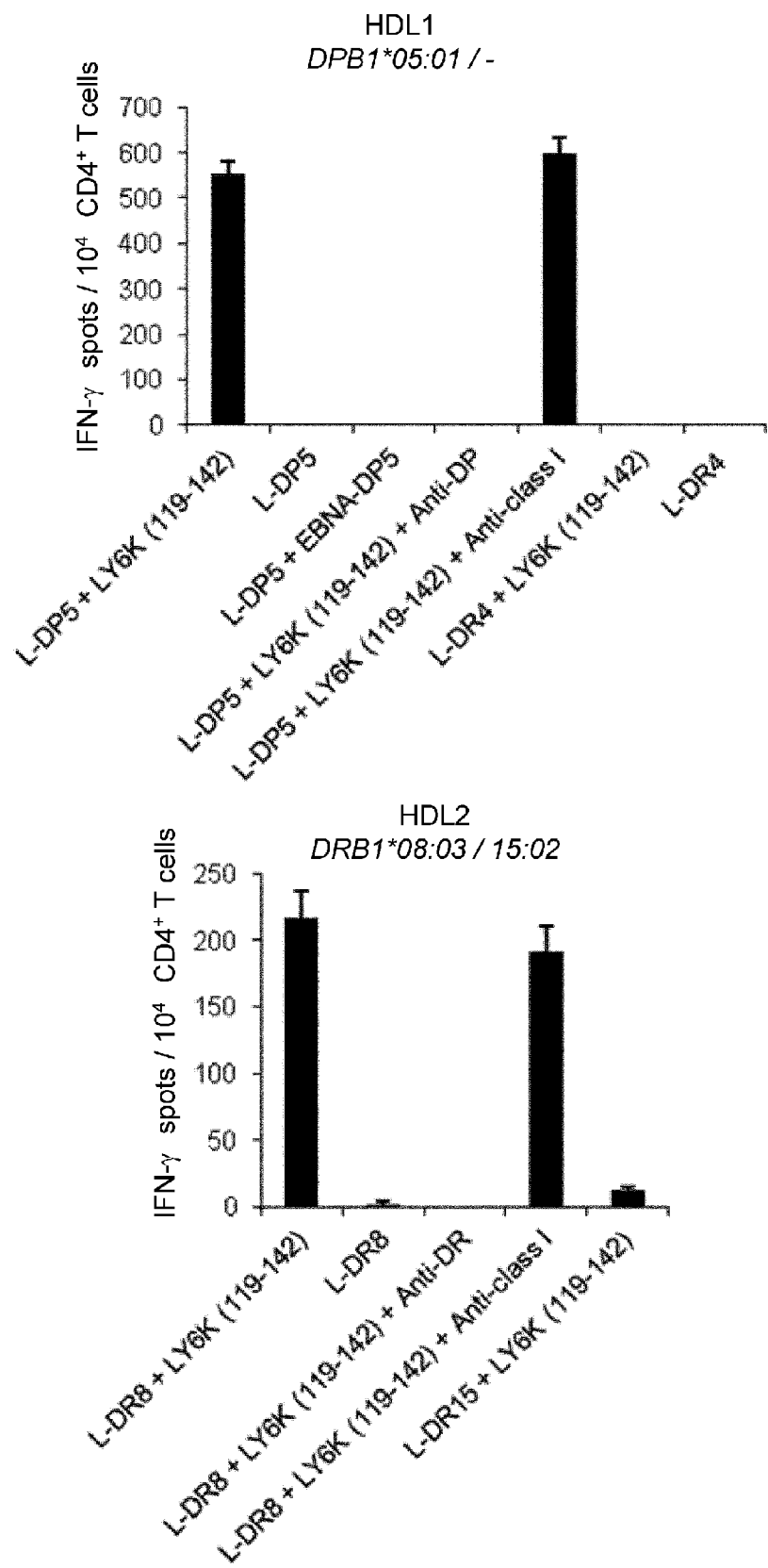

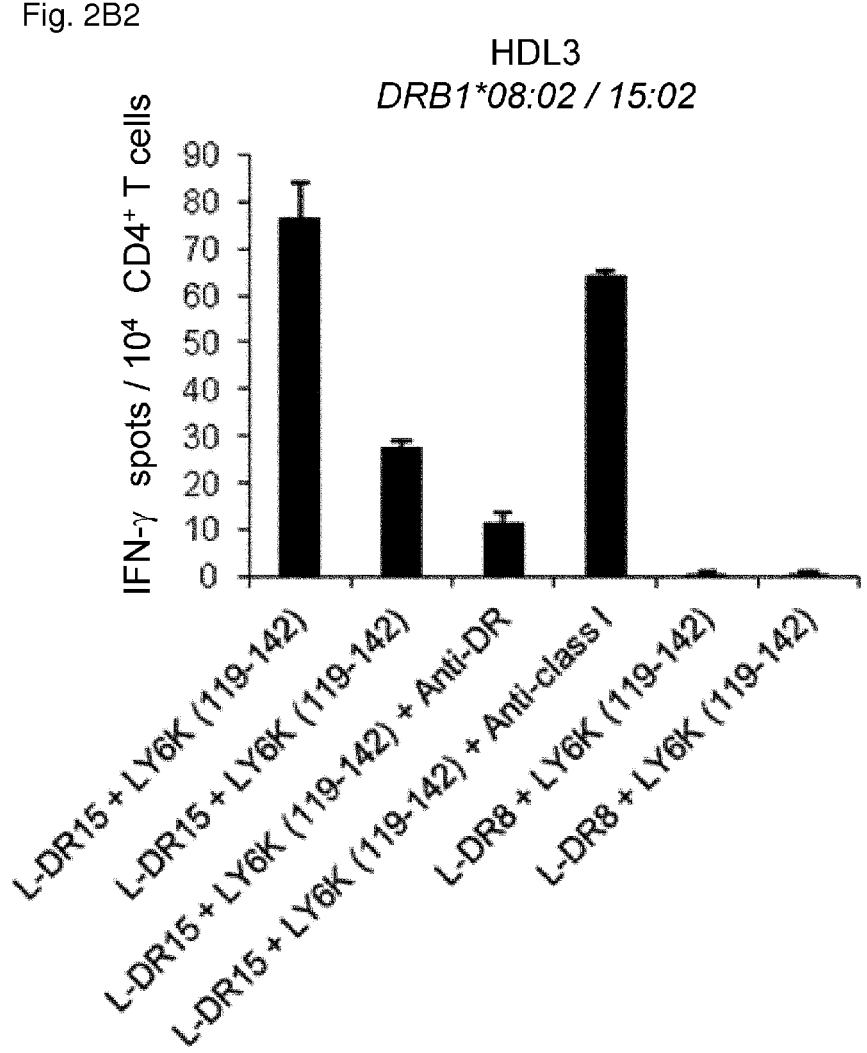
Fig. 2B2

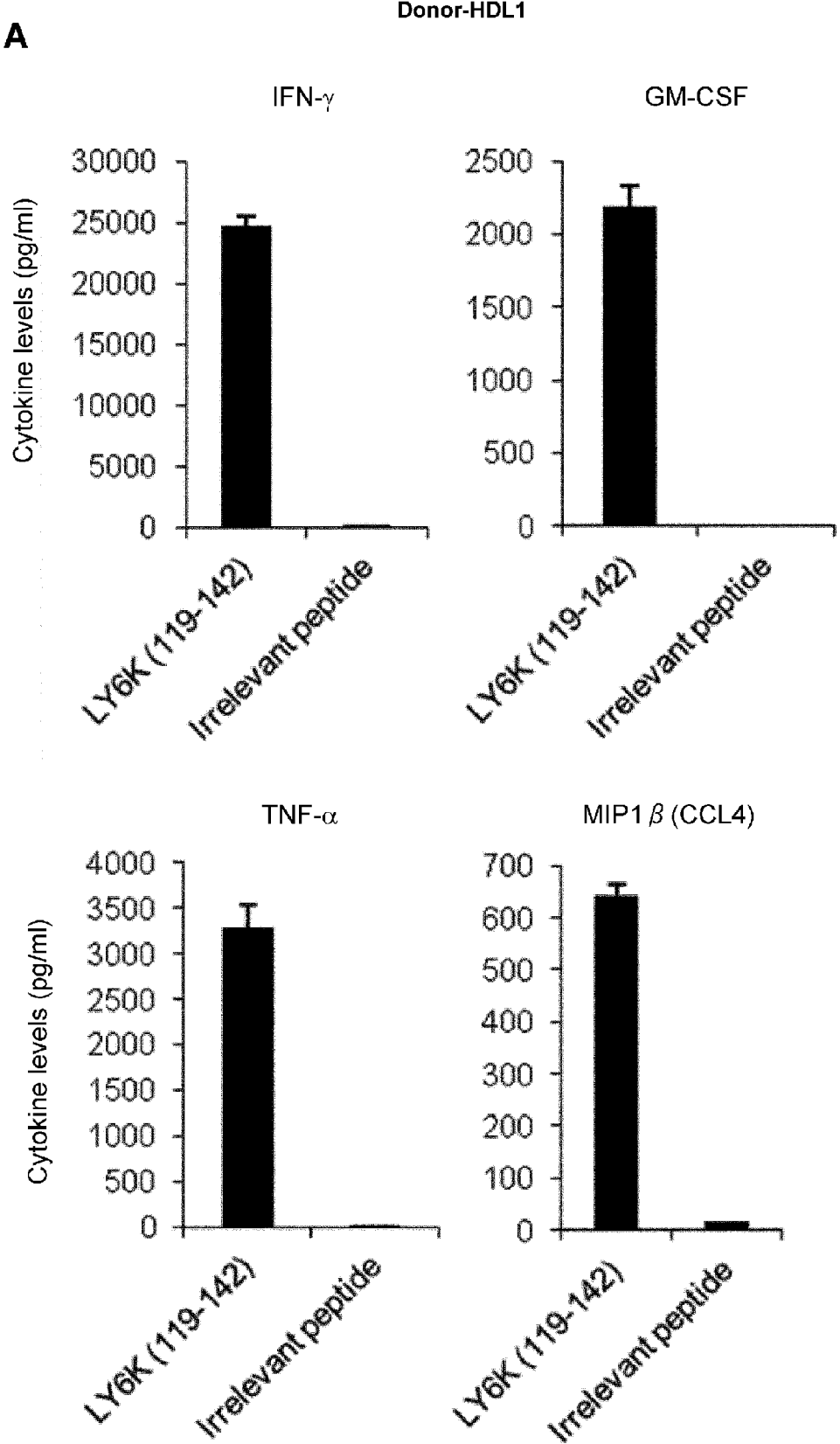
Fig. 5A1

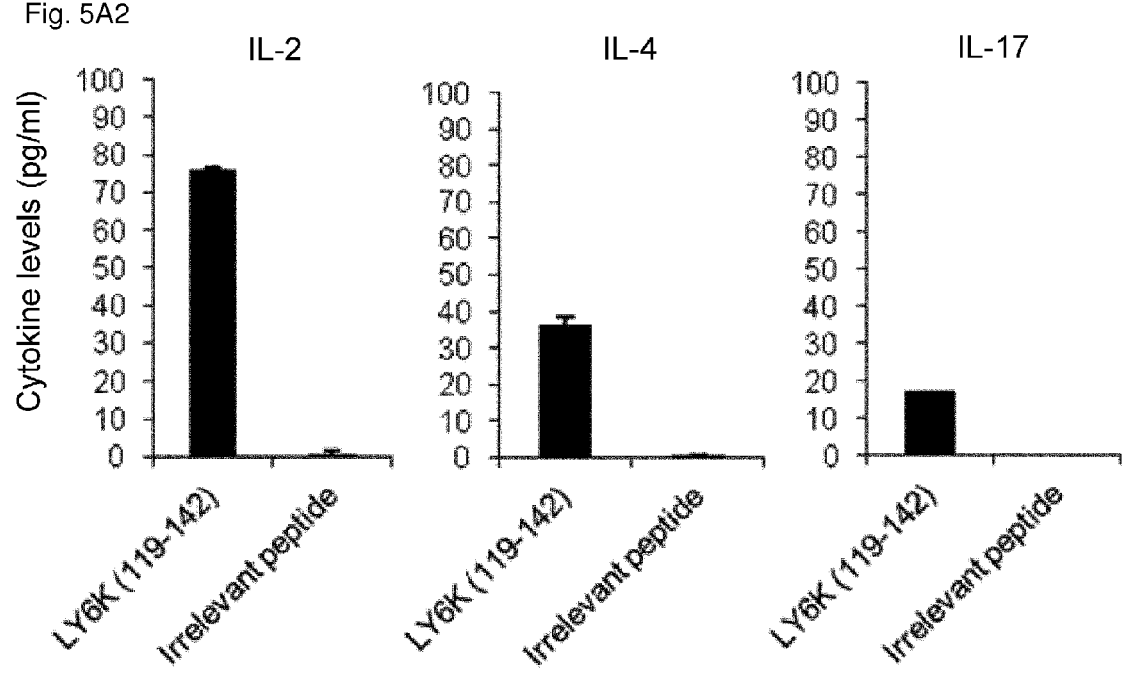
Fig. 5A2

Fig. 5C
Donor-HDL1
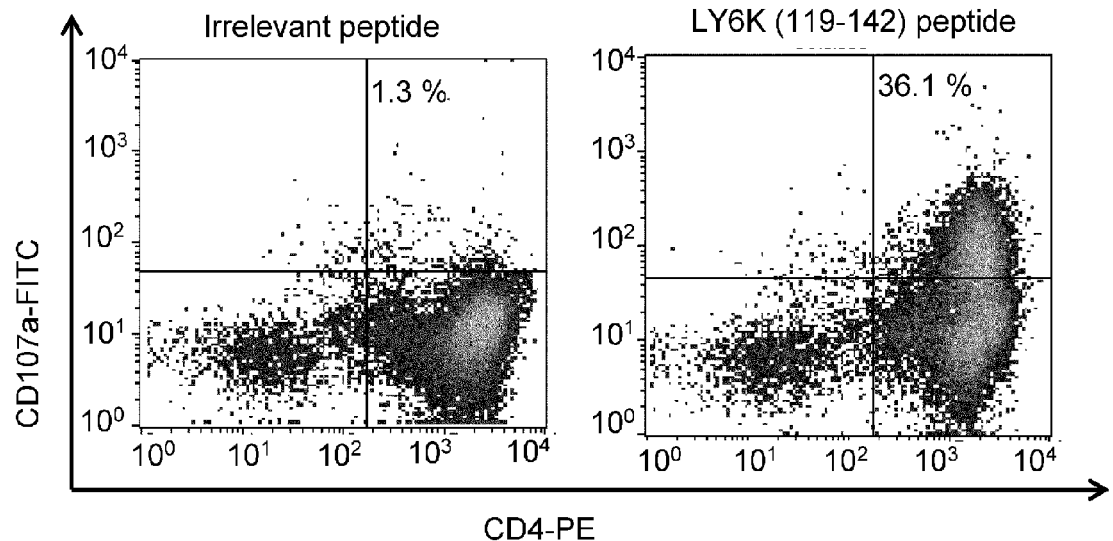
**HDL4: DQB1 *05:03/06:01**
LY6K₁₇₂₋₁₉₁-LP-specific bulk Th cell
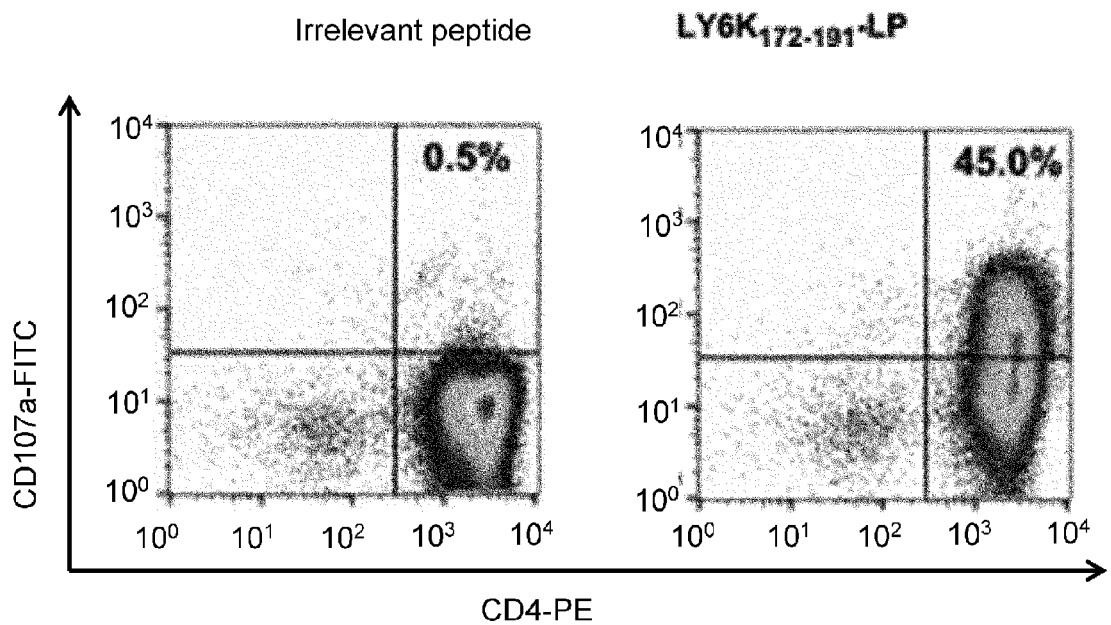

Fig. 6A-B
A
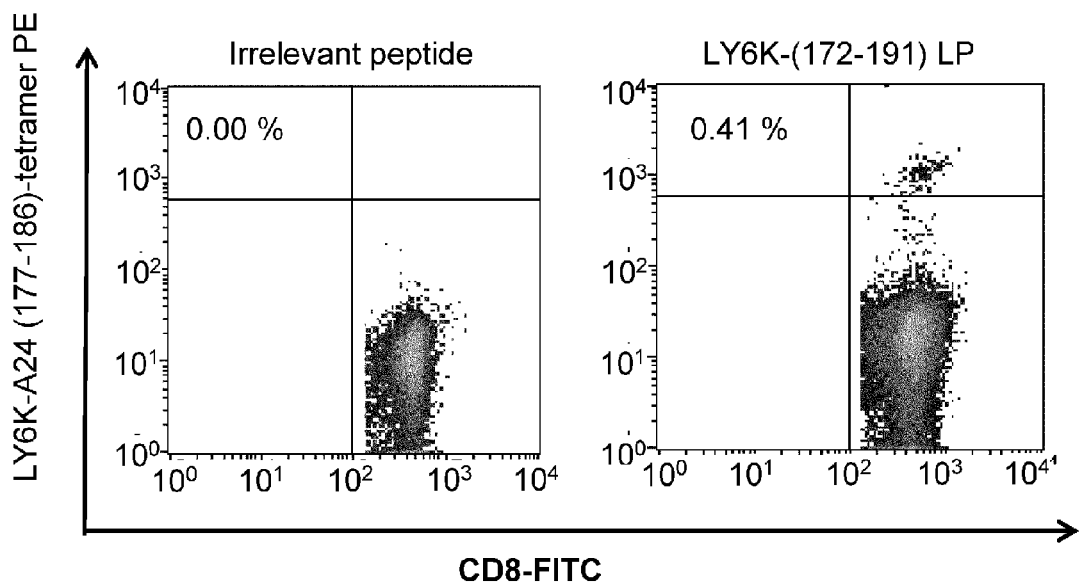
B
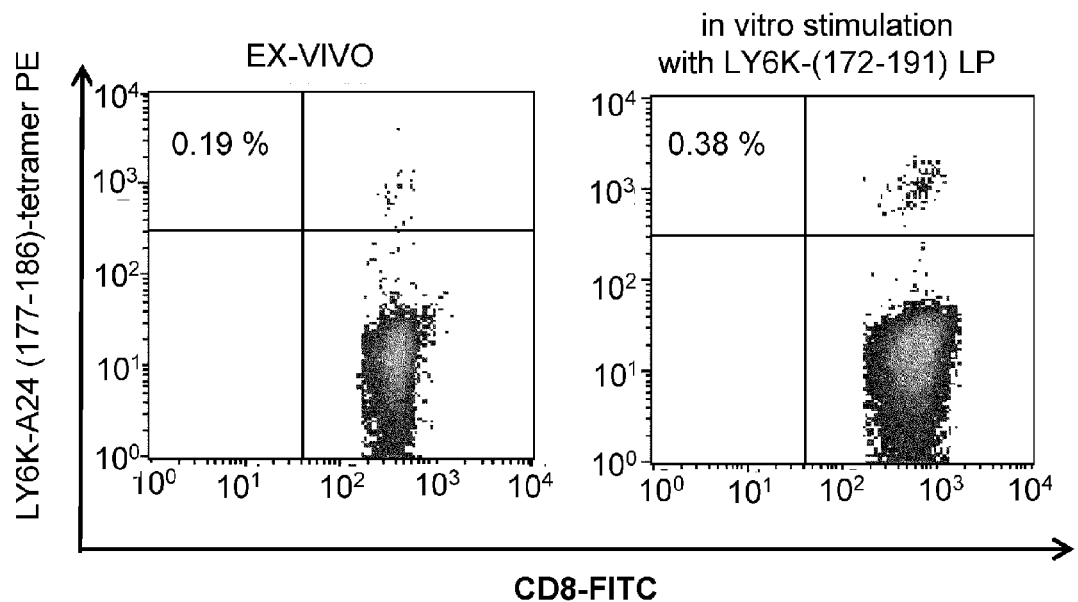

Fig. 7A-B
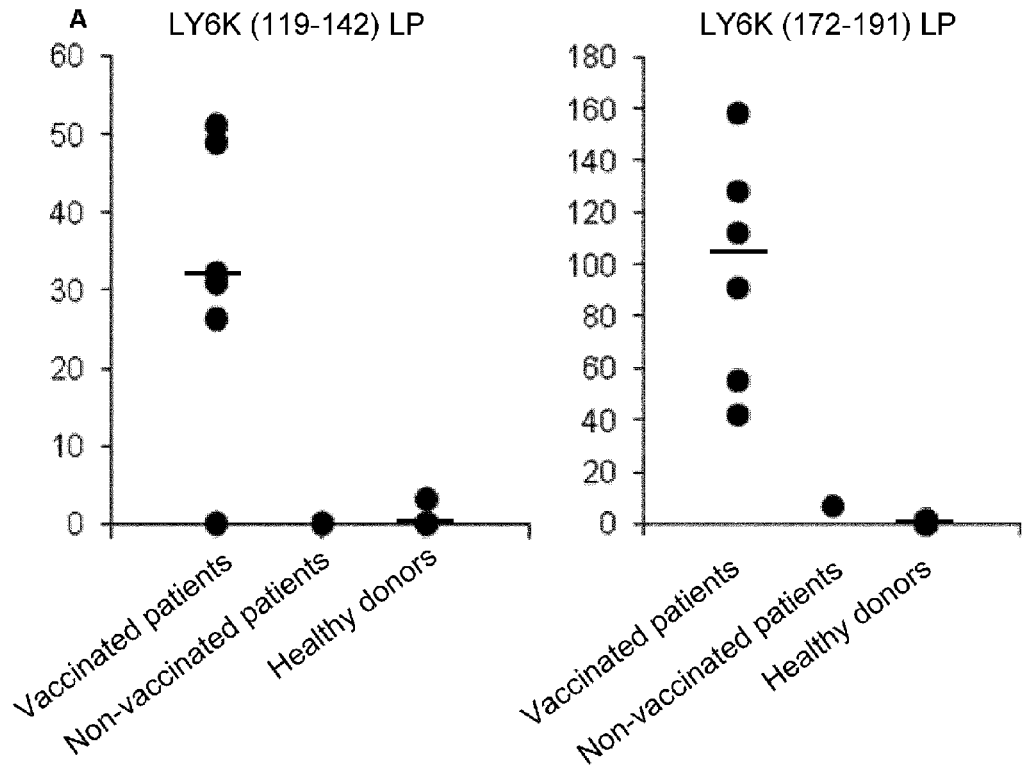
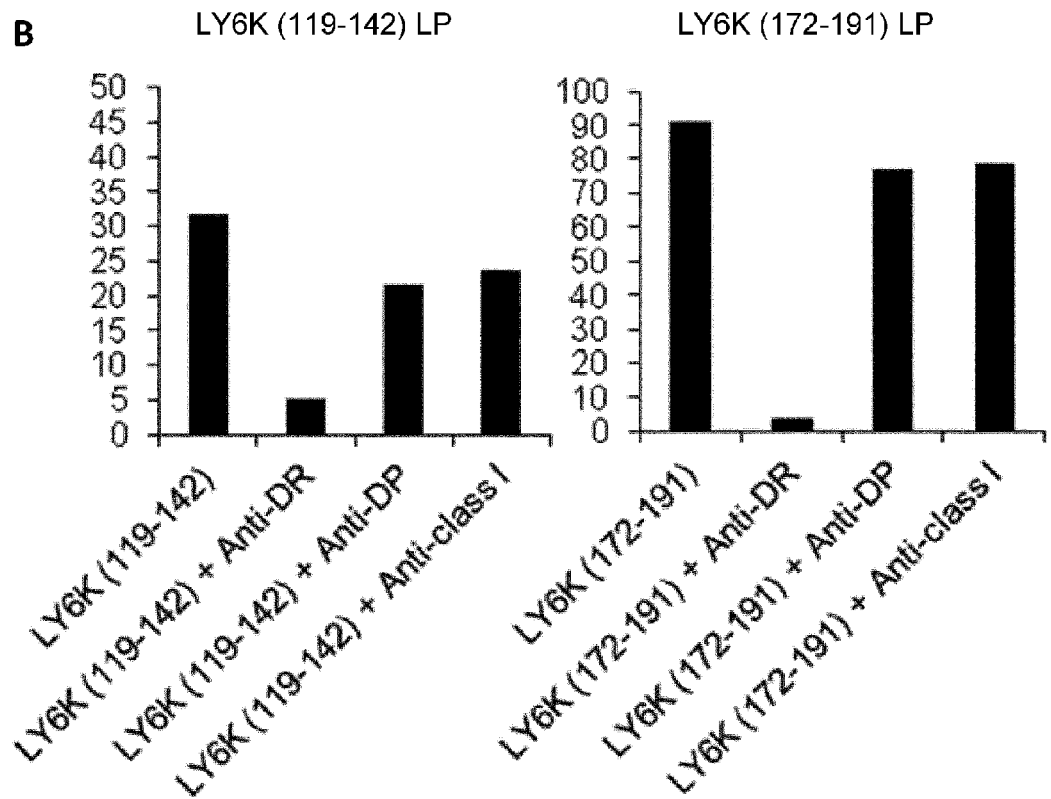

Fig. 8B1
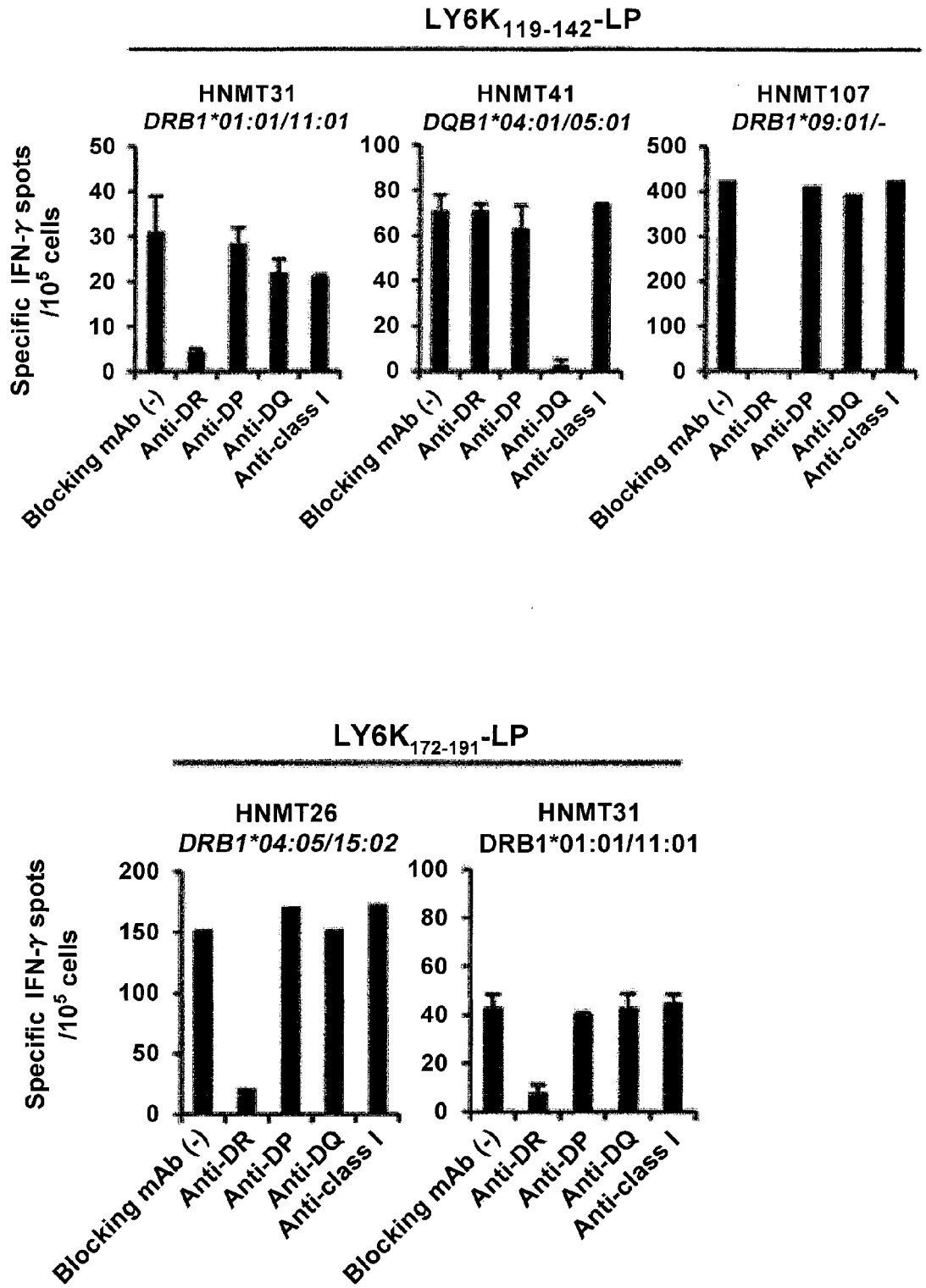

Fig. 8B2
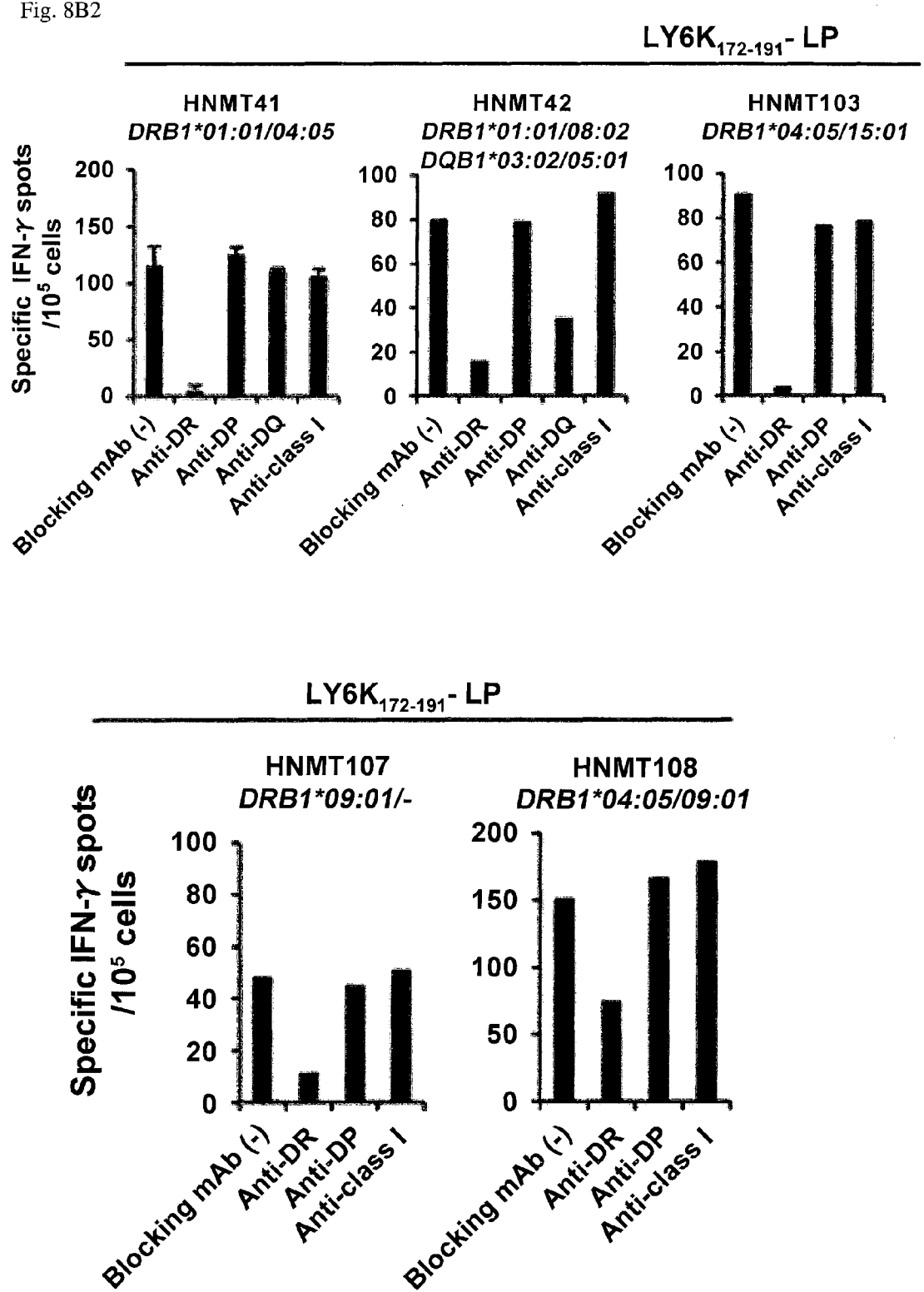

Fig. 8C-D
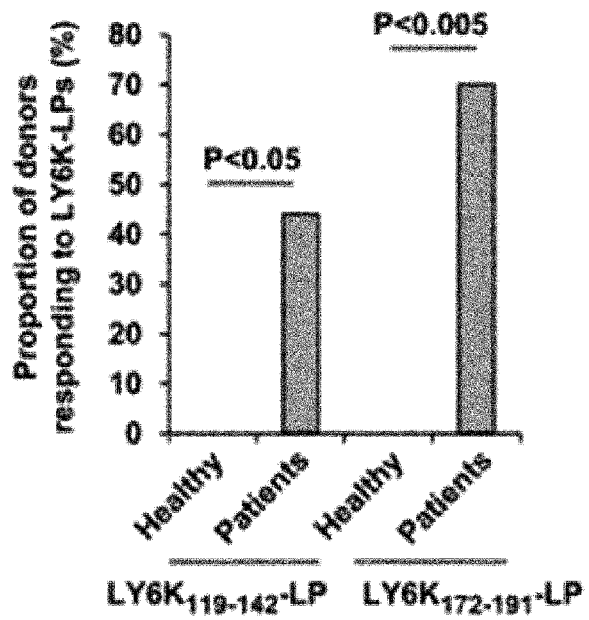
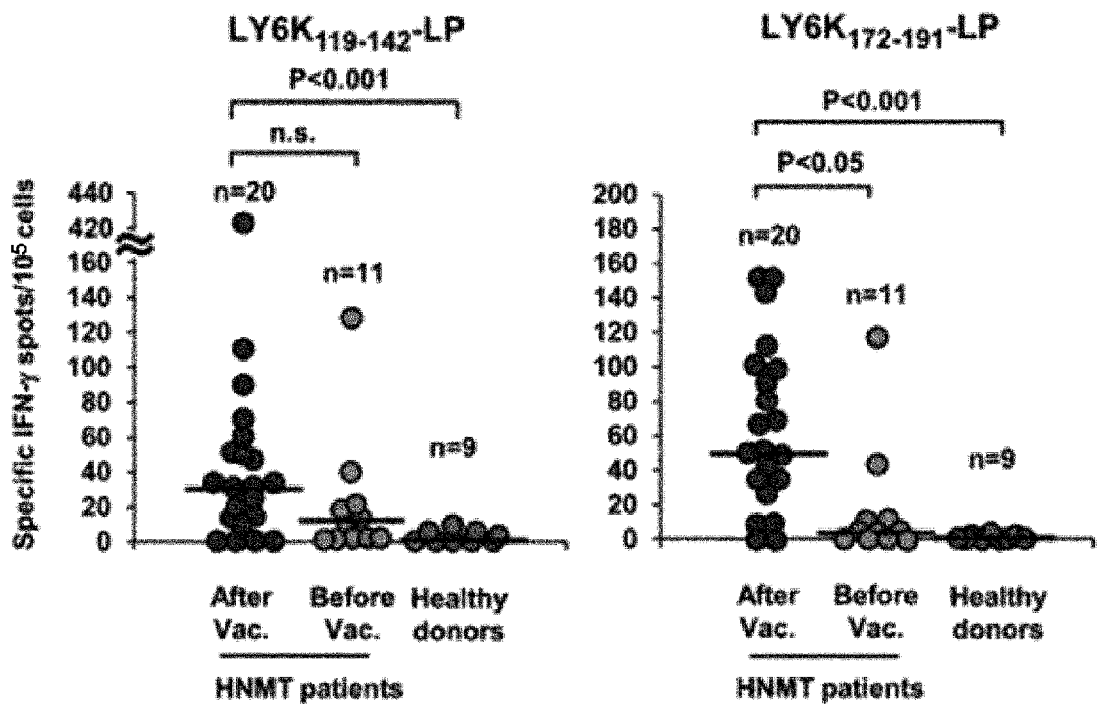

Fig. 9A-B
A
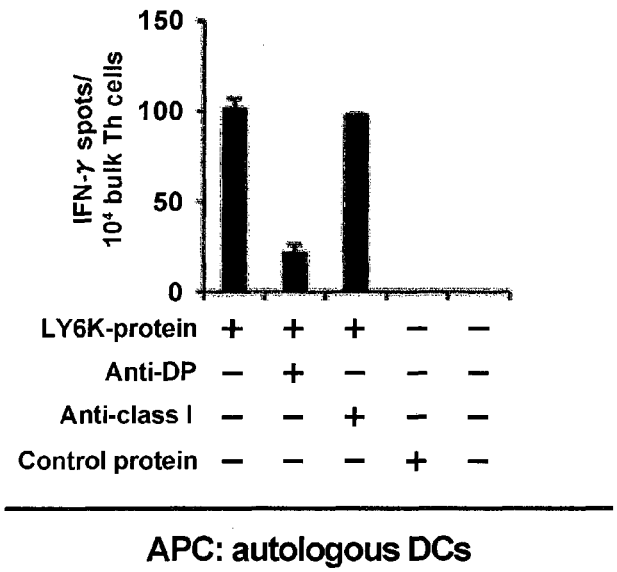
LY6K$_{119-142}$-LP-specific bulk Th cells
HDL1: *DPB1*05:01/-*
B
LY6K$_{172-191}$-LP-specific Th-clone
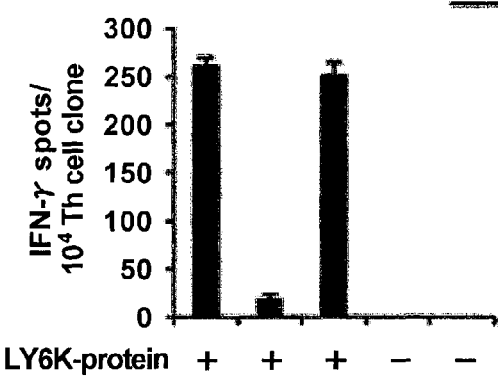
HDL2: *DRB1*08:03/15:02*
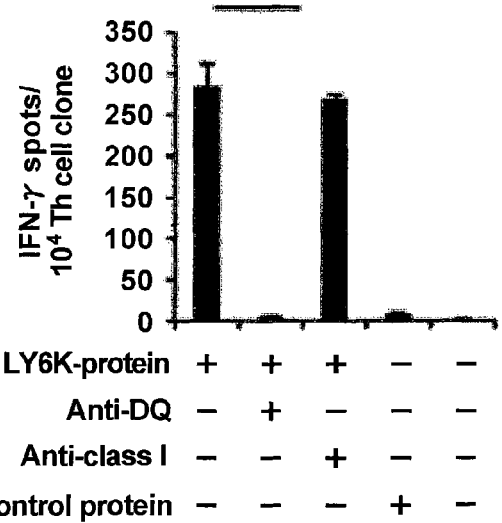
HDL4: *DQB1*05:03/06:01*

Fig. 10A-B
A
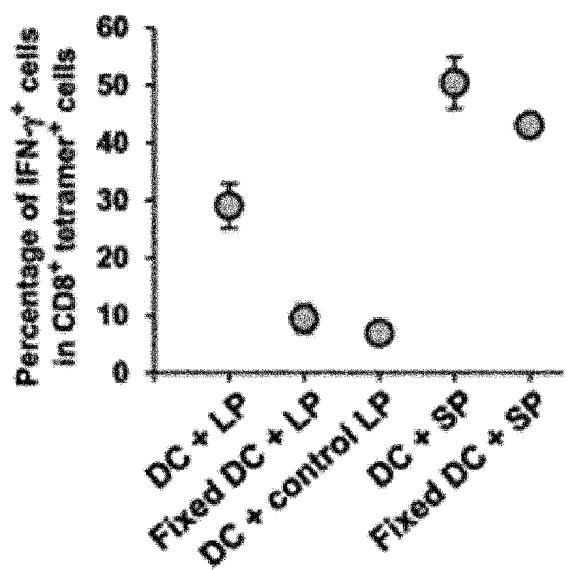
B
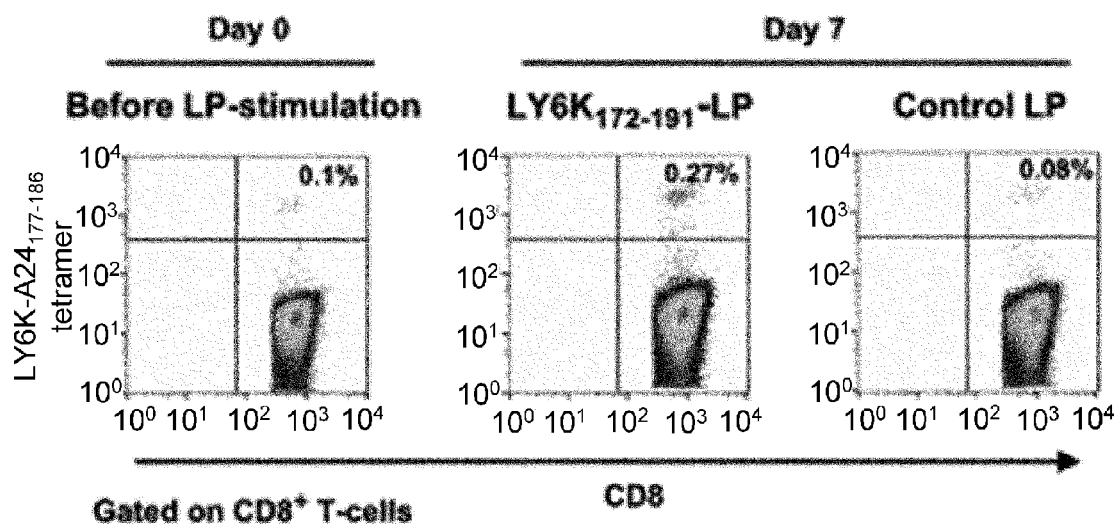

Fig. 10G-H
G
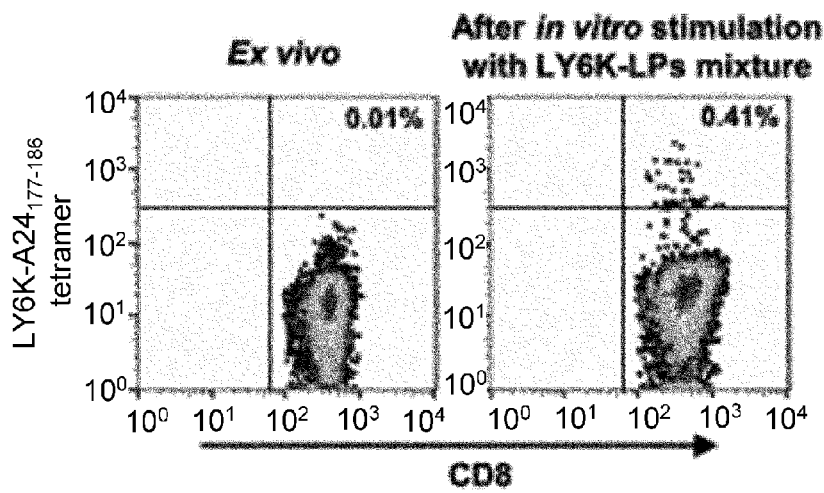
H
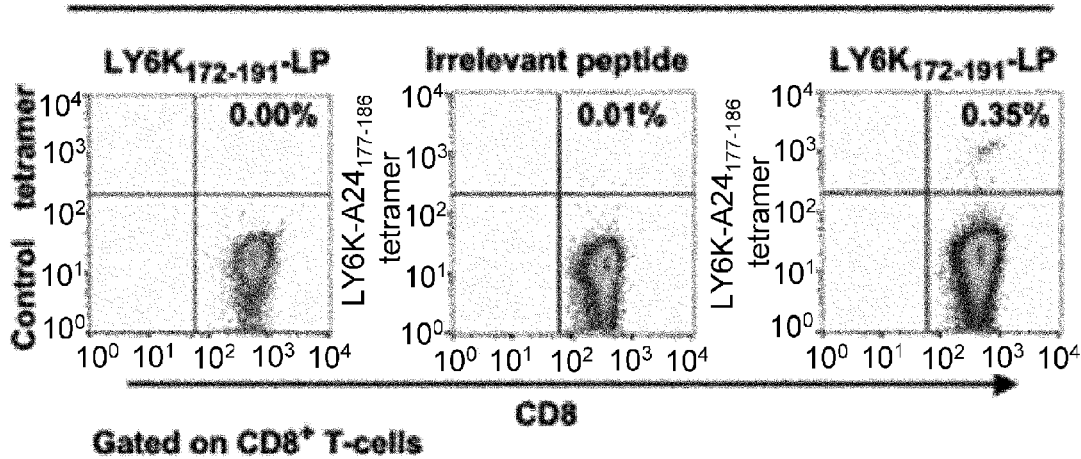

Fig. 11A
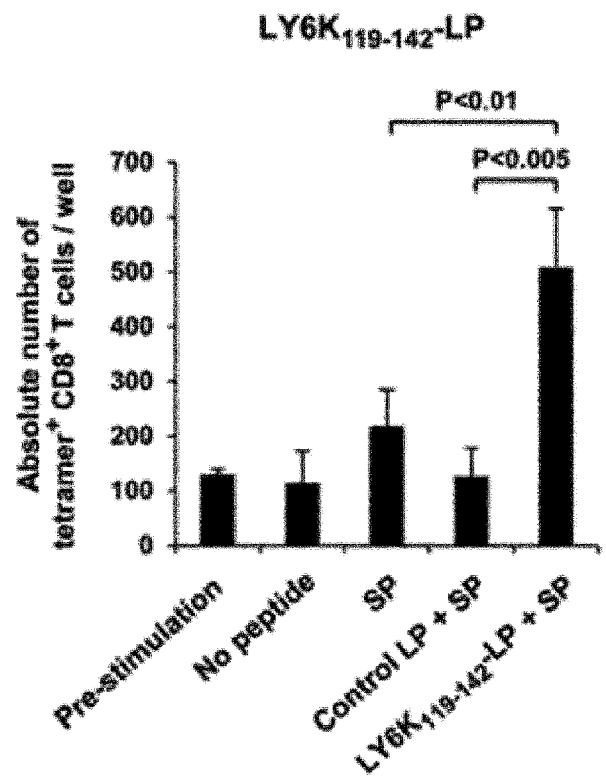
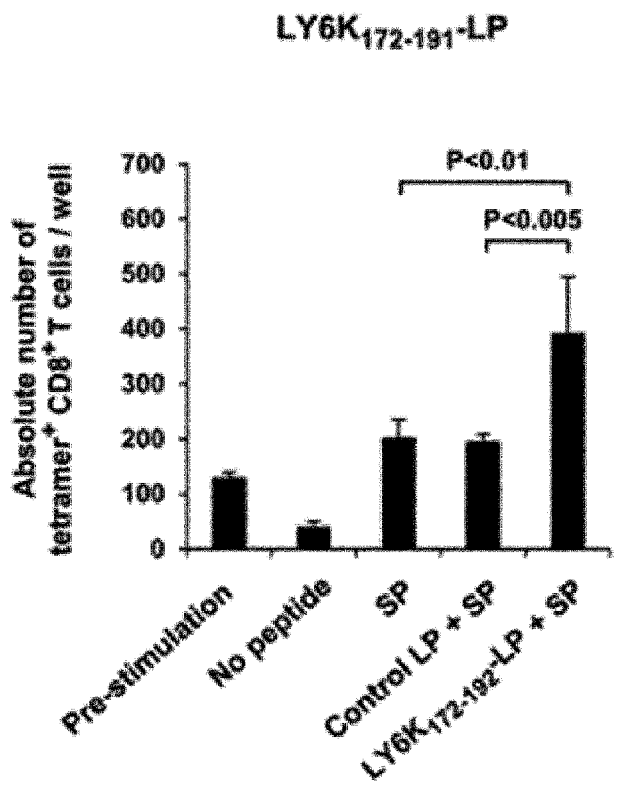

Fig. 11D
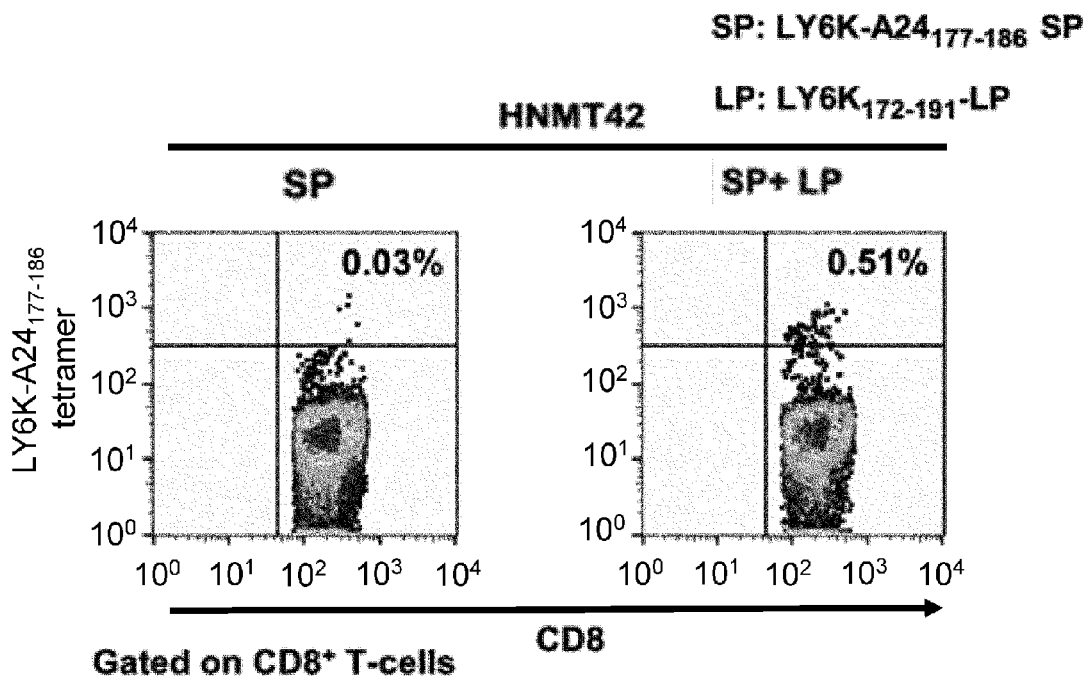
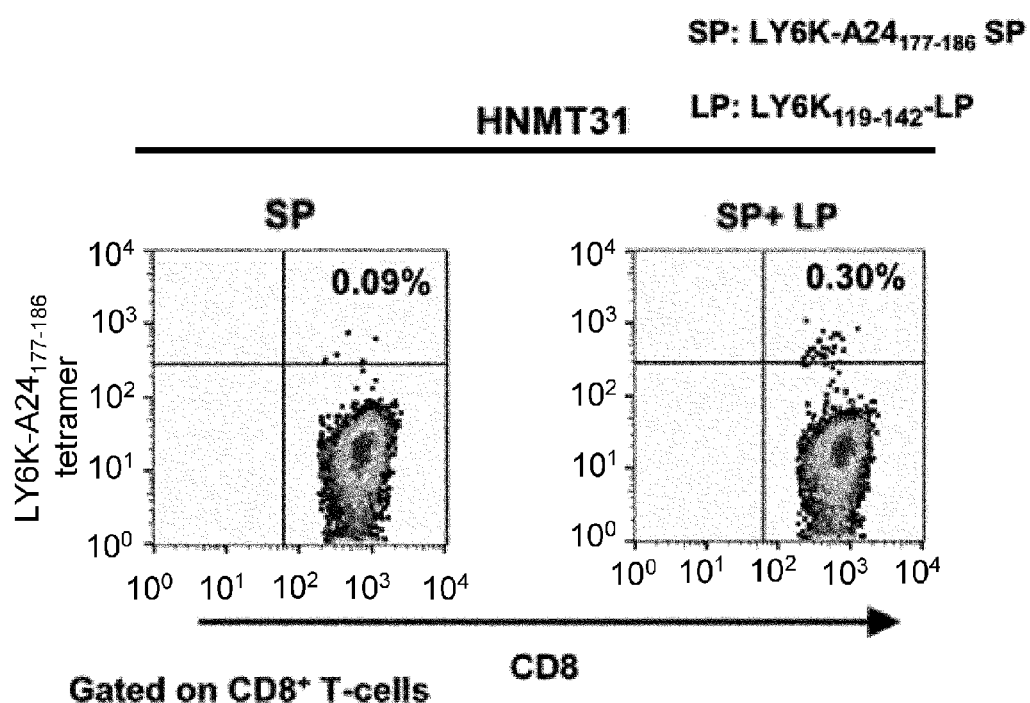

Fig. 12

Clinical characteristics of HNMT patients

| Patient ID | Age/Sex | LY6K-specific CD4+ T-cell responses[a] | | | | No. of vaccinations | Histologic subtype | HLA-DRB1 | HLA-DPB1 |
|---|---|---|---|---|---|---|---|---|---|
| | | LY6K$_{119-142}$-LP | | LY6K$_{172-191}$-LP | | | | | |
| | | Pre-vac. | Post-vac. | Pre-vac. | Post-vac. | | | | |
| CTR-8379 + CTR-8380 | | | | | | | | | |
| Positive/ Total (%) | | 10/23 (44%) | | 16/23 (70%) | | | | | |
| CTR-8379 | | Pre-vac. | Post-vac. | Pre-vac. | Post-vac. | | | | |
| Positive / Total (%) | | 2/7 (29%) | 4/13 (31%) | 1/7 (14%) | 8/13 (62%) | | | | |
| HNMT10 | 61/M | n.t. | - | n.t. | - | 60 | Squamous Cell Carcinoma | 01:01 / 04:05 | 05:01 / - |
| HNMT20 | 57/F | n.t. | + | n.t. | - | 32 | Squamous Cell Carcinoma | 01:01 / 09:01 | 02:01 / 05:01 |
| HNMT26 | 70/M | n.t. | - | n.t. | + | 24 | Basaloid Squamous Cell Carcinoma | 04:05 / 15:02 | 05:01 / 09:01 |
| HNMT29 | 64/F | n.t. | - | n.t. | + | 16 | Squamous Cell Carcinoma | 09:01 / 14:54 | 03:01 / 05:01 |
| HNMT31 | 69/F | n.t. | + | n.t. | + | 16 | Adenoid Cystic Carcinoma | 01:01 / 11:01 | 02:01 / 04:02 |
| HNMT34 | 65/M | n.t. | - | n.t. | + | 12 | Squamous Cell Carcinoma | 08:03 / 15:02 | 02:01 / 05:01 |
| HNMT35 | 85/F | n.t. | - | n.t. | - | 8 | Squamous Cell Carcinoma | 04:05 / 08:02 | 05:01 / - |
| HNMT39 | 77/M | - | - | - | + | 8 | Adenoid Cystic Carcinoma | 04:06 / 14:54 | 05:01 / 19:01 |
| HNMT40 | 76/M | - | - | - | - | 4 | Squamous Cell Carcinoma | 01:01 / 09:01 | 04:02 / 05:01 |
| HNMT41 | 51/F | + | + | + | + | 4 | Adenoid Cystic Carcinoma | 01:01 / 04:05 | 04:02 / 05:01 |
| HNMT42 | 36/F | + | + | - | + | 4 | Unknown | 01:01 / 08:02 | 04:02 / 05:01 |
| HNMT43 | 50/M | - | - | - | + | 4 | Squamous Cell Carcinoma | 08:02 / 09:01 | 05:01 / - |
| HNMT44 | 55/M | - | n.t. | - | n.t. | 0 | Malignant Melanoma | 01:01 / 13:02 | 04:01 / 09:01 |
| HNMT45 | 82/M | - | - | - | - | 8 | Squamous Cell Carcinoma | 04:03 / 14:03 | 05:01 / - |
| CTR-8380 | | Pre-vac. | Post-vac. | Pre-vac. | Post-vac. | | | | |
| Positive / Total (%) | | 0/4 (0%) | 6/8 (75%) | 0/4 (0%) | 8/8 (100%) | | | | |
| HNMT102 | 80/F | n.t. | + | n.t. | + | 33 | Squamous Cell Carcinoma | 15:02 / - | 02:01 / 09:01 |
| HNMT103 | 78/F | n.t. | + | n.t. | + | 20 | Mutinous Adenocarcinoma | 04:05 / 15:01 | 02:01 / 05:01 |
| HNMT105 | 65/M | n.t. | + | n.t. | + | 20 | Angiosarcoma | 04:05 / 13:02 | 03:01 / 04:01 |
| HNMT107 | 20/M | n.t. | + | n.t. | + | 20 | Osteosarcoma | 09:01 / - | 02:01 / 02:02 |
| HNMT108 | 41/M | n.t. | - | n.t. | + | 17 | Osteosarcoma | 04:05 / 09:01 | 05:01 / - |
| HNMT109 | 60/F | - | - | - | + | 4 | Squamous Cell Carcinoma | 04:03 / 04:05 | 02:01 / 05:01 |
| HNMT110 | 72/F | - | + | - | + | 8 | Verrucous Carcinoma | 04:10 / 15:02 | 03:01 / 09:01 |
| HNMT111 | 70/F | - | + | - | + | 4 | Squamous Cell Carcinoma | 09:01 / 15:02 | 05:01 / - |
| HNMT112 | 54/M | - | n.t. | - | n.t. | 0 | Squamous Cell Carcinoma | 08:02 / 15:01 | 02:01 / 04:01 |

SEQUENCE LISTING

```
<160> NUMBER OF SEQ ID NOS: 8

<210> SEQ ID NO 1
<211> LENGTH: 24
<212> TYPE: PRT
<213> ORGANISM: Artificial Sequence
<220> FEATURE:
<223> OTHER INFORMATION: An artificially synthesized peptide

<400> SEQUENCE: 1

Lys Trp Thr Glu Pro Tyr Cys Val Ile Ala Ala Val Lys Ile Phe Pro
1               5                   10                  15
```

```
Arg Phe Phe Met Val Ala Lys Gln
            20

<210> SEQ ID NO 2
<211> LENGTH: 20
<212> TYPE: PRT
<213> ORGANISM: Artificial Sequence
<220> FEATURE:
<223> OTHER INFORMATION: An artificially synthesized peptide

<400> SEQUENCE: 2

Lys Cys Cys Lys Ile Arg Tyr Cys Asn Leu Glu Gly Pro Pro Ile Asn
1               5                   10                  15

Ser Ser Val Phe
            20

<210> SEQ ID NO 3
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 3

Arg Tyr Cys Asn Leu Glu Gly Pro Pro Ile
1               5                   10

<210> SEQ ID NO 4
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 4

Arg Tyr Leu Arg Asp Gln Gln Leu Leu
1               5

<210> SEQ ID NO 5
<211> LENGTH: 18
<212> TYPE: PRT
<213> ORGANISM: Artificial Sequence
<220> FEATURE:
<223> OTHER INFORMATION: An artificially synthesized peptide

<400> SEQUENCE: 5

Phe Leu Gln Thr His Ile Phe Ala Glu Val Leu Lys Asp Ala Ile Lys
1               5                   10                  15

Asp Leu

<210> SEQ ID NO 6
<211> LENGTH: 25
<212> TYPE: PRT
<213> ORGANISM: Artificial Sequence
<220> FEATURE:
<223> OTHER INFORMATION: An artificially synthesized peptide

<400> SEQUENCE: 6

Phe Phe Tyr Leu Lys Cys Cys Lys Ile Arg Tyr Cys Asn Leu Glu Gly
1               5                   10                  15

Pro Pro Ile Asn Ser Ser Val Phe Lys
            20                  25

<210> SEQ ID NO 7
```

<211> LENGTH: 1747
<212> TYPE: DNA
<213> ORGANISM: Homo sapiens
<220> FEATURE:
<221> NAME/KEY: CDS
<222> LOCATION: (418)..(915)

<400> SEQUENCE: 7

```
gagttatcag aggtgagccc gtgctcttca gcggagaaga tcccctacct ggccgccggc    60
cactttctgt gggccgtggg gtcctcaagg agacggccct tgggctcagg ggctgcgttt   120
ccacacgcgc ctttcccagg gctcccgcgc ccgttcctgc ctggccgccg ccgctccaa    180 cagcagcaca aggcgggact cagaaccggg gttcagggcc gccagcggcc gcgaggccct   240
gagatgaggc tccaaagacc ccgacaggcc ccggcgggtg ggaggcgcgc gccccggggc   300
gggcggggct cccctaccg gccagacccg ggagaggcg cgcggaggct gcgaaggttc    360
cagaagggcg gggaggggc gccgcgcgct gaccctccct gggcaccgct ggggacg      417
```

| | | |
|---|---|---|
| atg gcg ctg ctc gcc ttg ctg ctg gtc gtg gcc cta ccg cgg gtg tgg<br>Met Ala Leu Leu Ala Leu Leu Leu Val Val Ala Leu Pro Arg Val Trp<br>1                5                10              15 | | 465 |
| aca gac gcc aac ctg act gcg aga caa cga gat cca gag gac tcc cag<br>Thr Asp Ala Asn Leu Thr Ala Arg Gln Arg Asp Pro Glu Asp Ser Gln<br>                20                    25                    30 | | 513 |
| cga acg gac gag ggt gac aat aga gtg tgg tgt cat gtt tgt gag aga<br>Arg Thr Asp Glu Gly Asp Asn Arg Val Trp Cys His Val Cys Glu Arg<br>           35                    40                    45 | | 561 |
| gaa aac act ttc gag tgc cag aac cca agg agg tgc aaa tgg aca gag<br>Glu Asn Thr Phe Glu Cys Gln Asn Pro Arg Arg Cys Lys Trp Thr Glu<br>50                      55                    60 | | 609 |
| cca tac tgc gtt ata gcg gcc gtg aaa ata ttt cca cgt ttt ttc atg<br>Pro Tyr Cys Val Ile Ala Ala Val Lys Ile Phe Pro Arg Phe Phe Met<br>65                      70                    75                    80 | | 657 |
| gtt gcg aag cag tgc tcc gct ggt tgt gca gcg atg gag aga ccc aag<br>Val Ala Lys Gln Cys Ser Ala Gly Cys Ala Ala Met Glu Arg Pro Lys<br>                       85                    90                    95 | | 705 |
| cca gag gag aag cgg ttt ctc ctg gaa gag ccc atg ccc ttc ttt tac<br>Pro Glu Glu Lys Arg Phe Leu Leu Glu Glu Pro Met Pro Phe Phe Tyr<br>                    100                    105                    110 | | 753 |
| ctc aag tgt tgt aaa att cgc tac tgc aat tta gag ggg cca cct atc<br>Leu Lys Cys Cys Lys Ile Arg Tyr Cys Asn Leu Glu Gly Pro Pro Ile<br>             115                    120                    125 | | 801 |
| aac tca tca gtg ttc aaa gaa tat gct ggg agc atg ggt gag agc tgt<br>Asn Ser Ser Val Phe Lys Glu Tyr Ala Gly Ser Met Gly Glu Ser Cys<br>130                      135                    140 | | 849 |
| ggt ggg ctg tgg ctg gcc atc ctc ctg ctg gcc tcc att gca gcc<br>Gly Gly Leu Trp Leu Ala Ile Leu Leu Leu Ala Ser Ile Ala Ala<br>145                      150                    155                    160 | | 897 |
| ggc ctc agc ctg tct tga gccacgggac tgccacagac tgagccttcc<br>Gly Leu Ser Leu Ser<br>             165 | | 945 |

```
ggagcatgga ctcgctccag accgttgtca cctgttgcat taaacttgtt ttctgttgat  1005
tacctcttgg tttgacttcc cagggtcttg ggatgggaga gtgggatca ggtgcagttg   1065 gctcttaacc ctcaagggtt ctttaactca cattcagagg aagtccagat ctcctgagta  1125
gtgattttgg tgacaagttt ttctctttga aatcaaacct tgtaactcat ttattgctga  1185
tggccactct tttccttgac tccctctgc ctctgagggc ttcagtattg atggggaggg   1245
aggcctaagt accactcatg gagagtatgt gctgagatgc ttccgacctt tcaggtgacg  1305
```

```
caggaacact gggggagtct gaatgattgg ggtgaagaca tccctggagt gaaggactcc    1365
tcagcatggg gggcagtggg gcacacgtta gggctgcccc cattccagtg gtggaggcgc    1425
tgtggatggc tgcttttcct caacctttcc taccagattc caggaggcag aagataacta    1485
attgtgttga agaaacttag acttcaccca ccagctggca caggtgcaca gattcataaa    1545
ttcccacacg tgtgtgttca acatctgaaa cttaggccaa gtagagagca tcagggtaaa    1605
tggcgttcat ttctctgtta agatgcagcc atccatgggg agctgagaaa tcagactcaa    1665
agttccacca aaaacaaata caaggggact tcaaaagttc acgaaaaaaa aaaaaaaaaa    1725
aaaaaaaaaa aaaaaaaaaa aa                                             1747

<210> SEQ ID NO 8
<211> LENGTH: 165
<212> TYPE: PRT
<213> ORGANISM: Homo sapiens

<400> SEQUENCE: 8

Met Ala Leu Leu Ala Leu Leu Leu Val Val Ala Leu Pro Arg Val Trp
1               5                   10                  15

Thr Asp Ala Asn Leu Thr Ala Arg Gln Arg Asp Pro Glu Asp Ser Gln
            20                  25                  30

Arg Thr Asp Glu Gly Asp Asn Arg Val Trp Cys His Val Cys Glu Arg
        35                  40                  45

Glu Asn Thr Phe Glu Cys Gln Asn Pro Arg Arg Cys Lys Trp Thr Glu
    50                  55                  60

Pro Tyr Cys Val Ile Ala Ala Val Lys Ile Phe Pro Arg Phe Phe Met
65                  70                  75                  80

Val Ala Lys Gln Cys Ser Ala Gly Cys Ala Ala Met Glu Arg Pro Lys
                85                  90                  95

Pro Glu Glu Lys Arg Phe Leu Leu Glu Glu Pro Met Pro Phe Phe Tyr
            100                 105                 110

Leu Lys Cys Cys Lys Ile Arg Tyr Cys Asn Leu Glu Gly Pro Pro Ile
        115                 120                 125

Asn Ser Ser Val Phe Lys Glu Tyr Ala Gly Ser Met Gly Glu Ser Cys
    130                 135                 140

Gly Gly Leu Trp Leu Ala Ile Leu Leu Leu Leu Ala Ser Ile Ala Ala
145                 150                 155                 160

Gly Leu Ser Leu Ser
                165
```

LY6K EPITOPE PEPTIDES FOR TH1 CELLS AND VACCINES CONTAINING THE SAME

CROSS-REFERENCES TO RELATED APPLICATIONS

This application is a National Stage of International Application No. PCT/JP2013/004249, filed Jul. 9, 2013, and which claims the benefit of U.S. Provisional Application No. 61/669,995, filed on Jul. 10, 2012, the entire contents of which are incorporated by reference herein.

TECHNICAL FIELD

The present invention relates to the field of biological science, more specifically to the field of cancer therapy. In particular, the present invention relates to novel peptides that are extremely effective as cancer vaccines, and drugs for either or both of treating and preventing tumors.

REFERENCE TO SEQUENCE LISTING

This application includes a Sequence Listing as a text file named "87331-927972-SEQLIST.txt" created Dec. 17, 2014, and containing 7,784 bytes. The material contained in this text file is incorporated by reference in its entirety for all purposes.

BACKGROUND ART

CD8 positive cytotoxic T lymphocytes (CTLs) have been shown to recognize epitope peptides derived from the tumor-associated antigens (TAAs) found on the major histocompatibility complex (MHC) class I molecule, and then kill the tumor cells. Since the discovery of the melanoma antigen (MAGE) family as the first example of TAAs, many other TAAs have been discovered, primarily through immunological approaches (NPL 1, 2). Some of these TAAs are currently undergoing clinical development as immunotherapeutic targets.

TAAs which are indispensable for proliferation and survival of cancer cells are valiant as targets for immunotherapy, because the use of such TAAs may minimize the well-described risk of immune escape of cancer cells attributable to deletion, mutation, or down-regulation of TAAs as a consequence of therapeutically driven immune selection.

Accordingly, the identification of new TAAs capable of inducing potent and specific anti-tumor immune responses, warrants further development. Thus, the clinical application of peptide vaccination strategies for various types of cancer is ongoing (NPL 3-10). To date, there have been several reports of clinical trials using these tumor-associated antigen derived peptides. Unfortunately, so far, these cancer vaccine trials have yielded only a low objective response rate has been observed in these cancer vaccine trials so far (NPL 11-13). Accordingly, there remains a need in the art for new TAAs suitable for use as immunotherapeutic targets.

LY6K was initially identified by several groups (Accession No. NM_017527; SEQ ID NO: 8 encoded by SEQ ID NO: 7) as an unannotated transcript. More recent analysis by bioinformatics classified it as a member belonging to the LY6 family having a high homology to the low molecular-weight GPI-anchored molecule (NPL 14). Like others in the LY6 family, LY6K has 10 cysteine residues in a conserved position and harbors the sequence structure that, in theory, determines GPI anchoring. Members of the LY6 family believed to possess functions related to cell signaling and/or cell adhesion (NPL 15), although the precise role of LY6K in lung carcinogenesis or its physiological function in normal cells is presently unknown. Since the LY6K gene is located at chromosome 8q24, a region of allelic gain in more than half of lung cancers (NPL 16), its over-expression may result from amplification or chromosomal aberration at this locus.

Through gene expression profile analysis using a genome-wide cDNA microarray containing 23,040 genes, LY6K was recently shown to be up-regulated in several cancers such as bladder cancer, cervical cancer, cholangiocellular carcinoma, esophageal cancer, gastric cancer, non-small cell lung cancer (NSCLC), osteosarcoma, pancreatic cancer and soft tissue tumor (PTL 1, PTL 2, PTL 3).

Taken together, this data suggests that LY6K is a novel, potentially universal on-coantigen. Accordingly, epitope peptides derived from LY6K may be applicable as cancer immunotherapeutics for the treatment of a wide array of cancers.

Recently, highly immunogenic LY6-derived cytotoxic T lymphocytes (CTL)-epitopes that can induce tumor-reactive and HLA-A2 (A*02:01)-restricted CTL from PBMCs of healthy volunteers (PTL 1) have been identified. Furthermore, LY6K-derived HLA-A24-restricted CTL-epitopes have been also identified (NPL 17, PTL 4). Therefore, LY6K remains an attractive target molecule applicable to cancer immunotherapy.

Tumor-specific $CD4^+$ helper T (Th) cells, especially T-helper type 1 (Th1) cells play a critical role in efficient induction of CTL-mediated antitumor immunity (NPL 18). The IFN-gamma primarily produced by Th1 cells is critical for induction and maintenance of long lived CTL responses by providing help through multiple interactions, which are critical in the preservation of immunological memory (NPL 19, 20). The IFN-gamma secreted by Th1 cells also mediates direct antitumor or anti-angiogenic effect (NPL 21). Furthermore, it has been shown that Th cells must pave the way for entry of CTLs at tumor site (NPL 22). Therefore, identification of tumor-associated antigen (TAA)-derived Th cell epitopes that can activate specific Th1 cell is important for induction of an effective tumor immunity in tumor-bearing hosts; ideally, the design of effective vaccines should include multiple epitopes to stimulate both CTL and Th1 cells (NPL 23). However, no such epitope derived from LY6K has yet been identified.

CITATION LIST

Patent Literature

[PTL 1] WO2008/102557
[PTL 2] WO2009/016691
[PTL 3] WO2004/031413
[PTL 4] WO2006/090810

Non Patent Literature

[NPL 1] Boon T, Int J Cancer 1993 May 8, 54(2): 177-80
[NPL 2] Boon T and van der Bruggen P, J Exp Med 1996 Mar. 1, 183(3): 725-9
[NPL 3] Harris C C, J Natl Cancer Inst 1996 Oct. 16, 88(20): 1442-55
[NPL 4] Butterfield L H et al., Cancer Res 1999 Jul. 1, 59(13): 3134-42
[NPL 5] Vissers J L et al., Cancer Res 1999 Nov. 1, 59(21): 5554-9

[NPL 6] van der Burg S H et al., J Immunol 1996 May 1, 156(9): 3308-14

[NPL 7] Tanaka F et al., Cancer Res 1997 Oct. 15, 57(20): 4465-8

[NPL 8] Fujie T et al., Int J Cancer 1999 Jan. 18, 80(2): 169-72

[NPL 9] Kikuchi M et al., Int J Cancer 1999 May 5, 81(3): 459-66

[NPL 10] Oiso M et al., Int J Cancer 1999 May 5, 81(3): 387-94

[NPL 11] Belli F et al., J Clin Oncol 2002 Oct. 15, 20(20): 4169-80

[NPL 12] Coulie P G et al., Immunol Rev 2002 October, 188: 33-42

[NPL 13] Rosenberg S A et al., Nat Med 2004 September, 10(9): 909-15

[NPL 14] de Nooij-van Dalen A G, et al. Int J Cancer. 2003 Mar. 1; 103(6):768-74.

[NPL 15] Bamezai A & Rock K L. Proc Natl Acad Sci USA. 1995 May 9; 92(10):4294-8.

[NPL 16] Balsara B R, et al. Cancer Res. 1997 Jun. 1; 57(11):2116-20.

[NPL 17] Suda, et al. Cancer Sci. 2007 November; 98(11): 1803-8.

[NPL 18] Chamoto K et al. Cancer Res 2004; 64: 386-90.

[NPL 19] Bevan M J. Nat Rev Immunol 2004; 4: 595-602.

[NPL 20] Shedlock D J and Shen H. Science 2003; 300: 337-9.

[NPL 21] Street S E et al. Blood 2001; 97: 192-7.

[NPL 22] Bos R, and Sherman L A. Cancer Res; 70: 8368-77.

[NPL 23] Melief C J et al. Nat Rev Cancer 2008; 8: 351-60.

SUMMARY OF INVENTION

In the context of the present invention, the present inventors considered an ideal peptide vaccine for cancer immunotherapy to be one that includes a single polypeptide containing epitopes for both CTL and Th1 cell, both of which are naturally proximal to each other (Kenter G G et al. N Engl J Med 2009; 361: 1838-47.).

To that end, the present inventors designed a strategy to identify novel LY6K-derived Th1 cell epitopes recognized in the context of promiscuous HLA class II molecules and containing CTL epitopes, working on the presumption that epitopes so characterized would induce more efficient T cell-mediated tumor immunity. A computer algorithm predicting HLA class II-binding peptides and known CTL epitope sequences recognized by HLA-A24 (A*24:02)-restricted CTLs was used to select candidate promiscuous HLA-class II-restricted Th1 cell epitopes containing CTL epitopes.

The present invention is based, at least in part, on the discovery of suitable epitope peptides that serve as targets of immunotherapy for inducing Th1 cell response. Recognizing that the LY6K gene is up-regulated in a number of cancer types, including bladder cancer, cervical cancer, cholangiocellular carcinoma, esophageal cancer, gastric cancer, non-small cell lung cancer (NSCLC), osteosarcoma, pancreatic cancer and soft tissue tumor and head-and-neck malignant tumor (HNMT), the present invention targets for further analysis the gene product of lymphocyte antigen 6 complex, locus K (LY6K) gene, more particularly the polypeptide set forth in SEQ ID NO: 8 encoded by the gene of GenBank Accession No. NM_017527 (SEQ ID NO: 7)) LY6K gene products containing epitope peptides that elicit Th1 cells specific to the corresponding molecule were particularly selected for further study. For example, peripheral blood mononuclear cells (PBMCs) obtained from a healthy donor or HNMT patients were stimulated using promiscuous HLA-DRs, DPs and/or DQs binding peptide derived from human LY6K. Th1 cells that recognize HLA-DRs, DPs, or DQs positive target cells pulsed with the respective candidate peptides were established, and HLA-DRs, DPs, and/or DQs restricted epitope peptides that can induce potent and specific immune responses against LY6K were identified. These results demonstrate that LY6K is strongly immunogenic and the epitopes thereof are effective for tumor immunotherapy mediated through Th1 cell response. Additional studies revealed that the promiscuous HLA-DRs, and/or DQs binding peptides containing at least one CTL epitope can also stimulate CTL response in the same donor in a LY6K specific manner. These results confirm that LY6K is strongly immunogenic and that epitopes thereof containing both Th1 cell and CTL epitopes are effective for tumor immunotherapy mediated through both Th1 cell and CTL responses.

It is therefore an object of the present invention to provide peptides having Th1 cell inducibility as well as an amino acid sequence selected from among SEQ ID NOs: 1 and 2. The present invention contemplates modified peptides, i.e., peptides having Th1 cell inducibility that are up to 30 amino acids in length and have a contiguous amino acid sequence selected from the amino acid sequence of SEQ ID NO: 8 (LY6K), as well as functional equivalents thereof. Alternatively, the present invention also provides peptides having both Th1 cell and CTL inducibilities. In some embodiments, the peptides of the present invention correspond to the amino acid sequence of SEQ ID NO: 1 or 2 or modified versions thereof, in which one, two or several amino acids are substituted, deleted, inserted and/or added, while the ability to induce Th1 cells is maintained.

When administered to a subject, the present peptides are preferably presented on the surface of one or more antigen-presenting cells (APCs) that in turn induce Th1 cells. When the peptide of the present invention further contains at least one CTL epitope, such APCs also process the peptides to present CTL epitopes generated from the present peptides, and thus induce CTLs targeting the respective peptides. Therefore, it is a further object of the present invention to provide antigen-presenting cells presenting any of the present peptides or fragments thereof, as well as methods for inducing antigen-presenting cells.

Administration of one or more peptides of the present invention or polynucleotide(s) encoding such peptides, or antigen-presenting cells which present such peptides or fragment thereof results in the induction of a strong anti-tumor immune response. Accordingly, it is yet another object of the present invention to provide pharmaceutical agents or compositions that contain as active ingredient(s) one or more of the following: (a) one or more peptides of the present invention, (b) one or more polynucleotides encoding such peptide(s), and (c) one or more the antigen-presenting cells of the present invention. Such pharmaceutical agents or compositions of the present invention find particular utility as vaccines.

It is yet a further object of the present invention to provide methods for the treatment and/or prophylaxis (i.e., prevention) of cancers (i.e., tumors), and/or prevention of a post-operative recurrence thereof. Methods for inducing Th1 cells, or for inducing anti-tumor immunity, that include the step of administering one or more peptides, polynucleotides, antigen-presenting cells or pharmaceutical agents or compositions of the present invention are also contemplated. Furthermore, the Th1 cells of the present invention also find use as vaccines against cancer, examples of which include, but are not limited to, bladder cancer, cervical cancer, cholangiocellular carcinoma, esophageal cancer, gastric cancer, non-small cell lung cancer (NSCLC), osteosarcoma, pancreatic cancer, soft tissue tumor and head-and-neck malignant tumor (HNMT).

Examples of specifically contemplated objects of the present invention include the following:

[1] An isolated peptide having 10-30 amino acids in length and comprising a part of the amino acid sequence of SEQ ID NO: 8, wherein said peptide comprises an amino acid sequence selected from the group consisting of:
  (a) a contiguous amino acid sequence having more than 9 amino acids in length selected from the amino acid sequence of SEQ ID NO: 1 or 2; and
  (b) an amino acid sequence in which one, two or several amino acids are substituted, deleted, inserted, and/or added in the amino acid sequence of (a), wherein said peptide has ability to induce T helper type 1 (Th1) cells.

[2] The isolated peptide of [1], wherein the peptide or fragment thereof has abilities to bind at least two kinds of MHC class II molecules.

[3] The isolated peptide of [2], wherein the MHC class II molecules are selected from the group consisting of HLA-DP5, HLA-DR15, HLA-DR8 and one of HLA-DQs.

[4] The isolated peptide of any one of [1] to [3], wherein said peptide comprises an amino acid sequence of a peptide having LY6K-specific cytotoxic T lymphocyte (CTL) inducibility.

[5] The isolated peptide of [4], wherein said peptide comprises the amino acid sequence selected from the group consisting of:
  (a) an amino acid sequence selected from the group consisting of SEQ ID NOs: 1 and 2; and
  (b) an amino acid sequence in which one, two or several amino acids are substituted, deleted, inserted, and/or added in the amino acid sequence of (a).

[6] The isolated peptide of [5], wherein said peptide comprises the amino acid sequence of SEQ ID NO: 6.

[7] An isolated polynucleotide encoding the peptide of any one of [1] to [6].

[8] A composition for inducing at least one of the cells selected from the group consisting of
  (i) Th1 cells,
  (ii) CTLs,
  (iii) antigen-presenting cells (APCs) having an ability to induce Th1 cells, and
  (iv) APCs having an ability to induce CTLs,
  wherein the composition comprises one or more peptide(s) of any one of [1] to [6], or one or
  more polynucleotide(s) encoding them, or a composition for inducing at least one type of cell
  selected from the group consisting of
  (i) Th1 cells,
  (ii) CTLs,
  (iii) antigen-presenting cells (APCs) having an ability to induce Th1 cells, and
  (iv) APCs having an ability to induce CTLs,
  wherein the composition comprises one or more peptide(s) of any one of [1] to [5], or one or
  more polynucleotide(s) encoding them.

[9] A pharmaceutical composition, wherein the composition comprises at least one active ingredient selected from the group consisting of:
  (a) one or more peptide(s) of any one of [1] to [6];
  (b) one or more polynucleotide(s) of [7];
  (c) one or more APC(s) presenting the peptide of any one of [1] to [6] or fragment thereof on their surface;
  (d) one or more Th1 cells that recognize(s) an APC presenting the peptide of any one of [1] to [6] or fragment thereof on its surface; and
  (e) combination of any two or more of (a) to (d) above;
and is
formulated for a purpose selected from the group consisting of:
  (i) cancer treatment,
  (ii) cancer prevention,
  (iii) prevention of post-operative recurrence in cancer, and
  (iv) combinations of any two or more of (i) to (iii) above.

[10] The pharmaceutical composition of [9], wherein said composition is formulated for administration to a subject that has at least one selected from the group consisting of HLA-DP5, HLA-DR15 and HLA-DR8 as a MHC class II molecule, or the pharmaceutical composition of [9], wherein said composition is formulated for administration to a subject that has at least one MHC class II molecule selected from the group consisting of HLA-DP5, HLA-DR15 and HLA-DR8.

[11] The pharmaceutical composition of [9] or [10], wherein said composition further comprises one or more peptides having CTL inducibility.

[12] A composition for enhancing an immune response mediated with an MHC class II molecule, wherein the composition comprises at least one active ingredient selected from the group consisting of:
  (a) one or more peptide(s) of any one of [1] to [6];
  (b) one or more polynucleotide(s) of [7];
  (c) one or more APC(s) presenting the peptide of any one of [1] to [6] or fragment thereof on their surface;
  (d) one or more Th1 cell(s) that recognize(s) an APC presenting the peptide of any one of [1] to [6] or fragment thereof on its surface; and
  (e) combination of any two or more of (a) to (d) above.

[13] A method for inducing an APC having an ability to induce a Th1 cell, said method comprising a step of contacting an APC with the peptide of any one of [1] to [6] in vitro, ex vivo or in vivo.

[14] A method for inducing an APC having an ability to induce a CTL, said method comprising a step selected from the group consisting of:
  (a) contacting an APC with the peptide of any one of [1] to [6] in vitro, ex vivo or in vivo; and
  (b) introducing a polynucleotide encoding the peptide of any one of [1] to [6] into an APC.

[15] A method for inducing a Th1 cell, said method comprising a step selected from the group consisting of:
  (a) co-culturing a CD4-positive T cell with an APC that presents on its surface a complex of an MHC class II molecule and the peptide of any one of [1] to [6] or fragment thereof; and
  (b) introducing a polynucleotide encoding both of T cell receptor (TCR) subunits, or polynucleotides encoding each of TCR subunits into a CD4-positive T cell, wherein the TCR can bind to a complex of an MHC class II molecule and the peptide of any one of [1] to [6] or fragment thereof presented on cell surface, or a method for inducing a Th1 cell, said method comprising a step selected from the group consisting of:

(a) co-culturing a CD4-positive T cell with an APC that presents on its surface a complex of an MHC class II molecule and the peptide of any one of [1] to [6] or fragment thereof; and (b) introducing a single polynucleotide encoding both T cell receptor (TCR) subunits, or multiple polynucleotides each encoding a separate TCR subunits into a CD4-positive T cell, wherein the TCR can bind to a complex of an MHC class II molecule and the peptide of any one of [1] to [6] or fragment thereof presented on a cell surface of an APC.

[16] A method for inducing a CTL, said method comprising the step selected from the group consisting of:

(a) co-culturing both of a CD4-positive T cell and a CD8-positive T cell with APCs contacted with the peptide of any one of [4] to [6]; and (b) co-culturing a CD8-positive T cell with an APC contacted with the peptide of any one of [4] to [6].

[17] A method for enhancing an immune response mediated by an MHC class II molecule, wherein the method comprises a step of administering to a subject at least one active ingredient selected from the group consisting of:

(a) one or more peptide(s) of any one of [1] to [6];

(b) one or more polynucleotide(s) of [7];

(c) one or more APC(s) presenting the peptide of any one of [1] to [6] or fragment thereof on their surface;

(d) one or more Th1 cell(s) that recognize(s) an APC presenting the peptide of any one of [1] to [6] or fragment thereof on its surface; and (e) combination of any two or more of (a) to (d) above.

[18] An isolated APC that presents on its surface a complex of an MHC class II molecule and the peptide of any one of [1] to [6] or fragment thereof.

[19] The APC induced by the method of [13] or [14].

[20] An isolated Th1 cell that recognizes the peptide of any one of [1] to [6] or fragment thereof presented on a surface of an APC.

[21] The Th1 cell induced by the method of [15].

[22] A method of inducing an immune response against cancer in a subject in need thereof, said method comprising the step of administering to the subject a composition comprising at least one active ingredient selected from the group consisting of:

(a) one or more peptide(s) of any one of [1] to [6];

(b) one or more polynucleotide(s) of [7];

(c) one or more APC(s) presenting the peptide of any one of [1] to [6] or fragment thereof on their surface;

(d) one or more Th1 cell(s) that recognize(s) an APC presenting the peptide of any one of [1] to [6] or fragment thereof on its surface; and (e) combination of any two or more of (a) to (d) above.

[23] An antibody or immunologically active fragment thereof against the peptide of any one of [1] to [6].

[24] A vector comprising a nucleotide sequence encoding the peptide of any one of [1] to [6].

[25] A host cell transformed or transfected with the expression vector of [24].

[26] A diagnostic kit comprising the peptide of any one of [1] to [6], the polynucleotide of [7] or the antibody of [23].

In addition to the above, other objects and features of the invention will become more fully apparent when the following detailed description is read in conjunction with the accompanying figures and examples. However, it is to be understood that both the foregoing summary of the invention and the following detailed description are of exemplified embodiments, and not restrictive of the invention or other alternate embodiments of the invention. In particular, while the invention is described herein with reference to a number of specific embodiments, it will be appreciated that the description is illustrative of the invention and is not construed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF DRAWINGS

Various aspects and applications of the present invention will become apparent to the skilled artisan upon consideration of the brief description of the figures and the detailed description of the present invention and its preferred embodiments which follows.

Figure 1A:
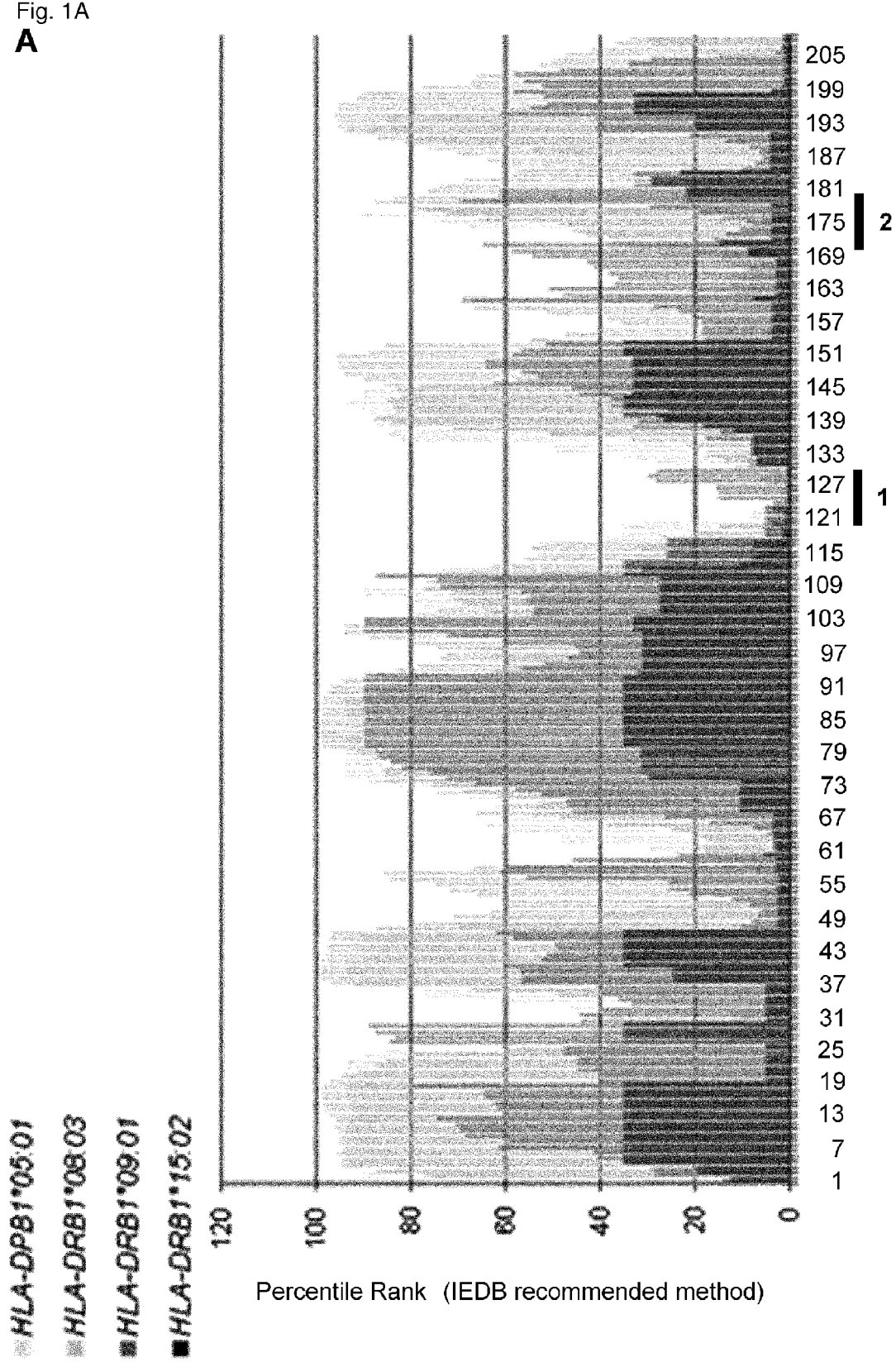
FIG. 1 presents promiscuous HLA class II-binding LY6K derived peptides predicted by the computer algorithm (IEDB recommended method). Part A depicts the results of the analysis of the amino acid sequence of the human LY6K protein using a computer algorithm (IEBD analysis resource, http://tools.immuneepitope.org/analyze/html/mhc_II_binding.html). The numbers of horizontal axis indicate the amino acid residue positions of N-terminus of LY6K-derived 15-mer peptides. Higher consensus percentile rank indicates stronger binding affinity to HLA class II molecules.

Part B depicts the two overlapping 24-mer and 20-mer long peptides (LY6K (119-142) and LY6K (172-191)) that have overlapping high consensus percentile ranks for multiple HLA-class II allelic products (DPB1*05:01, DRB1*08:03, DRB1*9:01, and DRB1*15:02) were selected as indicated by black bars numbered with 1 and 2 in the panel A, and synthesized to identify promiscuous HLA class II-restricted Th cell epitopes. LY6K (172-191) include 10-mer peptides recognized in the context of HLA-A24 by CTLs.

FIG. 2 presents the induction of LY6K (119-142)-specific CD4+ T cell lines by stimulation of peripheral CD4+ T cells with the LY6K (119-142) peptide and identification of antigen-presenting HLA-class II molecules. CD4+ T cell lines were generated from 3 healthy donors with various HLA-class II genotypes after at least 3 rounds of stimulation of peripheral CD4+ T cells with LY6K (119-142), and the numbers of IFN-gamma-producing CD4+ T cells were analyzed by ELISPOT assay. In Part A, the responses against LY6K (119-142) are shown for 3 healthy donors. The CD4+ T cells were stimulated with autologous PBMC alone (no peptide), PBMC pulsed with LY6K (119-142) (10 micro-g/ml), or PBMC pulsed with LY6K (119-142) in the presence of 5 micro-g/ml of mAb specific to HLA-DR, -DP or -DQ.

In Part B, the recognition of the LY6K (119-142) peptides by Th cells restricted by various HLA class II molecules. LY6K (119-142)-specific CD4+ T cell line established from three healthy donors were cocultured with L cells expressing indicated HLA-class II molecules (DP5, DR4, DR8 or DR15) pulsed or unpulsed with LY6K (119-142), L cells pulsed with LY6K (119-142) in the presence of anti-HLA-DR, anti-HLA-DP or anti-HLA class I blocking mAb or L-DP5 pulsed with EBNA-DP5. The numbers of IFNgamma-producing Th cells were analyzed by an ELISPOT assay. HLA types of the donors were indicated at the top of each panel. Data are presented as the mean+/−SD of duplicate or triplicate assays. Representative data from at least three independent experiments with similar results are shown.

FIG. 2B2 is a continuation of FIG. 2B1.

FIG. 3 presents the induction of LY6K (172-191)-specific CD4+ T cell lines by stimulation of peripheral CD4+ T cells with the LY6K (172-191) peptide and identification of antigen-presenting HLA-class II molecules. CD4+ T cell lines were generated from 3 healthy donors with various HLA-class II genotypes. After at least 3 rounds of stimulation of peripheral CD4+ T cells with LY6K (172-191), the numbers of IFN-gamma-producing CD4+ T cells were analyzed by ELISPOT assay. In Part A, Upper Part; Left panel; responses against LY6K (172-191) are shown for an HLA-DR8 and -DR15-positive healthy donor. The CD4+ T cells were stimulated with autologous PBMC alone (−), PBMC pulsed with LY6K (172-191) (10 micro-g/ml), or PBMC pulsed with LY6K (172-191) in the presence of 5 micro-g/ml of mAb specific to HLA-DR, DP or DQ. Right panel; recognition of the LY6K (172-191) peptides by Th cells restricted by HLA-DR15 molecule. LY6K (172-191)-specific CD4+ T cell line established from a healthy donor-HDL3 were cocultured with L-DR8 or -DR15 pulsed or unpulsed with LY6K (172-191), or L-DR15 cells pulsed with LY6K (172-191) in the presence of anti-HLA-DR or anti-HLA class I blocking mAb. In Part A, Lower Part; HLA-DR15-restricted LY6K (172-191) LP-specific Th cells were generated from HDL2.

In Part B, the responses against LY6K (172-191) are shown for a healthy donor-HDL4. The CD4+ T cells were stimulated with autologous PBMC alone (no peptide), PBMC pulsed with LY6K (172-191) (10 micro-g/ml), or PBMC pulsed with LY6K (172-191) in the presence of 5 micro-g/ml of mAb specific to HLA-DR, -DP or -DQ. The numbers of IFN-gamma-producing Th cells were analyzed by an ELISPOT assay. HLA types of the donors were indicated at the top of each panel. Data are presented as the mean+/−SD of duplicate or triplicate assays. Representative data from at least three independent experiments with similar results are shown.

Figure 4:
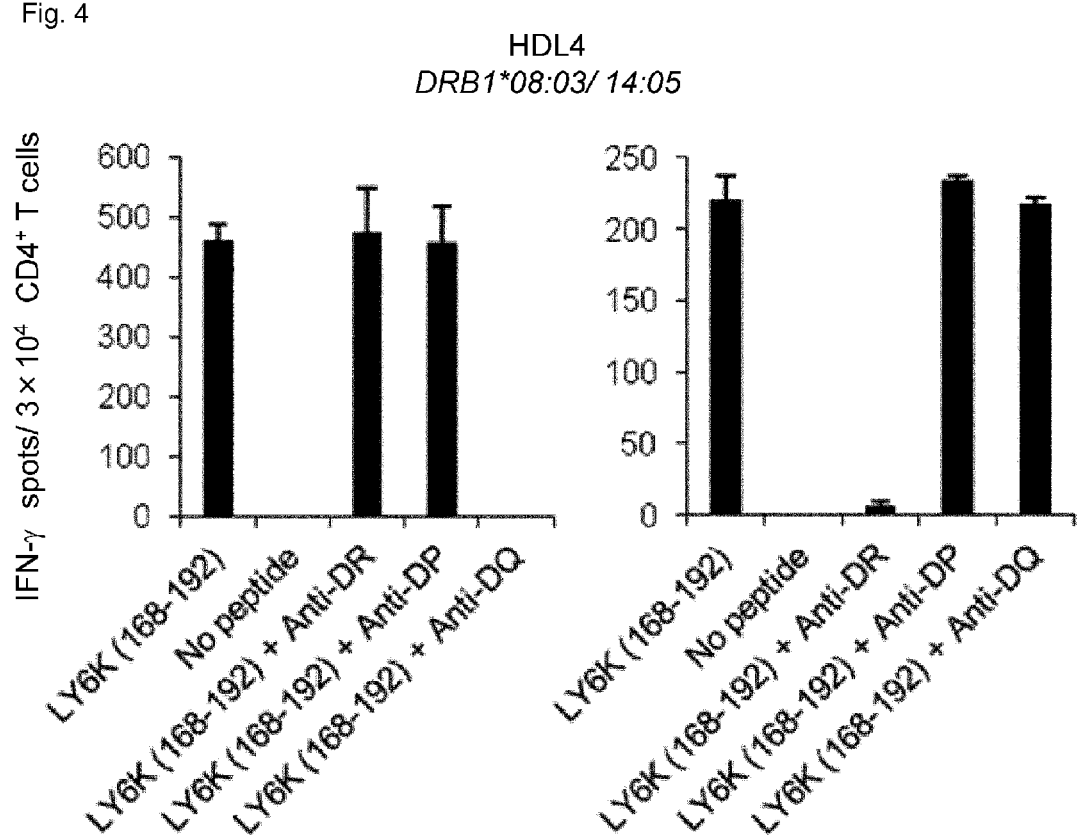

FIG. 4 presents the induction of LY6K (168-192)-specific CD4+ T cells by stimulation of peripheral CD4+ T cells with LY6K (168-192) peptide and identification of antigen-presenting HLA-class II molecules. CD4+ T cell lines were generated from a healthy donor-HDL4. After at least 3 rounds of stimulation of peripheral CD4+ T cells with LY6K (168-192), the number of IFN-gamma-producing CD4+ T cells was analyzed by ELISPOT assay. Responses against LY6K (168-192) are shown for an HLA-DR8 (DRB1*08: 03) and -DR14 (DRB1*14:05)-positive healthy donor. The CD4+ T cells were stimulated with autologous PBMC alone (no peptide), PBMC pulsed with LY6K (168-192) (10 micro-g/ml), or PBMC pulsed with LY6K (168-192) in the presence of 5 micro-g/ml of mAb specific to HLA-DR, DP or DQ.

FIG. 5 presents the functional characterization of bulk LY6K (119-142)-specific CD4+ Th cell line or a LY6K (172-191) LP-specific Th-clone. In Part A, after 20 h incubation period of T cells ($1\times10^4$) cocultured with LY6K (119-142)-pulsed L-DP5 ($5\times10^4$), the culture supernatants were collected and the concentration of cytokines (IFN-gamma, TNF-alpha, GM-CSF, MIP1beta, IL-2, IL-4 and IL-7) were measured using Bio-Plex assay system. Data are presented as the mean+/−SD of triplicate assays.

FIG. 5A2 is a continuation of FIG. 5A1.

In Part B, after 24 h incubation of autologous PBMCs (for HLA-DQ-restricted LY6K (172-191) LP-specific Th-clone) in the presence of cognate peptides, the culture supernatant was collected and the concentration of cytokines (IFN-gamma, TNF-alpha, IL-2, GM-CSF, and MIP1beta) was measured using the Bio-Plex assay system. Data are presented as the mean+/−SD of triplicate assays.

Part C depicts the detection of CD107a exposed on the cell surface of CD4+ T cells after antigenic stimulation. In Upper panels, cells were restimulated with LY6K (119-142) LP or an irrelevant peptide. The numbers inside the plots indicate the percentage of the cell population with the quadrant characteristic (CD4+ CD107a+ T cells). In Lower panels, cells were restimulated with LY6K (172-191) LP or an irrelevant peptide. The numbers inside the plots indicate the percentage of the cell population with the quadrant characteristic (CD4+ CD107a+ T cells).

FIG. 6 presents the LY6K (172-191) LP inducing an expansion of LY6K-A24 (177-186) SP-specific CD8+ T cells in vitro and in vivo. In Part A, PBMCs ($2\times10^6$/well) were incubated with LY6K (172-191) LP (7 micro-M) for 2 weeks without addition of any cytokine. On days 0 and 7, LY6K (172-191) LP were added, then on day 14 of in vitro stimulation with LP peptide, the cells were harvested, stained with a PE-labeled tetramer of the HLA-A24 (A*24: 02)/LY6K-A24 (177-186) peptide complex in combination with a FITC-labeled anti-human CD8 mAb, and analyzed by flow cytometry. Dots in the upper right quadrant represent CD8+ tetramer+ T cells. Events shown are gated for CD8+ T cells. The numbers inside the plots indicate the percentage of the cell population with the upper right quadrant characteristic (CD8+ tetramer+ T cells). Data are a representative of 2 independent experiments with similar results from a HLA-A24-positive healthy donor. Part B presents that the LY6K (172-191) LP induces an in vitro expansion of antigen-specific CD8+ T cells derived from a head and neck cancer patient vaccinated with LY6K-A24 (177-186) SP. LY6K-A24 (177-186) SP specific-CTL in PBMC isolated from a patient who was actively immunized with LY6K-A24 (177-186) SP was detected by a PE-labeled tetramer of the HLA-A24 (A*24:02)/LY6K-A24 (177-186)-complex ex-vivo. After short term (one week) stimulation of PBMCs with LY6K (172-191) LP, the PBMC was collected and then the LY6K-A24 (177-186) SP-specific CTL was also detected by the tetramer.

Part C depicts the expansion of LY6K-A24 (177-186) SP-specific CTLs in HLA-A24 Tgm immunized with LY6K (172-191) LP. HLA-A24 Tgm were immunized at the base of the tail with LY6K (172-191) LP emulsified in IFA. Seven days after the second vaccinations with LY6K (172-191) LP, CD8+ T cells in inguinal lymph nodes were positively isolated and cocultured with C1R-A2402 cells pulsed with LY6K-A24 (177-186) SP or irrelevant peptide, and the number of IFN-gamma-producing CD8+ T cells was analyzed by an ex vivo ELISPOT assay. Representative data from 3 independent experiments with similar results are shown.

FIG. 7 presents the presence of LY6K long peptide-specific T cells in PBMCs isolated from head and neck cancer patients vaccinated with a LY6K-A24 (177-186) short peptide. In Part A, the LY6K-specific-T cell responses were assessed in 6 head and neck cancer patients vaccinated with a LY6K-A24 (177-186) short peptide, a non-vaccinated patient and 3 healthy donors as controls. After short term stimulation (one week) with a mixture of LY6K (119-142) LP and LY6K (172-191) LP, the frequency of individual LY6K-specific T cells was detected using IFN-gamma ELISPOT assay. The results represented specific IFN-gamma spots after subtraction of background. Responses were considered to be positive when IFN-gamma spots were more than 10 and more than 2-fold the background. The lines within each group of plots show the median. Part B demonstrates the HLA-restriction of the IFN-gamma-producing T cells. The PBMCs stimulated with LPs for one week were restimulated with each peptide (10 micro-g/ml) in the presence of 5 micro-g/ml of mAb specific to HLA-DR, -DP or HLA-class I. The numbers of IFN-gamma-producing Th cells were analyzed by an ELISPOT assay. The results represented specific IFN-gamma spots after subtraction of background. Representative data from three independent experiments from three cancer patients with similar results are shown.

FIG. 8 presents the presence of LY6K-LPs-specific Th cells in PBMCs obtained from HNMT patients. In Part A, after in vitro stimulation of PBMCs with a mixture of LY6K (119-142) LP and LY6K (172-191) LP for 1 week, the frequency of LY6K-LP-specific T-cells was detected by IFN-gamma ELISPOT assay.

Part B presents HLA class II-restriction of LY6K-LP-specific Th cells. Fresh PBMCs stimulated with LY6K-LPs for 1 week were restimulated with each LY6K-LP in the presence of mAbs specific to HLA-DR, -DP, -DQ, or HLA-class I. LY6K-LP-specific IFN-gamma production by Th cells was significantly inhibited by addition of the anti-HLA-class II mAbs, but not by the anti-HLA-class I mAb in 7 HNMT patients (LY6K (119-142) LP, HNMT31, 41, 107; LY6K (172-191) LP, HNMT26, 31, 41, 42 103, 107, 108).

FIG. 8B2 is a continuation of FIG. 8B1.

In Part C, HNMT patients demonstrate elevated LY6K-LP-specific Th cell immunity compared to normal healthy individuals. Colom graph showing proportion of patients and healthy donors (control) responded to LY6K (119-142) LP or LY6K (172-191) LP. p values were calculated using Fisher's exact probability test. In Part D, LY6K-LP-specific-Th cell responses were assessed in 23 HNMT patients. 20 HNMT patients vaccinated with LY6K-A24 (177-186) SP (After Vac.), 11 HNMT patients (Before Vac.), and 9 healthy donors (control) were tested. The results represent specific IFN-gamma spots after background subtraction. Each dot represents an individual donor. Horizontal lines denote median values, and p values represent statistical results from a nonparametric Mann-Whitney U test. n.s., not significant.

Parts E-G present the presence of LY6K-LPs-specific Th cells in PBMCs obtained from HNMT patients before and after vaccination. After in vitro stimulation of PBMCs with a mixture of LY6K (119-142) LP and LY6K (172-191) LP for 1 week, the frequency of LY6K-LP-specific T-cells was detected by IFN-gamma ELISPOT assay. In Part E, HNMT patients after vaccination showed elevated LY6K-LP-specific Th cell immunity compared to normal healthy individuals. The frequency of LY6K (172-191) LP-specific immune response in HNMT patients after vaccination was significantly higher than those in HNMT patient before vaccination. Colom graph showing proportion of patients and healthy donors (control) responded to LY6K (119-142) LP or LY6K (172-191) LP. p values were calculated using Fisher's exact probability test.

In Part F, the repeated CTL-epitope peptide vaccinations augmented or elicited LY6K (119-142) LP (black bars) and LY6K (172-191) LP (white bars)-specific Th cell responses.

Part G depicts a comparison of the numbers of LY6K-LP-specific IFN-gamma spots between vaccinated HNMT patients with advanced cancer (CTR-8379, Advanced, n=13) and vaccinated HNMT patients receiving postoperative adjuvant immunotherapy (CTR-8380, Postoperative, n=8). After 1-week in vitro stimulation of PBMCs with a mixture of LY6K (119-142) LP and LY6K (172-191) LP, the frequency of individual LY6K-LP-specific Th cells was detected by IFN-gamma ELISPOT assay. The results represent specific IFN-gamma spots after background subtraction. Each dot represents an individual donor. Horizontal lines denote median values, and p values represent statistical results from a nonparametric Mann-Whitney U test. n.s., not significant.

FIG. 9 presents that LY6K-LPs encompass naturally processed Th cell epitopes. Part A demonstrates that HLA-DP5-restricted LY6K (119-142) LP-specific bulk Th cells established from HDL1 specifically recognized autologous DCs loaded with recombinant LY6K protein. Representative data from 3 independent experiments with similar results are shown. Part B demonstrates that HLA-DR15 (left, HDL2) or HLA-DQ (right, HDL4)-restricted LY6K (172-191) LP-specific Th-clone recognized autologous DCs loaded with a recombinant LY6K protein. Representative data from 5 independent experiments with similar results are shown. Cognate LY6K-LPs were used as positive controls in IFN-gamma ELISPOT assays.

FIG. 10 presents that LY6K (172-191) LP induces efficient expansion of LY6K-A24 (177-186) SP-specific $CD8^+$ T-cells in vitro and in vivo. Part A depicts the uptake and cross-presentation of LY6K (172-191) LP by DCs. Unfixed or fixed DCs were pulsed for 3 h with LY6K (172-191) LP or LY6K-A24 (177-186) SP. The bulk LY6K-A24 (177-186) SP-specific CTLs generated from HDL3 were co-cultured for 6 h and responses were measured by IFN-gamma labeling. Representative data from 3 independent experiments with similar results are shown. Part B demonstrates that LY6K (172-191) LP induces efficient expansion of LY6K-A24 (177-186) SP-specific $CD8^+$ T-cells in vitro. LY6K-A24 (177-186) SP-specific bulk CTLs established from HDL3 (HLA-A24$^+$ and DR15$^+$) were stimulated with LY6K (172-191) LP (middle panel) or irrelevant LP (right panel)-pulsed autologous DCs in vitro. Before LP-stimulation (day 0; left panel) and on days 7 after LP-stimulation, an aliquot of cultured cells ($1 \times 10^5$ cells) was stained with a LY6K-A24 (177-186) SP-specific tetramer in combination with an anti-human CD8 mAb. Representative data on day 0 and day 7 from 3 independent experiments with similar results are shown. Events are gated for $CD8^+$ T-cells.

Part C demonstrates that LY6K (172-191) LP induces in vitro expansion of LY6K-A24 (177-186) SP-specific CTLs in HNMT patients. Fresh PBMCs from the HNMT patient (HNMT108) vaccinated with LY6K-A24 (177-186) SP were cultured with LY6K (172-191) LP. On day 0 (ex vivo) and day 7, the PBMCs were stained with a tetramer HLA-A*24:02/LY6K-A24 (177-186) complex or control tetramer. (gated on $CD8^+$ T-cells; dot plot). On day 7, the frequency of LY6K-A24 (177-186) SP-specific CTLs was also detected by IFN-gamma ELISPOT assay (bar graph). Representative data from 4 vaccinated HNMT patients (Table 1, HNMT43, 105, 108, and 110) with similar results are shown.

In Part D, the increases (fold increase) in proportion of $CD8^+$ tetramer$^+$ cells are shown.

Parts E-G demonstrate that LY6K-LPs induce in vitro expansion of LY6K-A24 (177-186) SP-specific CTLs in HNMT patients. In Part E, fresh PBMCs from the HNMT patient (HNMT29) vaccinated with LY6K-A24 (177-186) SP were cultured with a mixture of LY6K (119-142) LP and LY6K (172-191) LP. On day 0 (ex vivo) and day 7 (after in vitro stimulation with LY6K-LPs), the PBMCs were stained with a tetramer HLA-A*24:02/LY6K-A24 (177-186) complex (gated on CD8+ T-cells). On day 7, the frequency of LY6K-A24 (177-186)-specific CTLs was also detected by IFN-gamma ELISPOT assay (bar graph). Detailed methods are provided in Supplemental Materials and Methods. Representative data from 9 vaccinated HNMT patients (HNMT20, 26, 29, 31, 34, 39, 41, 102, and 108) with similar results are shown.

In Part F, the increases (fold increase) in proportion of CD8+ tetramer+ cells are shown.

In Part G, fresh PBMCs from an HNMT patient before vaccination (HNMT42) were stimulated with a mixture of LY6K-LPs. Part H demonstrates that LY6K (172-191) LP induces efficient cross-priming of CTLs in vitro. PBMCs obtained from HDL3 were incubated with LY6K (172-191) LP for 2 weeks. On days 0 and 7, LY6K (172-191) LP was added, and then on day 14, the cells were harvested and stained with a LY6K-A24 (177-186) SP-specific tetramer. Representative data from three independent experiments with similar results are shown. Similar results were also obtained from HDL1 and HDL4.

Part I presents the induction of LY6K-A24 (177-186) SP-specific CTLs in mice immunized with LY6K (172-191) LP. HLA-A24 Tgm were immunized with LY6K (172-191) LP. After the third vaccination with LY6K (172-191) LP, murine CD8+ T-cells in the inguinal lymph nodes were stimulated with BM-DC (bone marrow-derived DC) pulsed with LY6K-A24 (177-186) SP. The number of IFN-gamma-producing murine CD8+ T-cells was analyzed by ex vivo ELISPOT. Representative data from 8 independent experiments with similar results are shown.

FIG. 11 presents the synergistic effect of LY6K-LPs on induction of LY6K-A24 (177-186) SP-specific CTLs. Part A demonstrates the enhanced induction of LY6K-A24 (177-186) SP-specific CTLs by activated bulk LY6K-LP-specific CD4+ T-cells. LY6K (119-142) LP-specific or LY6K (172-191) LP-specific bulk CD4+ T-cells and LY6K-A24 (177-186) SP-specific bulk CD8+ T-cells derived from HLA-A24+/DR15+ HDL3 were cultured with autologous DCs in the presence of LY6K-A24 (177-186) SP (SP) alone, LY6K-A24 (177-186) SP+Control LP (Control LP+SP), or LY6K-A24 (177-186) SP+LY6K-LP (LY6K-LP+SP) without addition of any cytokine. After 1-week in vitro culture with peptides, the cultured cells were stained with PE-labeled tetramer of the HLA-A*24:02/LY6K-A24 (177-186) complex and FITC-labeled anti-human CD8 mAb. The results of cells cultured without any peptide were also shown (No peptide). The column of pre-stimulation indicate the absolute number of tetramer+ CD8+ T-cells/well of LY6K-A24 (177-186) SP-specific bulk CD8+ T-cells line used in this experiment. Data are presented as the mean+/−SD of triplicate assays (bar graph). Representative data from 3 independent experiments with similar results are shown.

Part B demonstrates the synergistic effect of LY6K-LP on induction of LY6K-specific CTLs. Fresh PBMCs obtained from HNMT43 vaccinated with LY6K-A24 (177-186) SP were plated in a 96-well, round-bottomed culture plate (1×10⁵ cells/well), followed by addition of LY6K-A24 (177-186) SP alone (10 micro-g/mL), LY6K-A24 (177-186) SP+control LP (10 micro-g/mL), LY6K-A24 (177-186) SP+LY6K (119-142) LP (10 micro-g/mL), or LY6K-A24 (177-186) SP+LY6K (172-191) LP (10 micro-g/mL) without addition of cytokines. On day 7 of culture, cells were stained with a LY6K-A24 (177-186)-specific tetramer. Representative LY6K-A24 (177-186) SP-specific tetramer staining is shown (gated on CD8+ T-cells, dot plots).

Part C depicts the colom graph showing absolute number of tetramer+ CD8+ cells/well. Data are presented as the mean+/−SD of triplicate assays. Representative data from 3 independent experiments with similar results are shown.

In part D, fresh PBMCs obtained from two vaccinated HNMT patients (Upper panel, HMNT42; Lower panel, HNMT31) were cultured for 7 days with LY6K-A24 (177-186) SP (SP) or SP+LY6K-LP (SP+LP). Representative LY6K-A24 (177-186) SP-specific tetramer staining (gated on CD8+ T-cells) obtained from duplicate wells with similar results is shown.

FIG. 12 presents the clinical characteristics of HNMT patients. LY6K-specific T-cell responses measured by IFN-gamma ELISPOT assay as detailed in the Materials and Methods section. Positive and negative responses are denoted by (+) and (−), respectively. No., Number; CTR, Clinical Trials Registry; vac., vaccination; HNMT, Head-and-neck malignant tumor; M/F, male/female; LP, long peptide; n.t., not tested

DESCRIPTION OF EMBODIMENTS

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

I. Definitions

Unless otherwise defined, all technical and scientific terms used herein have the same meaning as commonly understood by one of ordinary skill in the art to which the present invention belongs. However, in case of conflict, the present specification, including definitions, will control.

The words "a", "an", and "the" as used herein mean "at least one" unless otherwise specifically indicated.

The terms "isolated" and "purified" used in relation with a substance (e.g., peptide, antibody, polynucleotide, etc.) indicates that the substance is substantially free from at least one substance that may else be included in the natural source. Thus, an isolated or purified peptide refers to peptide that are substantially free of cellular material such as carbohydrate, lipid, or other contaminating proteins from the cell or tissue source from which the peptide is derived, or substantially free of chemical precursors or other chemicals when chemically synthesized. The term "substantially free of cellular material" includes preparations of a peptide in which the peptide is separated from cellular components of the cells from which it is isolated or recombinantly produced. Thus, a peptide that is substantially free of cellular material includes preparations of polypeptide having less than about 30%, 20%, 10%, or 5% (by dry weight) of heterologous protein (also referred to herein as a "contaminating protein"). When the peptide is recombinantly produced, it is also preferably substantially free of culture medium, which includes preparations of peptide with culture medium less than about 20%, 10%, or 5% of the volume of the peptide preparation. When the peptide is produced by chemical synthesis, it is preferably substantially free of chemical precursors or other chemicals, which includes preparations of peptide with chemical precursors or other chemicals involved in the synthesis of the peptide less than about 30%, 20%, 10%, 5% (by dry weight) of the volume of the peptide preparation. That a particular peptide preparation contains an isolated or purified peptide can be shown, for example, by the appearance of a single band following sodium dodecyl sulfate (SDS)-polyacrylamide gel electrophoresis of the protein preparation and Coomassie Brilliant Blue staining or the like of the gel. In a preferred embodiment, peptides and polynucleotides of the present invention are isolated or purified.

The terms "polypeptide", "peptide" and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "amino acid" as used herein refers to naturally occurring and synthetic amino acids, as well as amino acid analogs and amino acid mimetics that similarly function to the naturally occurring amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotide" and "nucleic acid" are used interchangeably herein and, unless otherwise specifically indicated, are referred to by their commonly accepted single-letter codes. The terms "agent" and "composition" are used interchangeably herein to refer to a product that includes specified ingredients in specified amounts, as well as any product that results, directly or indirectly, from combination of the specified ingredients in the specified amounts. Such term in relation to pharmaceutical composition, is intended to encompass a product including the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically or physiologically acceptable carrier.

The term "active ingredient" herein refers to a substance in a composition that is biologically or physiologically active. Particularly, in the context of a pharmaceutical composition, the term "active ingredient" refers to a component substance that shows an objective pharmacological effect. For example, in case of pharmaceutical compositions for use in the treatment or prevention of cancer, active ingredients in the compositions may lead to at least one biological or physiological action on cancer cells and/or tissues directly or indirectly. Preferably, such action may include reducing or inhibiting cancer cell growth, damaging or killing cancer cells and/or tissues, and so on. Typically, indirect effect of active ingredients is inductions of immune responses mediated by MHC Class II molecules. Before being formulated, the "active ingredient" may also be referred to as "bulk", "drug substance" or "technical product". The phrase "pharmaceutically acceptable carrier" or "physiologically acceptable carrier", as used herein, means a pharmaceutically or physiologically acceptable material, composition, substance or vehicle, including, but are not limited to, a liquid or solid filler, diluent, excipient, solvent or encapsulating material.

Unless otherwise defined, the term "cancer" refers to cancers overexpressing LY6K gene, including, for example, bladder cancer, cervical cancer, cholangiocellular carcinoma, esophageal cancer, gastric cancer, non-small cell lung cancer (NSCLC), osteosarcoma, pancreatic cancer, soft tissue tumor and head-and-neck malignant tumor (HNMT). Unless otherwise defined, the terms "head-and-neck malignant tumor (HNMT)" and "head and neck cancer" are used interchangeably herein Unless otherwise defined, the terms "T lymphocyte" and "T cell" are used interchangeably herein.

Unless otherwise defined, the term "cytotoxic T lymphocyte", "cytotoxic T cell" and "CTL" are used interchangeably herein and, otherwise specifically indicated, refer to a sub-group of T lymphocytes that are capable of recognizing non-self cells (e.g., tumor cells, virus-infected cells) and inducing the death of such cells. CTLs are differentiated from $CD8^+$ T lymphocytes and can recognize peptides presented by MHC class I molecules.

Unless otherwise defined, the terms "HLA-A24" refers to the HLA-A24 type containing the subtypes, examples of which include, but are not limited to, HLA-A*2401, HLA-A*2402, HLA-A*2403, HLA-A*2404, HLA-A*2407, HLA-A*2408, HLA-A*2420, HLA-A*2425 and HLA-A*2488.

Unless otherwise defined, "HLA-A2", as used herein, representatively refers to the subtypes, examples of which include, but are not limited to, HLA-A*0201, HLA-A*0202, HLA-A*0203, HLA-A*0204, HLA-A*0205, HLA-A*0206, HLA-A*0207, HLA-A*0210, HLA-A*0211, HLA-A*0213, HLA-A*0216, HLA-A*0218, HLA-A*0219, HLA-A*0228 and HLA-A*0250.

Unless otherwise defined, the terms "T helper type 1 cell" and "Th1 cell" are used interchangeably herein and, otherwise specifically indicated, refer to a sub-group of $CD4^+$ T lymphocytes that are capable of recognizing peptides presented by an MHC class II molecules, and associated with cellular immunity. Unless otherwise defined, the terms "Th cell", "$CD4^+$ T cell" and "$CD4^+$ helper T cell" are also used interchangeably herein. Th1 cells secrete a variety of cytokines (such as IFN-gamma, IL-2, TNF-beta, GM-CSF, TNF-alpha, and so on) to help activation and/or stimulation of other immune cells relating to cellular immunity (e.g., CTL, macrophage).

Unless otherwise defined, the terms "HLA-DR4" refers to the subtypes, examples of which include, but are not limited to, HLA-DRB1*04:01, HLA-DRB1*04:02, HLA-DRB1*04:03, LA-DRB1*04:04, HLA-DRB1*04:05, HLA-DRB1*04:06, HLA-DRB1*04:07, HLA-DRB1*04:08, HLA-DRB1*04:09, HLA-DRB1*04:10 and HLA-DRB1*04:11.

Unless otherwise defined, the terms "HLA-DR8" refers to the subtypes, examples of which include, but are not limited to, HLA-DRB1*08:01, HLA-DRB1*08:02, HLA-DRB1*08:03, LA-DRB1*08:04, HLA-DRB1*08:05, HLA-DRB1*08:06, HLA-DRB1*08:07, HLA-DRB1*08:10, HLA-DRB1*08:11 and HLA-DRB1*08:12.

Unless otherwise defined, the term "HLA-DR9" refers to the subtypes, examples of which include, but are not limited to, HLA-DRB1*09:01, HLA-DRB1*09:02, HLA-DRB1*09:03, LA-DRB1*09:04, HLA-DRB1*09:05, HLA-DRB1*09:06, HLA-DRB1*09:07, HLA-DRB1*09:08 and HLA-DRB1*09:09.

Unless otherwise defined, the term "HLA-DR15" refers to the subtypes, examples of which include, but are not limited to, HLA-DRB1*15:01, HLA-DRB1*15:02, HLA-DRB1*15:03, LA-DRB1*15:04, HLA-DRB1*15:05, HLA-DRB1*15:06, HLA-DRB1*15:07, HLA-DRB1*15:08, HLA-DRB1*15:09, HLA-DRB1*15:10 and HLA-DRB1*15:11.

Unless otherwise defined, the term "HLA-DP2" refers to the subtypes, examples of which include, but are not limited to, HLA-DPB1*0201 and HLA-DPB1*02:02.

Unless otherwise defined, the term "HLA-DP5" refers to the subtypes, examples of which include, but are not limited to, HLA-DPB1*0501.

Unless otherwise defined, the phrase "immune response mediated with an MHC class II molecule" refers to immune responses induced by presentation of peptide by MHC class II molecule. Herein, "immune response mediated with an MHC class II antigen" includes immune responses induced by CD4$^+$ T cells, in particular, Th1 cells. Examples of such immune responses include, but not limited to, production of cytokines (such as IFN-gamma, IL-2, TNF-beta, GM-CSF, TNF-alpha, and so on) and activation and/or stimulation of other immune cells (such as CTL, macrophage, and so on).

Unless otherwise defined, the phrase "Th1 cell specific to LY6K" refers to a Th1 cell that is specifically activated with an antigen presenting cell presenting a peptide derived from LY6K, but not with other antigen presenting cells.

Unless otherwise defined, the phrase "LY6K-specific CTL" refers to a CTL that specifically shows cytotoxicity against a target cell expressing LY6K.

Unless otherwise defined, when used in the context of peptides, the phrase "CTL inducibility" refers to an ability of a peptide to induce a CTL when presented on an antigen-presenting cell.

Unless otherwise defined, the term "kit" as used herein, is used in reference to a combination of reagents and other materials. It is contemplated herein that the kit may include microarray, chip, marker, and so on. It is not intended that the term "kit" be limited to a particular combination of reagents and/or materials.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an antibody herein is used in the broadest sense and specifically covers intact monoclonal antibodies, polyclonal antibodies, multispecific antibodies (e.g., bispecific antibodies) formed from at least two intact antibodies, and antibody fragments so long as they exhibit the desired biological activity. An "antibody" indicates all classes (e.g., IgA, IgD, IgE, IgG and IgM).

Unless otherwise defined, all technical and scientific terms used herein have the same meaning as commonly understood by one of ordinary skill in the art to which this invention belongs.

II. Peptides

Peptides of the present invention described in detail below may be referred to as "LY6K peptide(s)" or "LY6K polypeptide(s)".

To demonstrate that peptides derived from LY6K function as an antigen recognized by T helper type 1 (Th1) cells, peptides derived from LY6K (SEQ ID NO: 8) were analyzed to determine whether they were antigen epitopes promiscuously restricted by MHC class II molecules. Candidates of promiscuous MHC class II binding peptides derived from LY6K were identified based on their binding affinities to HLA-DP5, HLA-DR15, HLA-DR8 and one or several HLA-DQs. After in vitro stimulation of CD 4$^+$ T-cells by dendritic cells (DCs) loaded with these peptides, Th1 cells were successfully established using each of the following peptides:

```
                                              (SEQ ID NO: 1)
LY6K (119-142)/KWTEPYCVIAAVKIFPRFFMVAKQ,
and (SEQ ID NO: 2)
LY6K (172-191)/KCCKIRYCNLEGPPINSSVF.
```

These established Th1 cells noted above showed potent specific Th1 cell activity in response to stimulation of antigen presenting cells pulsed with respective peptides. Furthermore, the aforementioned peptides could stimulate Th1 cells restricted by several HLA-DR, HLA-DP and HLA-DQ molecules (e.g., HLA-DP5, HL-DR15, HLA-DR8) which are frequently observed in the Japanese population. These results demonstrate that LY6K is an antigen recognized by Th1 cells and that the peptides are epitope peptides of LY6K promiscuously restricted by several HLA-class II molecules (such as HLA-DP5, HLA-DR15, HLA-DR8, and one or several HLA-DQs); accordingly, such peptides may be effective as target antigens for cytotoxicity by CTLs.

The above-identified peptides additionally contained an amino acid sequence of a CTL epitope having an ability to induce a CTL specific to LY6K and, as demonstrated herein, such peptides can induce CTLs specific to LY6K as well as Th1 cells. Accordingly, those peptides may be suitable peptides for induction of immune responses against cancer expressing LY6K. Since the LY6K gene is over-expressed in most cancer tissues, including, for example, bladder cancer, cervical cancer, cholangiocellular carcinoma, esophageal cancer, gastric cancer, non-small cell lung cancer (NSCLC), osteosarcoma, pancreatic cancer, soft tissue tumor and head- and neck malignant tumor (HNMT), it represents a good target for immunotherapy.

Accordingly, the present invention provides peptides having ability induce Th1 cells specific to LY6K. The peptides of the present invention can bind at least one MHC class II molecule and be presented on antigen presenting cells. Alternatively, the fragment of the peptides of the present invention may bind at least one MHC class II molecule and be presented on antigen presenting cells. Those fragments of the peptides may be produced by processing within antigen presenting cells. In preferred embodiments, the peptides of the present invention or fragment thereof have abilities to bind two or more kinds of MHC class II molecules (e.g., HLA-DP5 and HLA-DR15, HLA-DR8 and HLA-DR15, HLA-DP5 and HLA-DR8, HLA-DR15 and one of HLA-DQs, or HLA-DP5, HLA-DR15 and HLA-DR8,). In other words, the peptides of the present invention may have an ability to induce Th1 cells that are restricted by two or more kinds of MHC class II molecules. In another embodiment, the peptides of the present invention include an amino acid sequence of a peptide having LY6K-specific CTL inducibility. The typical examples of such peptides having LY6K-specific CTL inducibility include peptides having an amino acid sequence of SEQ ID NO: 3.

Since the binding groove in an MHC class II molecule is open at both ends, MHC class II binding peptides are allowed to have flexibility in their length. The core binding motif for MHC class II molecule is composed of 9 amino acid residues, and MHC class II binding peptides generally have other amino acid residues flanking with the core binding motif. The number of flanking amino acid residues is not restricted. Thus, all amino acid residues of SEQ ID NO: 1 or 2 are not indispensable for binding an MHC class II molecule. Accordingly, the peptide of the present invention can be a peptide having ability to induce a Th1 cell, such peptide including an amino acid sequence selected from the group consisting of:

(a) an amino acid sequence having more than 9 contiguous amino acids from the amino acid sequence of SEQ ID NO: 1 or 2; and (b) an amino acid sequence of (a) in which one, two or several amino acids are substituted, deleted, inserted, and/or added.

The length of an MHC class II binding peptides is generally 10-30 amino acids. In that the amino acid sequences of SEQ ID NO: 1 and 2 are composed of a part of the amino acid sequence of LY6K (SEQ ID NO: 8) the peptides of the present invention can be a following peptide of [1] to [6]:

[1] An isolated peptide having 10-30 amino acids in length and including a part of the amino acid sequence of SEQ ID NO: 8, wherein such peptide comprises an amino acid sequence selected from the group consisting of:

(a) a contiguous amino acid sequence having more than 9 amino acids in length selected from the amino acid sequence of SEQ ID NO: 1 or 2; and (b) an amino acid sequence of (a) in which one, two or several amino acids are substituted, deleted, inserted, and/or added, wherein such peptide has ability to induce Th1 cell(s);

[2] The isolated peptide of [1], wherein the peptide or fragment thereof has abilities to bind at least two kinds of MHC class II molecules;

[3] The isolated peptide of [2], wherein the MHC class II molecules are selected from the group consisting of HLA-DP5, DR15, DR8 and one of HLA-DQs;

[4] The isolated peptide of any one of [1] to [3], wherein said peptide comprises an amino acid sequence of a peptide having LY6K-specific cytotoxic T lymphocyte (CTL) inducibility; and

[5] The isolated peptide of [4], wherein said peptide comprises the amino acid sequence selected from the group consisting of:

(a) an amino acid sequence selected from the group consisting of SEQ ID NOs: 1 and 2;

(b) an amino acid sequence of (a) in which one, two or several amino acids are substituted, deleted, inserted, and/or added; and

[6] The isolated peptide of [5], wherein the peptide comprises the amino acid sequence of SEQ ID NO: 6.

Th1 cells induced by the peptide of the present invention are specific to LY6K.

Therefore, in some embodiments, the present invention provides peptides of less than 30 amino acid residues consisting of a partial amino acid sequence of the amino acid sequence of SEQ ID NO: 8, wherein the peptides comprise the amino acid sequence of SEQ ID NO: 1 or 2.

Generally, software programs presently available on the Internet, such as those described in Wang P et al. 2008. PLoS Comput Biol. 4(4):e1000048. 11:568; and Wang P et al. 2010. BMC Bioinformatics. can be used to calculate the binding affinities between various peptides and HLA antigens in silico. Binding affinity with HLA antigens can be measured as described, for example, in Nielsen M and Lund O. 2009. BMC Bioinformatics. 10:296.; Nielsen M et al. 2007. BMC Bioinformatics. 8:238. Bui H H, et al. 2005. Immunogenetics. 57:304-314. Sturniolo T et al. 1999. Nat Biotechnol. 17(6):555-561 and Nielsen M et al. 2008. PLoS Comput Biol. 4(7)e1000107. Thus, the present invention encompasses peptides of LY6K which are determined to bind with HLA antigens identified using such known programs.

As described above, since MHC class II binding peptides have flexibility in their length, the amino acid sequence of SEQ ID NO: 1 or 2 can be optionally flanked with additional amino acid residues so long as the resulting peptide retains the requisite Th1 cell inducibility. Such peptides having Th1 cell inducibility are typically, less than about 30 amino acids, often less than about 29 amino acids, and usually less than about 28 or 27 amino acids. The particular amino acid sequence(s) flanking the amino acid sequence selected from among SEQ ID NOs: 1 and 2 are not limited and can be composed of any kind of amino acids, so long as such flanking amino acid sequences do not impair the Th1 cell inducibility of the original peptide. In typical embodiments, such flanking amino acid sequence(s) may be selected from among the amino acid sequence of SEQ ID NO: 8 adjacent to the amino acid sequence of SEQ ID NO: 1 or 2; however, the present invention is not limited thereto. As such, the present invention also provides peptides having Th1 cell inducibility and an amino acid sequence selected from among SEQ ID NOs: 1 and 2.

On the other hand, since a core binding motif for an MHC class II molecule is composed of 9 amino acid residues, the full length of the amino acid sequence of SEQ ID NO: 1 or 2 is not indispensable for binding an MHC class II molecule and induction of Th1 cells. Thus, a peptide of the present invention can take the form of an amino acid having more than 9 contiguous amino acids of SEQ ID NO: 1 or 2, provided said peptide retains the requisite Th1 cell inducibility. Peptides having Th1 cell inducibility are typically, more than about 10 amino acids, often more than 11 or 12 amino acids, and usually more than 13 or 14 amino acids. Accordingly, the peptides of the present invention can be peptides having Th1 cell inducibility and an amino acid sequence having more than 9, 10, 11, 12, 13 or 14 contiguous amino acids from the amino acid sequence of SEQ ID NO: 1 or 2.

It is generally known that the modification of one, two, or more amino acids in a protein will not influence the function of the protein, and in some cases will even enhance the desired function of the original protein. In fact, modified peptides (i.e., peptides composed of an amino acid sequence in which one, two or several amino acid residues have been modified (i.e., substituted, added, deleted or inserted) as compared to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention may have both Th1 cell inducibility and an amino acid sequence selected from among SEQ ID NO: 1 and 2, wherein one, two or even more amino acids are added, inserted, deleted and/or substituted. Alternatively, the peptides of the present invention may have both of Th1 cell inducibility and an amino acid sequence in which one, two or several amino acids are added, inserted, deleted and/or substituted in the amino acid sequence of SEQ ID NO: 1 or 2.

Those of skilled in the art recognize that individual additions or substitutions to an amino acid sequence which alter a single amino acid or a small percentage of amino acids tend to result in the conservation of the properties of the original amino acid side-chain. As such, they are often referred to as "conservative substitutions" or "conservative modifications", wherein the alteration of a protein results in a modified protein having a function analogous to the original protein. Conservative substitution tables providing functionally similar amino acids are well known in the art. Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be the peptides of the present invention. However, the peptides of the present invention are not restricted thereto and can include non-conservative modifications, so long as the modified peptide retains the Th1 cell inducibility of the original peptide. Furthermore, modified peptides should not exclude Th1 cell inducible peptides of polymorphic variants, interspecies homologues, and alleles of LY6K.

To retain the requisite Th1 cell inducibility, one can modify (insert, add, deletion and/or substitute) a small number (for example, 1, 2 or several) or a small percentage of amino acids. Herein, the term "several" means 5 or fewer amino acids, for example, 4 or 3 or fewer. The percentage of amino acids to be modified is preferably 20% or less, more preferably, 15% of less, even more preferably 10% or 8%, less or 1 to 5%.

Homology analysis of preferred peptides of the present invention, namely SEQ ID NOs: 1 and 2 (LY6K 119-142, 172-191), confirm that these peptides do not have significant homology with peptides derived from any other known human gene products. Thus, the possibility of these peptides generating unknown or undesired immune responses when used for immunotherapy is significantly lowered. Accordingly, these peptides are expected to be highly useful for eliciting immunity in cancer patients against LY6K.

When used in the context of immunotherapy, the peptides of the present invention or fragment thereof should be presented on the surface of an antigen presenting cell, preferably as a complex with an HLA class II antigen. Therefore, it is preferable to select peptides that not only induce Th1 cells but also possess high binding affinity to the HLA class II antigen. To that end, the peptides can be modified by substitution, insertion, deletion and/or addition of the amino acid residues to yield a modified peptide having improved binding affinity.

The present invention also contemplates the addition of one to two amino acids to the N and/or C-terminus of the described peptides. Such modified peptides having high HLA antigen binding affinity and retained Th1 cell inducibility are also included in the present invention.

For example, the present invention provides an isolated peptide of less than 31, 30, 29, 28, 27, or 26 amino acids in length which binds an HLA class II antigen, has Th1 cell inducibility, and comprises the amino acid sequence in which one, two or several amino acid(s) are modified in the amino acid sequence selected from the group consisting of SEQ ID NOs:1 and 2.

These peptides may also be processed in an APC to present a processed fragment thereon, when these peptides are contacted with, or introduced into APC. For example, the peptide of the present invention may be processed into a fragment composed of usually 11-26 (typically 15-25) amino acid residues to be presented on a surface of an APC.

However, when the peptide sequence is identical to a portion of the amino acid sequence of an endogenous or exogenous protein having a different function, negative side effects such as autoimmune disorders and/or allergic symptoms against specific substances may be induced. Therefore, it may be desirable to first perform homology searches using available databases to avoid situations in which the sequence of the peptide matches the amino acid sequence of another protein. When it becomes clear from the homology searches that no peptide identical to or having 1 or 2 amino acid differences as compared to the objective peptide, the objective peptide exists in nature can be modified in order to increase its binding affinity with HLA antigens, and/or increase its Th1 cell and/or CTL inducibility without any danger of such side effects.

Although peptides having high binding affinity to the HLA class II antigens as described above are expected to be highly effective, the candidate peptides, which are selected according to the presence of high binding affinity as an indicator, are further examined for the presence of Th1 cell inducibility. Herein, the phrase "Th1 cell inducibility" indicates an ability of a peptide to confer an ability to induce a Th1 cell on an APC when contacted with the APC. Further, "Th1 cell inducibility" includes the ability of the peptide to induce Th1 cell activation and/or Th1 cell proliferation, promote Th1 cell mediated-cytokines production including IFN-gamma production to help and/or stimulate other cells (e.g. CTL, macrophage).

Confirmation of Th1 cell inducibility is accomplished by inducing antigen-presenting cells carrying human MHC antigens (for example, B-lymphocytes, macrophages, and dendritic cells (DCs)), or more specifically DCs derived from human peripheral blood mononuclear leukocytes, and after stimulation with the peptides, mixing with CD4-positive T cells, and then measuring the IFN-gamma produced and released by CD4+ T cells. Alternatively, Th1 cell inducibility of the peptide can be assessed based on CTL activation by Th1 cells. For example, CD4+ T cells are co-cultured with DCs stimulated with a test peptide, and then mixing with CTLs and target cells for CTLs. The target cells can be radiolabeled with $^{51}$Cr and such, and cytotoxic activity of CTLs activated by the cytokines secreted from Th1 cells can be calculated from radioactivity released from the target cells. Alternatively, Th1 cells inducibility can be assessed by measuring IFN-gamma produced and released by Th1 cells in the presence of antigen-presenting cells (APCs) stimulated with a test peptide, and visualizing the inhibition zone on the media using anti-IFN-gamma monoclonal antibodies.

In addition to the above-described modifications, the peptides of the present invention can also be linked to other substances, so long as the resulting linked peptide retains the Th1 cell inducibility of the original peptide. Examples of suitable substances include, for example: peptides, lipids, sugar and sugar chains, acetyl groups, natural and synthetic polymers, etc. The peptides of the present invention can contain modifications such as glycosylation, side chain oxidation, or phosphorylation, etc., provided the modifications do not destroy the biological activity of the original peptide. These kinds of modifications can be performed to confer additional functions (e.g., targeting function, and delivery function) or to stabilize the peptide.

For example, to increase the in vivo stability of a peptide, it is known in the art to introduce D-amino acids, amino acid mimetics or unnatural amino acids; this concept can also be adapted to the peptides of the present invention. The stability of a peptide can be assayed in a number of ways. For instance, peptidases and various biological media, such as human plasma and serum, can be used to test stability (see, e.g., Verhoef et al., Eur J Drug Metab Pharmacokin 1986, 11: 291-302).

The peptides of the present invention may be presented on the surface of an APC as complexes in combination with HLA class II antigens and then induce Th1 cells. Therefore, the peptides forming complexes with HLA class II antigens on the surface of an APC are also included in the present invention. The APCs presenting the peptides of the present invention can be inoculated as vaccines.

The type of HLA antigens contained in the above complexes must match that of the subject requiring treatment and/or prevention. For example, in the Japanese population, HLA-DP5, DR8, and DR15 are prevalent and therefore would be appropriate for treatment of a Japanese patient. Typically, in the clinic, the type of HLA antigen of the patient requiring treatment is investigated in advance, which enables the appropriate selection of peptides having binding ability to the particular HLA class II antigen. In preferred embodiments, the peptides of the present invention can induce Th1 cells in a promiscuous manner. Herein, when a peptide can induce Th1 cells restricted by at least two different kinds of MHC class II molecules, the Th1 cell inducibility of the peptide is "promiscuous". In other word, when a peptide is recognized by at least two different kinds of MHC class II molecules, such antigen recognition is deemed "promiscuous". When used in the context of peptides, the phrase "recognized by at least two different kinds of MHC class II molecules" indicates that the peptide or fragment thereof can bind at least two different kinds of MHC class II molecules. For example, LY6K (119-142) (SEQ ID NO: 1) and LY6K (172-191) (SEQ ID NO: 2) are recognized by HLA-DP5, DR15 and DR8, and HLA-DR15 and one or several HLA-DQs, respectively. Therefore, these peptides are typical examples of "promiscuous" epitope.

When using HLA-DP5, HLA-DR15 or HLA-DR8 positive APCs, the peptides having the amino acid sequence of SEQ ID NO: 1 are preferably used. On the other hand, when using HLA-DR15 positive APCs, preferred peptides are peptides having the amino acid sequence of SEQ ID NO: 2.

Accordingly, in preferred embodiments, peptides having the amino acid sequence of SEQ ID NO: 1 may be used for the induction of Th1 cells in a subject that has been identified as having HLA-DP5, HLA-DR15 or HLA-DR8 prior to the induction. Likewise, peptides having the amino acid sequence of SEQ ID NO: 2 may be used for the induction of Th1 cells in a subject that has been identified as having HLA-DR15 prior to the induction.

III. Preparation of LY6K Peptides

The peptides of the present invention can be prepared using well known techniques. For example, the peptides of the present invention can be prepared synthetically, using recombinant DNA technology or chemical synthesis. The peptide of the present invention can be synthesized individually or as longer polypeptides composed of two or more peptides. The peptides of the present invention can be then be isolated, i.e., purified, so as to be substantially free of other naturally occurring host cell proteins and fragments thereof, or any other chemical substances.

The peptides of the present invention may contain modifications, such as glycosylation, side chain oxidation, or phosphorylation; provided the modifications do not destroy the biological activity of the original reference peptides. Other illustrative modifications include incorporation of D-amino acids or other amino acid mimetics that can be used, for example, to increase the serum half life of the peptides.

Peptides of the present invention can be obtained through chemical synthesis based on the selected amino acid sequence. Examples of conventional peptide synthesis methods that can be adapted for the synthesis include:

(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;
(vi) WO99/67288; and
(vii) Barany G. & Merrifield R. B., Peptides Vol. 2, "Solid Phase Peptide Synthesis", Academic Press, New York, 1980, 100-118.

Alternatively, the peptides of the present invention can be obtained adapting any known genetic engineering method for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. The host cell is then cultured to produce the peptide of interest. The peptide of the present invention can also be produced in vitro adopting an in vitro translation system.

IV. Polynucleotides

The present invention also provides a polynucleotide which encodes any of the aforementioned peptides of the present invention. These include polynucleotides derived from the natural occurring LY6K gene (GenBank Accession No. NM_017527 (SEQ ID NO: 7)) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of ordinary skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. As is well known in the art, a DNA is suitably composed of bases such as A, T, C, and G, and T is replaced by U in an RNA. One of skill will recognize that non-naturally occurring bases may be included in polynucleotides, as well.

The polynucleotide of the present invention can encode multiple peptides of the present invention with or without intervening amino acid sequences in between. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer R P, Tetrahedron 1992, 48: 2223-311; Matthes et al., EMBO J 1984, 3: 801-5.

V. Antigen-Presenting Cells (APCS)

The present invention also provides antigen-presenting cells (APCs) that present complexes formed between HLA class II antigens and the peptides of the present invention or fragment thereof on its surface. The APCs that are obtained by contacting the peptides of the present invention can be derived from patients who are subject to treatment and/or prevention, and can be administered as vaccines by themselves or in combination with other drugs including the peptides of the present invention, Th1 cells or CTLs.

The APCs are not limited to a particular kind of cells and include dendritic cells (DCs), Langerhans cells, macrophages, B cells, and activated T cells, which are known to present proteinaceous antigens on their cell surface so as to be recognized by lymphocytes. Since a DC is a representative APC having the strongest Th1 cell-inducing activity among APCs, DCs find use as the APCs of the present invention.

Moreover, in preferred embodiments, the peptides of the present invention can also induce CTL response mediated with the MHC class I antigen, as well as Th1 (class-II). In general, it is well known that the length of epitope recognized by the MHC-class I antigen is shorter (e.g. 8-10 amino acid residues) than that of MHC-class II (15 or more). Therefore, a processed product of the peptide of the present invention leads to induce CTL. In fact, CTL induced from LY6K (172-191) (SEQ ID NO: 2) recognizes the fragment (RYCNLEGPPI: SEQ ID NO: 3) which has already been identified as a CTL recognition epitope. Accordingly, peptides of the present invention induce not only Th1 but also CTL after processing of them in APCs. In other words, APCs contacted with the peptides of the present invention process them to present fragments thereof with MHC-class I antigens, as well as the whole of them presented with MHC-class-II antigens. Consequently, both of Th1 which recognizes the peptides of the present invention presented on APCs with the MHC class II antigen, and CTL induced via processed fragments of the peptide can be induced using the peptides present invention.

For example, an APC can be obtained by inducing DCs from peripheral blood monocytes and then contacting (stimulating) them with the peptides of the present invention in vitro, ex vivo or in vivo. When the peptides of the present invention are administered to the subjects, APCs that present the peptides of the present invention or fragments thereof are induced in the body of the subject. Herein, the phrase "inducing an APC" includes contacting (stimulating) an APC with the peptides of the present invention to present complexes formed between HLA class II antigens and the peptides of the present invention or fragments thereof on their surface. Alternatively, after introducing the peptides of the present invention to APCs to allow the APCs to present the peptides or fragments thereof, the APCs can be administered to the subject as a vaccine. For example, the ex vivo administration can include steps of:

a: collecting APCs from a first subject:

b: contacting the APCs of step a, with the peptide of the present invention and c: administering the peptide-loaded APCs to a second subject.

The first subject and the second subject may be the same individual, or can be different individuals. Alternatively, according to the present invention, use of the peptides of the present invention for manufacturing a pharmaceutical composition inducing antigen-presenting cells is provided. In addition, the present invention provides a method or process for manufacturing a pharmaceutical composition inducing antigen-presenting cells, wherein the method comprises the step for admixing or formulating the peptide of the present invention with a pharmaceutically acceptable carrier. Further, the present invention also provides the peptides of the present invention for inducing antigen-presenting cells. The APCs obtained by step (b) can be administered to the subject as a vaccine.

In one aspect of the present invention, the APCs of the present invention have a high level of Th1 cell inducibility. Herein, in the phrase "high level of Th1 cell inducibility", the high level is relative to the level of that by APCs contacting with no peptide or peptides which can not induce Th1 cells. Herein, when used in the context of APCs, the phrase "Th1 cell inducibility" indicates an ability of an APC to induce a Th1 cell when contacted with a CD4+ T cell. Such APCs having a high level of Th1 cell inducibility can be prepared by a method which includes the step of transferring genes containing polynucleotides that encode the peptides of the present invention to APCs in vitro. The introduced genes can be in the form of DNAs or RNAs. Examples of methods for introduction include, without particular limitations, various methods conventionally performed in this field, such as lipofection, electroporation, and calcium phosphate method can be used. More specifically, it can be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present peptides. Alternatively, the APCs of the present invention can be prepared by a method which induces the step of contacting APCs with the peptide of the present invention.

In preferred embodiments, the APCs of the present invention can be APCs that present complexes of an MHC class II molecule selected from the group among HLA-DP5, HLA-DR15 and HLA-DR8 and the peptide of the present invention (including an amino acid sequence SEQ ID NO: 1) on their surface. In another embodiment, the APCs of the present invention can be APCs that present complexes of an MHC class II molecule selected from the group among HLA-DR15 and one of HLA-DQs and the peptide of the present invention (including an amino acid sequence SEQ ID NO: 2) on their surface. Preferably, HLA-DP5, HLA-DR15 and HLA-DR8 may be HLA-DPB1*05:01, HLA-DRB1*15:02 and HLA-DRB1*08:03, respectively.

VI. T Helper-Type 1 Cells (Th1 Cells)

A Th1 cell induced against any of the peptides of the present invention strengthens immune responses of any of effector cells including CTLs targeting cancer cells in vivo, and thus serve as vaccines, in a fashion similar to the peptides per se. Thus, the present invention also provides isolated Th1 cells that are specifically induced or activated by any of the peptides of the present invention.

Such Th1 cells can be obtained by (1) administering one or more peptides of the present invention to a subject, collecting Th1 cells from the subject, (2) contacting (stimulating) APCs and CD4+ T cells, or peripheral blood mononuclear leukocytes in vitro with the peptides of the present invention, and then isolating Th1 cells, (3) contacting CD4+ T cells or peripheral blood mononuclear leukocytes in vitro with the APCs of the present invention, or (4) introducing a polynucleotide encoding both of T cell receptor (TCR) subunits or polynucleotides encoding each of TCR subunits into a CD4+ T cell, wherein the TCR can bind to a complex of a MHC class II molecule and the peptide of the present invention. Such APCs for the method of (3) can be prepared by the methods described above. Details of the method of (4) is described bellow in section "VII. T cell receptor (TCR)".

Th1 cells that have been induced by stimulation with APCs of the present invention can be derived from patients who are subject to treatment and/or prevention, and can be administered by themselves or in combination with other drugs including the peptides of the present invention for the purpose of regulating effects. The obtained Th1 cells can activate and/or stimulate immune cells responsible for cellular immunity (e.g., CTL, macrophage). Such immune cells that can be activated by the Th1 cells of the present invention include CTLs that show cytotoxicity against target cells such as cancer cells. For example, target cells for such CTLs may be cells that endogenously express LY6K (e.g., cancer cells), or cells that are transfected with the LY6K gene. In preferred embodiments, the peptides of the present invention can contain at least one amino acid sequence of a CTL epitope peptide and also induce CTLs against LY6K expressing cells such as cancer cells, in addition to Th1 cells. In this case, the peptide of the present invention can induce Th1 cells and CTLs simultaneously or sequentially in vivo, and the induced Th1 cells can effectively activate the induced CTLs. Accordingly, such peptides containing at least one amino acid sequence of a CTL epitope peptide are suitable peptides for cancer immunotherapy.

Furthermore, the Th1 cells of the present invention secrete various cytokines (e.g. IFN-gamma) which activate and/or stimulate any CTLs against other target cells in an antigen independent manner. Accordingly, the Th1 cells of the present invention can also contribute to enhance CTL activity targeting cells expressing a tumor associated antigen (TAA) other than LY6K. Thus, the Th1 cells of the present invention are useful for immunotherapy for not only tumor expressing LY6K, but also tumor expressing other TAAs, as well as the peptides and APCs of the present invention.

In some embodiments, the Th1 cells of the present invention are Th1 cells that recognize cells presenting complexes of an HLA-DR, HLA-DP or HLA-DQ antigen and the peptide of the present invention. In the context of Th1 cells, the phrase "recognize a cell" refers to binding of a complex of an MHC class II molecule and the peptide of the present invention on the cell surface via its TCR and being activated in an antigen specific manner. Herein, the phrase "activated in antigen specific manner" refers to being activated in response to a particular MHC class II molecule and peptide and cytokine production from the activated Th1 cells are induced. In preferred embodiments, HLA-DR may be selected from the group consisting of HLA-DR8 and HLA-DR15. Preferably, HLA-DR8 and HLA-DR15 may be HLA-DRB1*08:03 and HLA-DRB1*15:02, respectively. On the other hand, HLA-DP5 is a preferable example of the HLA-DP antigens. More preferably, HLA-DP5 may be HLA-DPB1*05:01.

VII. T Cell Receptor (TCR)

The present invention also provides a composition containing one or more polynucleotides encoding one or more polypeptides that are capable of forming a subunit of a T cell receptor (TCR), and methods of using the same. Such TCR subunits have the ability to form TCRs that confer specificity to CD4+ T cells against APCs presenting LY6K peptides. By using the known methods in the art, the nucleic acids of alpha- and beta-chains as the TCR subunits of Th1 cells induced by the peptides of the present invention can be identified (WO2007/032255 and Morgan et al., J Immunol, 171, 3288 (2003)). The derivative TCRs can bind APCs displaying LY6K peptides with high avidity, and optionally mediate efficient cytokine productions.

The polynucleotide/polynucleotides encoding the TCR subunits (i.e., a single polynucleotide encoding both of the TCR subunits or multiple polynucleotides each encoding a separate TCR subunits) can be incorporated into suitable vectors e.g. retroviral vectors. These vectors are well known in the art. The polynucleotides or the vectors containing them usefully can be transferred into a CD4+ T cell, for example, a CD4+ T cell from a patient. Advantageously, the present invention provides an off-the-shelf composition allowing rapid modification of a patient's own T cells (or those of another mammal) to rapidly and easily produce modified T cells having excellent cancer cell killing properties.

The present invention further provides Th1 cells which are prepared by transduction with the polynucleotide encoding both of the TCR subunits or polynucleotides encoding each of TCR subunits, wherein the TCR subunit can bind to the LY6K peptide (e.g. SEQ ID NO: 1 in the context of HLA-DP5, HLA-DR15 or HLA-DR8, and SEQ ID NO: 2 in the context of HLA-DR15 or one of HLA-DQs). The transduced Th1 cells are capable of homing to cancer cells in vivo, and can be expanded by well known culturing methods in vitro (e.g., Kawakami et al., J Immunol., 142, 3452-3461 (1989)). The Th1 cells prepared as described above can be used to form an immunogenic composition useful in treating or the prevention of cancer in a patient in need of therapy or protection.

VIII. Pharmaceutical Agents or Compositions

To the extent that the methods and compositions of the present invention find utility in the context of the "treatment" of cancer, a treatment is deemed "efficacious" if it leads to clinical benefit such as, reduction in expression of LY6K gene, or a decrease in size, prevalence, or metastatic potential of the cancer in the subject. When the treatment is applied prophylactically, "efficacious" means that it retards or prevents cancers from forming or prevents or alleviates a clinical symptom of cancer. Efficaciousness is determined in association with any known method for diagnosing or treating the particular tumor type.

To the extent that the methods and compositions of the present invention find utility in the context of the "prevention" and "prophylaxis" of cancer, such terms are interchangeably used herein to refer to any activity that reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis include a wide range of prophylactic therapies aimed at alleviating the severity of the particular disorder, e.g. reducing the proliferation and metastasis of tumors, reducing angiogenesis.

In the context of the present invention, the treatment and/or prophylaxis of cancer and/or the prevention of postoperative recurrence thereof include any of the following steps, such as surgical removal of cancer cells, inhibition of the growth of cancerous cells, involution or regression of a tumor, induction of remission and suppression of occurrence of cancer, tumor regression, and reduction or inhibition of metastasis. Effectively treating and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

As described above, the Th1 cells induced by the peptides of the present invention can help immune cells responsible for cellular immunity. Such immune cells include CTLs against not only cancer cells expressing LY6K, but also cancer cells expressing other TAAs, since cytokines secreted by Th1 cells can affect CTLs in antigen independent manner. Accordingly, the present invention provides a pharmaceutical agent or composition comprising at least one peptide of the present invention. In the pharmaceutical agent or composition, such peptide is present in a therapeutically or pharmaceutically effective amount. A pharmaceutical agent or composition of the present invention is useful for helping, stimulating and/or enhancing any immune cells responsible for cellular immunity (e.g., CTLs, macrophage), since Th1 cells induced by the agent or composition of the present invention can secrete cytokines that affects any immune cells responsible for cellular immunity. Therefore, the agent or composition of the present invention is useful for any purposes of enhancing or promoting immune responses mediated with such immune cells including CTLs. For example, the present invention provides agent or compositions comprising at least one of the peptide of the present invention, for use in treatment and/or prevention of cancer since the agent or composition of the present invention can enhance or promote immune responses against cancer or tumor mediated with such immune cells. The amount of the peptide in such agent or composition may be an amount that is effective in significantly enhancing or stimulating immunological response in a subject carrying a cancer expressing LY6K.

Furthermore, as shown in FIG. 6, LY6K derived peptides identified in the course of the present invention have been confirmed to enhance CTL induction compared with stimulation with a CTL epitope only. Therefore, the present invention also provides an agent or composition for enhancing or stimulating immunological responses mediated with an MHC class I antigen, such as HLA-A24. In another embodiment, the present invention further provides a use of the peptide of the present invention for manufacturing an agent or composition for enhancing or stimulating an immunological response mediated with an MHC class I antigen.

In preferred embodiments, LY6K derived peptides identified in the course of the present invention can induce Th1 cells, as well as CTLs against LY6K-expressing cells. Accordingly, the present invention also provides agents or compositions comprising at least one of the peptide of the present invention, for use in the induction of CTLs against cancer or tumor expressing LY6K.

Moreover, the agent or composition comprising at least one of the peptides of the present invention can be used in enhancing or promoting immune responses mediated by MHC class II molecules.

Since LY6K expression is specifically elevated in several cancer types, including bladder cancer, cervical cancer, cholangiocellular carcinoma, esophageal cancer, gastric cancer, non-small cell lung cancer (NSCLC), osteosarcoma, pancreatic cancer and soft tissue tumor as compared with normal tissue (WO2008/102557, WO2009/016691 and WO2004/031413), the peptides of the present invention or polynucleotides encoding the peptides can be used for the treatment and/or prophylaxis of cancer or tumor, and/or for the prevention of postoperative recurrence thereof. Thus, the present invention provides a pharmaceutical agent or a composition for treating and/or for the prophylaxis of cancer or tumor, and/or prevention of postoperative recurrence thereof, which comprises one or more of the peptides of the present invention, or polynucleotides encoding the peptides as an active ingredient. Alternatively, the present peptides can be expressed on the surface of any of the foregoing cells, such as APCs for the use as pharmaceutical agents or compositions. In addition, the aforementioned Th1 cells can also be used as active ingredients of the present pharmaceutical agents or compositions.

In another embodiment, the present invention also provides the use of an active ingredient selected from among:
(a) a peptide of the present invention,
(b) a polynucleotide encoding such a peptide as disclosed herein in an expressible form,
(c) an APC presenting on its surface a peptide of the present invention or fragment thereof, and
(d) a Th1 cell of the present invention
in manufacturing a pharmaceutical composition or agent for treating cancer or tumor.

Alternatively, the present invention further provides an active ingredient selected from among:
(a) a peptide of the present invention,
(b) a polynucleotide encoding such a peptide as disclosed herein in an expressible form,
(c) an APC presenting on its surface a peptide of the present invention or fragment thereof, and
(d) a Th1 cell of the present invention for use in treating cancer or tumor.

Alternatively, the present invention further provides a method or process for manufacturing a pharmaceutical composition or agent for treating cancer or tumor, wherein the method or process includes the step of formulating a pharmaceutically or physiologically acceptable carrier with an active ingredient selected from among:
(a) a peptide of the present invention,
(b) a polynucleotide encoding such a peptide as disclosed herein in an expressible form,
(c) an APC presenting on its surface a peptide of the present invention or fragment thereof, and
(d) a Th1 cell of the present invention as active ingredients.

In another embodiment, the present invention also provides a method or process for manufacturing a pharmaceutical composition or agent for treating cancer or tumor, wherein the method or process includes the step of admixing an active ingredient with a pharmaceutically or physiologically acceptable carrier, wherein the active ingredient is selected from among:
(a) a peptide of the present invention,
(b) a polynucleotide encoding such a peptide as disclosed herein in an expressible form,
(c) an APC presenting on its surface a peptide of the present invention or fragment thereof, and
(d) a Th1 cell of the present invention.

Alternatively, the pharmaceutical composition or agent of the present invention may be used for either or both of the prophylaxis of cancer or tumor and prevention of postoperative recurrence thereof.

The present pharmaceutical agents or compositions find use as a vaccine. In the context of the present invention, the phrase "vaccine" (also referred to as an immunogenic composition) refers to a composition that has the function to induce anti-tumor immunity upon inoculation into animals.

The pharmaceutical agents or compositions of the present invention can be used to treat and/or prevent cancers or tumors, and/or prevent of postoperative or metastatic recurrence thereof in subjects or patients. Examples of such subjects include humans as well as other mammals including, but not limited to, mouse, rat, guinea-pig, rabbit, cat, dog, sheep, goat, pig, cattle, horse, monkey, baboon, and chimpanzee, particularly a commercially important animal or a domesticated animal.

In the course of the present invention, the peptides having an amino acid sequence selected from among SEQ ID NOs: 1 and 2 have been found to be promiscuous Th1 cell epitopes restricted by several HLA-DR1, HLA-DP and/or HLA-DQ molecules (i.e., HLA-DP5, HLA-DR8, HLA-DR15, one or several HLA-DQs) and can be candidates that can induce potent and specific immune response against cancer due to immune responses mediated with MHC class II molecules. Therefore, the present pharmaceutical agents or compositions which include any of these peptides having the amino acid sequences of SEQ ID NOs: 1 or 2 are particularly suited for the administration to subjects that have at least one selected from among HLA-DP5, HLA-DR15, HLA-DR8 as an MHC class II molecule. Furthermore, demonstrated herein, peptides having the amino acid sequence of SEQ ID NO: 2 (including peptides having the amino acid sequence of SEQ ID NO: 6) was confirmed to bind to an unknown HLA-DQ molecule (FIG. 3). Therefore, pharmaceutical agents or compositions comprising peptides having the amino acid sequence of SEQ ID NO: 2 may be suited for the administration to subjects not having HLA-DR15. The same applies to pharmaceutical agents or compositions which contain polynucleotides encoding any of these peptides.

Alternatively, in preferred embodiments, a peptide identified in the course of the present invention can also induce CTLs specific to LY6K, when the peptide is applied to a subject having HLA-A24. Accordingly, through the administration of the peptide of the present invention, it is further expected that CTL response against cancer expressing LY6K can be induced in addition to Th1 cell induction. Moreover, the peptide of the present invention can not only induce CTL response against LY6K-expressing cells via processing thereof, but also enhance it by Th1 cell induction mediated thereby. Accordingly, in order to achieve inductions of both of Th1 cells and LY6K-specific CTLs in the same subject, for example, the subject to be treated preferably has HLA-DR15 as a MHC class II molecule and HLA-A24 as an MHC class I molecule, when administering peptides having the amino acid sequence of SEQ ID NO: 2. Furthermore, since the peptide having the amino acid sequence of SEQ ID NO: 2 (including peptides having the amino acid sequence of SEQ ID NO: 6) can bind to one or several HLA-DQ molecules, such peptides may induce Th1 cells and CTLs in subjects having HLA-A24 as an MHC class I molecule and not having HLA-DR15 as an MHC class II molecule.

In another embodiment, the present invention provides an immunological cancer therapy dependent on Th1 cell induction. The therapeutic strategy provided by the present invention is applicable to and effective for any cancers independent of LY6K expression, as long as immune cells activated by cytokines secreted from Th1 cells target objective cancer cells.

Cancers or tumors to be treated by the pharmaceutical agents or compositions of the present invention include, but are not limited and preferred examples of such cancers include any kinds of cancers or tumors expressing LY6K, including for example, bladder cancer, cervical cancer, cholangiocellular carcinoma, esophageal cancer, gastric cancer, non-small cell lung cancer (NSCLC), osteosarcoma, pancreatic cancer, soft tissue tumor and head-and-neck malignant tumor (HNMT).

The present pharmaceutical agents or compositions can contain in addition to the aforementioned active ingredients, other peptides that have the ability to induce Th1 cells or CTLs, other polynucleotides encoding the other peptides, other cells that present the other peptides or fragment thereof, and the like. Examples of such "other" peptides having the ability to induce Th1 cells or CTLs include, but are not limited to, peptides derived from cancer specific antigens (e.g., identified TAAs), but are not limited thereto.

If necessary, the pharmaceutical agents or compositions of the present invention can optionally include other therapeutic substances as an additional active ingredient, so long as the substance does not inhibit the antitumoral effect of the active ingredient, e.g., any of the present peptides. For example, formulations can include anti-inflammatory agents, pain killers, chemotherapeutics, and the like. In addition to including other therapeutic substances in the medicament itself, the medicaments of the present invention can also be administered sequentially or concurrently with the one or more other pharmacologic agents. The amounts of medicament and pharmacologic agent depend, for example, on what type of pharmacologic agent(s) is/are used, the disease being treated, and the scheduling and routes of administration.

Those of skill in the art will recognize that, in addition to the ingredients particularly mentioned herein, the pharmaceutical agents or compositions of the present invention can include other agents conventional in the art having regard to the type of formulation in question (e.g., fillers, binders, diluents, excipients, etc.).

In one embodiment of the present invention, the present pharmaceutical agents or compositions can be included in articles of manufacture and kits containing materials useful for treating the pathological conditions of the disease to be treated, e.g., cancer. The article of manufacture can include a container of any of the present pharmaceutical agents or compositions with a label. Suitable containers include bottles, vials, and test tubes. The containers can be formed from a variety of materials, such as glass or plastic. The label on the container should indicate the agent is used for treating or prevention of one or more conditions of the disease. The label can also indicate directions for administration and so on.

In addition to the container described above, a kit including a pharmaceutical agent or composition of the present invention can optionally further include a second container housing a pharmaceutically-acceptable diluent. It can further include other materials desirable from a commercial and user standpoint, including other buffers, diluents, filters, needles, syringes, and package inserts with instructions for use.

The pharmaceutical agents or compositions can, if desired, be packaged in a pack or dispenser device that can contain one or more unit dosage forms containing the active ingredient. The pack can, for example, include metal or plastic foil, such as a blister pack. The pack or dispenser device can be accompanied by instructions for administration.

(1) Pharmaceutical Agents or Compositions Containing the Peptides as the Active Ingredient The peptide of the present invention can be administered directly as a pharmaceutical agent or composition, or if necessary, that has been formulated by conventional formulation methods. In the latter case, in addition to the peptides of the present invention, carriers, excipients, and such that are ordinarily used for drugs can be included as appropriate without particular limitations. Examples of such carriers include, but are not limited to, sterilized water, physiological saline, phosphate buffer, culture fluid and such. Furthermore, the pharmaceutical agents or compositions can contain as necessary, stabilizers, suspensions, preservatives, surfactants and such. The pharmaceutical agents or compositions of the present invention can be used for anticancer purposes.

The peptides of the present invention can be prepared in a combination, composed of two or more of peptides of the present invention to induce Th1 cells in vivo. The peptide combination can take the form of a cocktail or can be conjugated to each other using standard techniques. For example, the peptides can be chemically linked or expressed as a single fusion polypeptide sequence. The peptides in the combination can be the same or different.

By administering the peptides of the present invention, the peptides or fragments thereof are presented at a high density by the HLA class II antigens on APCs, then Th1 cells that specifically react toward the complex formed between the displayed peptide and the HLA class II antigen are induced. Alternatively, APCs (e.g., DCs) are removed from subjects and then stimulated by the peptides of the present invention to obtain APCs that present any of the peptides of this invention or fragments thereof on their surface. These APCs can be readministered to the subjects to induce Th1 cells in the subjects, and as a result, aggressiveness towards the tumor-associated endothelium can be increased.

The pharmaceutical agents or compositions for the treatment and/or prevention of cancer or tumor, that include a peptide of the present invention as the active ingredient, can also include an adjuvant known to effectively establish cellular immunity. Alternatively, the pharmaceutical agents or compositions can be administered with other active ingredients or can be administered by formulation into granules. An adjuvant refers to a compound that enhances the immune response against the protein when administered together (or successively) with the protein having immunological activity. Adjuvants contemplated herein include those described in the literature (Clin Microbiol Rev 1994, 7: 277-89). Examples of suitable adjuvants include, but are not limited to, aluminum phosphate, aluminum hydroxide, alum, cholera toxin, *salmonella* toxin, Incomplete Freund's adjuvant (IFA), Complete Freund's adjuvant (CFA), ISCOMatrix, GM-CSF, CpG, O/W emulsion, and the like.

Furthermore, liposome formulations, granular formulations in which the peptide is bound to few-micrometers diameter beads, and formulations in which a lipid is bound to the peptide may be conveniently used.

In another embodiment of the present invention, the peptides of the present invention may also be administered in the form of a pharmaceutically acceptable salt. Examples of preferred salts include salts with an alkali metal, salts with a metal, salts with an organic base, salts with an organic acid (e.g., acetic acid, formic acid, propionic acid, fumaric acid, maleic acid, succinic acid, tartaric acid, citric acid, malic acid, oxalic acid, benzoic acid, methanesulfonic acid and so on) and salts with an inorganic acid (e.g., hydrochloric acid, phosphoric acid, hydrobromic acid, sulfuric acid and so on). As used herein, the phrase "pharmaceutically acceptable salt" refers to those salts that retain the biological effectiveness and properties of the compound and which are obtained by reaction with inorganic acids or bases such as hydrochloric acid, hydrobromic acid, sulfuric acid, nitric acid, phosphoric acid, methanesulfonic acid, ethanesulfonic acid, p-toluenesulfonic acid, salicylic acid and the like.

In some embodiments, the pharmaceutical agents or compositions of the present invention may further include a component which primes Th1 cells and optionally CTLs. Lipids have been identified as agents capable of priming Th1 cells and optionally CTLs in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of Th1 cell and optionally CTL responses, *E. coli* lipoproteins, such as tripalmitoyl-S-glycerylcysteinlyseryl-serine (P3CSS) can be used to prime Th1 cells and optionally CTLs when covalently attached to an appropriate peptide (see, e.g., Deres et al., Nature 1989, 342: 561-4).

Examples of suitable methods of administration include, but are not limited to, oral, intradermal, subcutaneous, intramuscular, intraosseous, peritoneal, and intravenous injection, or such, and systemic administration or local administration to the vicinity of the targeted sites (i.e., direct injection). The administration can be performed by single administration or boosted by multiple administrations. A pharmaceutically or therapeutically effective amount of the peptide can be administered to a subject in need of treatment of cancer expressing LY6K. Alternatively, an amount of the peptide of the present invention sufficient to enhance or stimulate immunological response mediated with Th1 cells, and/or to induce CTLs against cancer or tumor expressing LY6K can be administered to a subject carrying a cancer expressing LY6K. The dose of the peptides of the present invention can be adjusted appropriately according to the disease to be treated, age of the patient, weight, method of administration, and such, and is ordinarily 0.001 mg to 1000 mg, for example, 0.01 mg to 100 mg, for example, 0.1 mg to 10 mg, for example, 0.5 mg to 5 mg, and can be administered once in a few days to few months. One skilled in the art can readily determine suitable and optimal dosages.

(2) Pharmaceutical Agents or Compositions Containing Polynucleotides as the Active Ingredient The pharmaceutical agents or compositions of the present invention can also contain polynucleotides encoding the peptides disclosed herein in an expressible form. Herein, the phrase "in an expressible form" means that the polynucleotide, when introduced into a cell, will be expressed in vivo as a polypeptide that induces anti-tumor immunity. In an illustrative embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a subject can be either direct, in which case the subject is directly exposed to a polynucleotide-carrying vector, or indirect, in which case, cells are first transformed with the polynucleotide of interest in vitro, then the cells are transplanted into the subject. These two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology which can also be used for the present invention are described in eds. Ausubel et al., Current Protocols in Molecular Biology, John Wiley & Sons, NY, 1993; and Krieger, Gene Transfer and Expression, A Laboratory Manual, Stockton Press, NY, 1990.

Like administration of peptides, administration of polynucleotides may be performed by oral, intradermal, subcutaneous, intravenous, intramuscular, intraosseous, and/or peritoneal injection, or such, and via systemic administration or local administration to the vicinity of the targeted sites finds use. The administration can be performed by single administration or boosted by multiple administrations. A pharmaceutically or therapeutically effective amount of the polynucleotide can be administered to a subject in need of treatment of cancer expressing LY6K. Alternatively, an amount of the polynucleotide of the present invention sufficient to enhance or stimulate immunological response mediated with Th1 cells, and/or to induce CTLs against cancer or tumor expressing LY6K can be administered to a subject carrying a cancer expressing LY6K. The dose of the polynucleotide in the suitable carrier or cells transformed with the polynucleotide encoding the peptides of the present invention can be adjusted appropriately according to the disease to be treated, age of the patient, weight, method of administration, and such, and is ordinarily 0.001 mg to 1000 mg, for example, 0.01 mg to 100 mg, for example, 0.1 mg to 10 mg, for example, 0.5 mg to 5 mg, and can be administered once every a few days to once every few months. One skilled in the art can readily determine suitable and optimal dosages.

IX. Methods Using The Peptides, APCs OR Th1 Cells

The peptides of the present invention and polynucleotides encoding such peptides can be used for inducing APCs and Th1 cells of the present invention. The APCs of the present invention can be also used for inducing Th1 cells of the present invention. The peptides, polynucleotides, and APCs can be used in combination with any other compounds so long as the compounds do not inhibit their Th1 cell inducibility. Thus, any of the aforementioned pharmaceutical agents or compositions of the present invention can be used for inducing Th1 cells, and in addition thereto, those including the peptides and polynucleotides can be also used for inducing APCs as discussed below.

(1) Method of Inducing Antigen-Presenting Cells (APCs)

The present invention provides methods of inducing APCs using the peptides of the present invention or polynucleotides encoding the peptides. The induction of APCs can be performed as described above in section "V. Antigen-presenting cells". The present invention also provides a method for inducing APCs having Th1 cell inducibility, the induction of which has been also mentioned under the item of "V. Antigen-presenting cells", supra.

Alternatively, the present invention provides a method for preparing an antigen-presenting cell (APC) which has ability to induce a Th1 cell, wherein the method can include one of the following steps:

(a) contacting an APC with a peptide of the present invention in vitro, ex vivo or in vivo; and (b) introducing a polynucleotide encoding a peptide of the present invention into an APC.

Alternatively, the present invention provides methods for inducing an APC having Th1 cell inducibility, wherein the methods include the step selected from the group consisting of:

(a) contacting an APC with the peptide of the present invention, and (b) introducing the polynucleotide encoding the peptide of the present invention into an APC.

The methods of the present invention can be carried out in vitro, ex vivo or in vivo. Preferably, the methods of the present invention can be carried out in vitro or ex vivo. In preferred embodiment, APCs used for induction of APCs having Th1 cell inducibility can be preferably APCs expressing at least one selected from among HLA-DP5, HLA-DR15, HLA-DR8 and one of HLA-DQs as an MHC class II molecule. Such APCs can be prepared by the methods well-known in the arts from peripheral blood mononuclear cells (PBMCs) obtained from a subject having at least one selected from among HLA-DP5, HLA-DR15, HLA-DR8 and one of HLA-DQs as an MHC class II molecule. The APCs induced by the method of the present invention can be APCs that present a complex of the peptide of the present invention or fragment thereof and HLA class II antigen (e.g., HLA-DP5, HLA-DR15, HLA-DR8, one of HLA-DQs) on their surface. When APCs induced by the method of the present invention are administered to a subject in order to induce immune responses against cancer in the subject, the subject is preferably the same one from whom APCs are derived. However, the subject may be a different one from the APC donor so long as the subject has the same HLA type with the APC donor.

In another embodiment, the present invention provide agents or compositions for use in inducing an APC having Th1 cell inducibility, and such agents or compositions include one or more peptides or polynucleotides of the present invention.

In another embodiment, the present invention provides the use of the peptide of the present invention or the polynucleotide encoding the peptide in the manufacture of an agent or composition formulated for inducing APCs.

Alternatively, the present invention further provides the peptide of the present invention or the polypeptide encoding the peptide for use in inducing an APC having Th1 cell inducibility.

In preferred embodiments, the peptides of the present invention can induce not only Th1 response but also CTL response after processing them. Accordingly, in preferred embodiments, APCs prepared by the method of the present invention can be also useful for inducing CTLs against LY6K expressing cells, including cancer cells. For example, when induced by the peptides containing the amino acid sequence of SEQ ID NO: 3, APCs expressing HLA-A24 are suitable for inducing LY6K-specific CTLs.

(2) Method of Inducing Th1 Cells

Furthermore, the present invention provides methods for inducing Th1 cells using the peptides of the present invention, polynucleotides encoding the peptides or APCs presenting the peptides of the present invention or fragments thereof. The present invention also provides methods for inducing Th1 cells using a polynucleotide encoding a polypeptide that is capable of forming a T cell receptor (TCR) subunit recognizing a complex of the peptides of the present invention and HLA class II antigens. Preferably, the methods for inducing Th1 cells comprise at least one step selected from the group consisting of:

a: contacting a CD4-positive T cell with an antigen-presenting cell that presents on its surface a complex of an HLA class II antigen and the peptide of the present invention or fragment thereof, and b: introducing a polynucleotide encoding both of TCR subunits or polynucleotides encoding each of TCR subunits, wherein the TCR can recognize or bind to a complex of the peptide of the present invention or fragment thereof and an HLA class II antigen, into a CD4-positive T cell.

When the peptides of the present invention are administered to a subject, Th1 cells are induced in the body of the subject, and immune responses mediated by MHC class II molecules (e.g., immune responses targeting cancer cells) are enhanced. Alternatively, the peptides and polynucleotides encoding the peptides can be used for an ex vivo therapeutic method, in which subject-derived APCs and CD4-positive cells, or peripheral blood mononuclear leukocytes are contacted (stimulated) with the peptides of the present invention in vitro, and after inducing Th1 cells, the activated Th1 cells are returned to the subject. For example, the method can include the steps of:

a: collecting APCs from subject:

b: contacting the APCs of step a, with the peptide of the present invention:

c: mixing the APCs of step b with CD4$^+$ T cells, and co-culturing for inducing Th1 cells: and d: collecting CD4$^+$ T cells from the co-culture of step c.

Furthermore, Th1 cells can be induced by introducing a polynucleotide encoding both of TCR subunits or polynucleotides encoding each of TCR subunits, wherein the TCR can bind to a complex of the peptide of the present invention or fragment thereof and an HLA class II antigen, into CD4-positive T cells. Such transduction can be performed as described above in section "VII. T cell receptor (TCR)".

The methods of the present invention can be carried out in vitro, ex vivo or in vivo. Preferably, the methods of the present invention can be carried out in vitro or ex vivo. CD4 positive T cells used for induction of Th1 cells can be prepared by well-known methods in the art from PBMCs obtained from a subject. In preferred embodiments, the donor for CD4-positive T cells can be a subject having at least one selected from among HLA-DP5, HLA-DR15 and HLA-DR8 as an MHC class II molecule. Since the peptides having the amino acid sequence of SEQ ID NO: 2 can bind to one or several HLA-DQs, when using the peptides having the amino acid sequence SEQ ID NO: 2, the donor for CD4-positive T cells may not necessarily have the above MHC class II molecules. The Th1 cells induced by the methods of the present invention can be Th1 cells that can recognize APCs presenting a complex of the peptide of the present invention or fragment thereof and HLA class II antigen on its surface. When Th1 cells induced by the method of the present invention are administered to a subject in order to induce immune responses against cancer in the subject (or immune responses mediated by MHC class I molecules), the subject is preferably the same one from whom CD4-positive T cells are derived. However, the subject may be a different one from the CD4-positive T cell donor so long as the subject has the same HLA type with the CD4-positive T cell donor.

In preferred embodiments, the peptides of the present invention can induce CTLs against LY6K expressing cells, as well as Th1 cells. Therefore, the present invention further provides a method for inducing a CTL, which comprises at least one step selected from the group consisting of:

a: co-culturing both of a CD4-positive T cell and a CD8-positive T cell with APCs contacted with the peptide of the present invention; and b: co-culturing a CD8-positive T cell with an APC contacted with the peptide of the present invention.

In such methods of inducing CTLs, the peptides of the present invention are processed in APCs to produce CTL epitope peptides, and produced CTL epitope peptides are presented on APC's surface.

Alternatively, according to the present invention, use of the peptides of the present invention for manufacturing a pharmaceutical agent or composition inducing Th1 cells is provided. In addition, the present invention provides a method or process for manufacturing a pharmaceutical agent or composition inducing Th1 cells, wherein the method comprises the step for admixing or formulating the peptide of the present invention with a pharmaceutically acceptable carrier. Further, the present invention also provides the peptide of the present invention for inducing Th1 cells.

The CD4$^+$ T cells induced by the method of the present invention can be administered to a subject as a vaccine.

In the context of the present invention, cancer overexpressing LY6K can be treated with these active ingredients. Examples of such cancers include, but are not limited to, bladder cancer, cervical cancer, cholangiocellular carcinoma, esophageal cancer, gastric cancer, non-small cell lung cancer (NSCLC), osteosarcoma, pancreatic cancer, soft tissue tumor and head-and-neck malignant tumor (HNMT). Accordingly, prior to the administration of the vaccines or pharmaceutical compositions comprising the active ingredients, it is preferable to confirm whether the expression level of LY6K in the cancer cells or tissues to be treated is enhanced as compared with normal cells of the same organ. Thus, in one embodiment, the present invention provides a method for treating cancer (over)expressing LY6K, which method may include the steps of:

i) determining the expression level of LY6K in cancer cells or tissue(s) obtained from a subject with the cancer to be treated;

ii) comparing the expression level of LY6K with normal control; and iii) administrating at least one component selected from the group consisting of (a) to (d) described above to a subject with cancer overexpressing LY6K compared with normal control. Alternatively, the present invention may provide a vaccine or pharmaceutical composition that includes at least one component selected from the group consisting of (a) to (d) described above, for use in administrating to a subject having cancer overexpressing LY6K. In other words, the present invention further provides a method for identifying a subject to be treated with a LY6K polypeptide of the present invention, such method including the step of determining an expression level of LY6K in subject-derived cancer cells or tissue(s), wherein an increase of the level compared to a normal control level of the gene indicates that the subject has cancer which may be treated with the LY6K polypeptide of the present invention. Methods of treating cancer of the present invention are described in more detail below.

Further, in preferred embodiments, the HLA type of a subject may be identified before administering the peptides of the present invention. For example, peptides having the amino acid sequence of SEQ ID NO: 1 are preferably administered to a subject identified as having HLA-DP5, HLA-DR15 or HLA-DR8. Alternatively, peptides having the amino acid sequence of SEQ ID NO: 2 are preferably administered to a subject identified as having HLA-DR15.

Any subject-derived cell or tissue can be used for the determination of LY6K expression so long as it includes the objective transcription or translation product of LY6K. Examples of suitable samples include, but are not limited to, bodily tissues and fluids, such as blood, sputum and urine. Preferably, the subject-derived cell or tissue sample contains a cell population including an epithelial cell, more preferably a cancerous epithelial cell or an epithelial cell derived from tissue suspected to be cancerous. Further, if necessary, the cell may be purified from the obtained bodily tissues and fluids, and then used as the subjected-derived sample.

A subject to be treated by the present method is preferably a mammal. Exemplary mammals include, but are not limited to, e.g., human, non-human primate, mouse, rat, dog, cat, horse, and cow.

According to the present invention, the expression level of LY6K in cancer cells or tissues obtained from a subject is determined. The expression level can be determined at the transcription (nucleic acid) product level, using methods known in the art. For example, the mRNA of LY6K may be quantified using probes by hybridization methods (e.g., Northern hybridization). The detection may be carried out on a chip or an array. The use of an array is preferable for detecting the expression level of LY6K. Those skilled in the art can prepare such probes utilizing the sequence information of LY6K. For example, the cDNA of LY6K may be used as the probes. If necessary, the probes may be labeled with a suitable label, such as dyes, fluorescent substances and isotopes, and the expression level of the gene may be detected as the intensity of the hybridized labels.

Furthermore, the transcription product of LY6K (e.g., SEQ ID NO: 7) may be quantified using primers by amplification-based detection methods (e.g., RT-PCR). Such primers may be prepared based on the available sequence information of the gene.

Specifically, a probe or primer used for the present method hybridizes under stringent, moderately stringent, or low stringent conditions to the mRNA of LY6K. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degree Centigrade lower than the thermal melting point (Tm) for a specific sequence at a defined ionic strength and pH. The Tm is the temperature (under a defined ionic strength, pH and nucleic acid concentration) at which 50% of the probes complementary to their target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degree Centigrade for short probes or primers (e.g., 10 to 50 nucleotides) and at least about 60 degree Centigrade for longer probes or primers. Stringent conditions may also be achieved with the addition of destabilizing agents, such as formamide.

Alternatively, the translation product may be detected for the diagnosis of the present invention. For example, the quantity of LY6K protein (SEQ ID NO: 8) may be determined. Methods for determining the quantity of the protein as the translation product include immunoassay methods that use an antibody specifically recognizing the protein. The antibody may be monoclonal or polyclonal. Furthermore, any fragment or modification (e.g., chimeric antibody, scFv, Fab, F(ab')$_2$, Fv, etc.) of the antibody may be used for the detection, so long as the fragment or modified antibody retains the binding ability to the LY6K protein. Methods to prepare these kinds of antibodies for the detection of proteins are well known in the art, and any method may be employed in the present invention to prepare such antibodies and equivalents thereof.

As another method to detect the expression level of LY6K gene based on its translation product, the intensity of staining may be measured via immunohistochemical analysis using an antibody against the LY6K protein. Namely, in this measurement, strong staining indicates increased presence/level of the protein and, at the same time, high expression level of LY6K gene.

The expression level of a target gene, e.g., the LY6K gene, in cancer cells can be determined to be increased if the level increases from the control level (e.g., the level in normal cells) of the target gene by, for example, 10%, 25%, or 50%; or increases to more than 1.1 fold, more than 1.5 fold, more than 2.0 fold, more than 5.0 fold, more than 10.0 fold, or more.

The control level may be determined at the same time as the cancer cells, by using a sample(s) previously collected and stored from a subject/subjects whose disease state(s) (cancerous or non-cancerous) is/are known. In addition, normal cells obtained from non-cancerous regions of an organ that has the cancer to be treated may be used as normal control. Alternatively, the control level may be determined by a statistical method based on the results obtained by analyzing previously determined expression level(s) of LY6K gene in samples from subjects whose disease states are known. Furthermore, the control level can be derived from a database of expression patterns from previously tested cells. Moreover, according to an aspect of the present invention, the expression level of LY6K gene in a biological sample may be compared to multiple control levels determined from multiple reference samples. It is preferred to use a control level determined from a reference sample derived from a tissue type similar to that of the subject-derived biological sample. Moreover, it is preferred to use the standard value of the expression levels of LY6K gene in a population with a known disease state. The standard value may be obtained by any method known in the art. For example, a range of mean+/−2 S.D. or mean+/−3 S.D. may be used as the standard value.

In the context of the present invention, a control level determined from a biological sample that is known to be non-cancerous is referred to as a "normal control level". On the other hand, if the control level is determined from a cancerous biological sample, it is referred to as a "cancerous control level". Difference between a sample expression level and a control level can be normalized to the expression level of control nucleic acids, e.g., housekeeping genes, whose expression levels are known not to differ depending on the cancerous or non-cancerous state of the cell. Exemplary control genes include, but are not limited to, beta-actin, glyceraldehyde 3 phosphate dehydrogenase, and ribosomal protein P1.

When the expression level of LY6K gene is increased as compared to the normal control level, or is similar/equivalent to the cancerous control level, the subject may be diagnosed with cancer to be treated.

More specifically, the present invention provides a method of (i) diagnosing whether a subject has the cancer to be treated, and/or (ii) selecting a subject for cancer treatment, which method includes the steps of:

a) determining the expression level of LY6K in cancer cells or tissue(s) obtained from a subject who is suspected to have the cancer to be treated;

b) comparing the expression level of LY6K with a normal control level;

c) diagnosing the subject as having the cancer to be treated, if the expression level of LY6K is increased as compared to the normal control level; and d) selecting the subject for cancer treatment, if the subject is diagnosed as having the cancer to be treated, in step c).

Alternatively, such a method includes the steps of:

a) determining the expression level of LY6K in cancer cells or tissue(s) obtained from a subject who is suspected to have the cancer to be treated;

b) comparing the expression level of LY6K with a cancerous control level;

c) diagnosing the subject as having the cancer to be treated, if the expression level of LY6K is similar or equivalent to the cancerous control level; and d) selecting the subject for cancer treatment, if the subject is diagnosed as having the cancer to be treated, in step c).

In some embodiments, such a method may further comprise the step of identifying, after or before the steps a)-d) defined above, a subject having an HLA selected from the group consisting of HLA-DP5, HLA-DR15 and HLA-DR8. Cancer therapy according to the present invention is preferable for a subject that suffers from cancer overexpressing LY6K and has any one of HLA-DP5, HLA-DR15 and HLA-DR8. Methods for HLA typing are well known in the art. For example, PCR-based methods for typing HLA alleles are well known. Antibodies specific for each HLA molecule are also appropriate tools for identifying HLA types of a subject.

The present invention also provides a kit for determining a subject suffering from cancer that can be treated with the LY6K polypeptide of the present invention, which may also be useful in assessing and/or monitoring the efficacy of a particular cancer therapy, more particularly a cancer immunotherapy. Illustrative examples of suitable cancers include, but are not limited to, bladder cancer, cervical cancer, cholangiocellular carcinoma, esophageal cancer, gastric cancer, non-small cell lung cancer (NSCLC), osteosarcoma, pancreatic cancer, soft tissue tumor and head-and-neck malignant tumor (HNMT). More particularly, the kit preferably includes at least one reagent for detecting the expression of the LY6K gene in a subject-derived cancer cell, such reagent being selected from the group of:

(a) a reagent for detecting an mRNA of the LY6K gene;

(b) a reagent for detecting the LY6K protein; and (c) a reagent for detecting the biological activity of the LY6K protein.

Examples of reagents suitable for detecting an mRNA of the LY6K gene include nucleic acids that specifically bind to or identify the LY6K mRNA, such as oligonucleotides that have a complementary sequence to a portion of the LY6K mRNA. These kinds of oligonucleotides are exemplified by primers and probes that are specific to the LY6K mRNA. These kinds of oligonucleotides may be prepared based on methods well known in the art. If needed, the reagent for detecting the LY6K mRNA may be immobilized on a solid matrix. Moreover, more than one reagent for detecting the LY6K mRNA may be included in the kit.

On the other hand, examples of reagents suitable for detecting the LY6K protein include antibodies to the LY6K protein. The antibody may be monoclonal or polyclonal. Furthermore, any fragment or modification (e.g., chimeric antibody, scFv, Fab, F(ab')$_2$, Fv, etc.) of the antibody may be used as the reagent, so long as the fragment or modified antibody retains the binding ability to the LY6K protein. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of the antibodies to their targets are well known in the art, and any labels and methods may be employed for the present invention. Moreover, more than one reagent for detecting the LY6K protein may be included in the kit.

The kit may contain more than one of the aforementioned reagents. For example, tissue samples obtained from subjects without cancer or suffering from cancer, may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be retained in a container with a label. Suitable containers include bottles, vials, and test tubes. The containers may be formed from a variety of materials, such as glass or plastic.

As an embodiment of the present invention, when the reagent is a probe against the LY6K mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of a test sample, the number of sites displaying a detectable signal provides a quantitative indication of the amount of LY6K mRNA present in the sample. The detection sites may be configured in any suitably detectable shape and are typically in the shape of a bar or dot spanning the width of a test strip.

The kit of the present invention may further include a positive control sample or LY6K standard sample. The positive control sample of the present invention may be prepared by collecting LY6K positive samples and then assaying their LY6K levels. Alternatively, a purified LY6K protein or polynucleotide may be added to cells that do not express LY6K to form the positive sample or the LY6K standard sample. In the present invention, purified LY6K may be a recombinant protein. The LY6K level of the positive control sample is, for example, more than the cut off value.

X. Antibodies:

The present invention further provides antibodies that bind to the peptide of the present invention.

Preferred antibodies specifically bind to the peptide of the present invention and will not bind (or will bind weakly) to other peptides. Alternatively, antibodies bind to the peptide of the invention as well as the homologs thereof. Antibodies against the peptide of the invention can find use in cancer diagnostic and prognostic assays, as well as imaging methodologies. Similarly, such antibodies can find use in the treatment, diagnosis, and/or prognosis of other cancers, to the extent LY6K is also expressed or over-expressed in a cancer patient. Moreover, intracellularly expressed antibodies (e.g., single chain antibodies) may therapeutically find use in treating cancers in which the expression of LY6K is involved, examples of which include, but are not limited to, bladder cancer, cervical cancer, cholangiocellular carcinoma, esophageal cancer, gastric cancer, non-small cell lung cancer (NSCLC), osteosarcoma, pancreatic cancer, soft tissue tumor and head-and-neck malignant tumor (HNMT).

The present invention also provides various immunological assay for the detection and/or quantification of LY6K protein (SEQ ID NO: 8) or fragments thereof including a polypeptide composed of amino acid sequences selected from among SEQ ID NOs: 1 and 2. Such assays may include one or more anti-LY6K antibodies capable of recognizing and binding a LY6K protein or fragments thereof, as appropriate. In the present invention, anti-LY6K antibodies binding to LY6K polypeptide preferably recognize a polypeptide composed of amino acid sequences selected from among SEQ ID NOs: 1 and 2, preferably to the exclusion of other peptides. The binding specificity of antibody can be confirmed with inhibition test. That is, when the binding between an antibody to be analyzed and full-length of LY6K polypeptide is inhibited under presence of any fragment polypeptides having an amino acid sequence selected from among SEQ ID NOs: 1 and 2, the antibody is deemed to "specifically bind" the fragment. In the context of the present invention, such immunological assays are performed within various immunological assay formats well known in the art, including but not limited to, various types of radio-immunoassays, immuno-chromatograph technique, enzyme-linked immunosorbent assays (ELISA), enzyme-linked immunofluorescent assays (ELIFA), and the like.

Related immunological but non-antibody assays of the invention may also include T cell immunogenicity assays (inhibitory or stimulatory) as well as MHC binding assays. In addition, immunological imaging methods capable of detecting cancers expressing LY6K are also provided by the invention, including, but not limited to, radioscintigraphic imaging methods using labeled antibodies of the present invention. Such assays can clinically find use in the detection, monitoring, and prognosis of LY6K expressing cancers, examples of which include, but are not limited to, bladder cancer, cervical cancer, cholangiocellular carcinoma, esophageal cancer, gastric cancer, non-small cell lung cancer (NSCLC), osteosarcoma, pancreatic cancer, soft tissue tumor and head-and-neck malignant tumor (HNMT).

The present invention also provides antibodies that binds to a peptide of the invention. An antibody of the invention can be used in any form, such as monoclonal or polyclonal antibodies, and include antiserum obtained by immunizing an animal such as a rabbit with the peptide of the invention, all classes of polyclonal and monoclonal antibodies, human antibodies and humanized antibodies produced by genetic recombination.

A peptide of the invention used as an antigen to obtain an antibody may be derived from any animal species, but preferably is derived from a mammal such as a human, mouse, or rat, more preferably from a human. A human-derived peptide may be obtained from the nucleotide or amino acid sequences disclosed herein. According to the present invention, complete and partial peptides of polypeptide of the present invention may serve as immunization antigens. Examples of suitable partial peptide include, for example, the amino (N)-terminal or carboxy (C)-terminal fragment of a peptide of the present invention.

Herein, an antibody is defined as a protein that reacts with either the full length or a fragment of a LY6K peptide. In a preferred embodiment, antibody of the present invention can recognize fragment peptides of LY6K having an amino acid sequence selected from among SEQ ID NOs: 1 and 2. Methods for synthesizing oligopeptide are well known in the arts. After the synthesis, peptides may be optionally purified prior to use as immunogen. In the present invention, the oligopeptide (e.g., 24- or 26 mer) may be conjugated or linked with carriers to enhance the immunogenicity. Keyhole-limpet hemocyanin (KLH) is well known as the carrier. Method for conjugating KLH and peptide are also well known in the arts.

Alternatively, a gene encoding a peptide of the invention or fragment thereof may be inserted into a known expression vector, which is then used to transform a host cell as described herein. The desired peptide or fragment thereof may be recovered from the outside or inside of host cells by any standard method, and may subsequently be used as an antigen. Alternatively, whole cells expressing the peptide or their lysates or a chemically synthesized peptide may be used as the antigen.

Any mammalian animal may be immunized with the antigen, though preferably the compatibility with parental cells used for cell fusion is taken into account. In general, animals of Rodentia, Lagomorpha or Primate family may be used. Animals of the family Rodentia include, for example, mouse, rat and hamster. Animals of the family Lagomorpha include, for example, rabbit. Animals of the Primate family include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum may be examined by a standard method for an increase in the amount of desired antibodies.

Polyclonal antibodies against the peptides of the present invention may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum. Immunoglobulin G or M can be prepared from a fraction which recognizes only the peptide of the present invention using, for example, an affinity column coupled with the peptide of the present invention, and further purifying this fraction using protein A or protein G column.

To prepare monoclonal antibodies for use in the context of the present invention, immune cells are collected from the mammal immunized with the antigen and checked for the increased level of desired antibodies in the serum as described above, and are subjected to cell fusion. The immune cells used for cell fusion may preferably be obtained from spleen. Other preferred parental cells to be fused with the above immunocyte include, for example, myeloma cells of mammalians, and more preferably myeloma cells having an acquired property for the selection of fused cells by drugs. The above immunocyte and myeloma cells can be fused according to known methods, for example, the method of Milstein et al. (Galfre and Milstein, Methods Enzymol 73: 3-46 (1981)).

Resulting hybridomas obtained by cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution may be performed to screen and clone a hybridoma cell producing the desired antibody.

In addition to the above method, wherein a non-human animal is immunized with an antigen for preparing hybridoma, human lymphocytes such as those infected by EB virus may be immunized with a peptide, peptide expressing cells or their lysates in vitro. Then, the immunized lymphocytes may be fused with human-derived myeloma cells that are capable of indefinitely dividing, such as U266, to yield a hybridoma producing a desired human antibody that is able to bind to the peptide can be obtained (Unexamined Published Japanese Patent Application No. Sho 63-17688).

The obtained hybridomas may then be subsequently transplanted into the abdominal cavity of a mouse and the ascites extracted. The obtained monoclonal antibodies can be purified by, for example, ammonium sulfate precipitation, a protein A or protein G column, DEAE ion exchange chromatography or an affinity column to which the peptide of the present invention is coupled. An antibody of the present invention can be used not only for purification and detection of a peptide of the present invention, but also as a candidate for agonists and antagonists of a peptide of the present invention. Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides for recombinant antibodies prepared as described above.

An antibody of the present invention may be a fragment of an antibody or modified antibody, so long as it binds to one or more of the peptides of the invention. For instance, the antibody fragment may be Fab, F(ab')$_2$, Fv or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, including the complementarity determining region (CDR) derived from nonhuman antibody, the frame work region (FR) and the constant region derived from human antibody. Such antibodies can be prepared according to known technology.

Humanization can be performed by substituting rodent CDRs or CDR sequences for the corresponding sequences of a human antibody (see, e.g., Verhoeyen et al., Science 239:1534-1536 (1988)). Accordingly, such humanized antibodies are chimeric antibodies, wherein substantially less than an intact human variable domain has been substituted by the corresponding sequence from a non-human species.

Fully human antibodies including human variable regions in addition to human framework and constant regions can also be used. Such antibodies can be produced using various techniques known in the art. For example, in vitro methods involve use of recombinant libraries of human antibody fragments displayed on bacteriophage (e.g., Hoogenboom & Winter, J. Mol. Biol.

227:381 (1991). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584; 5,545,807; 5,545,806; 5,569,825; 5,625,126; 5,633,425; 5,661,016.

Antibodies obtained as above may be purified to homogeneity. For example, the separation and purification of the antibody can be performed according to the separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS and Sepharose F.F. (Pharmacia).

Examples of suitable chromatography techniques, with the exception of affinity chromatography, include, for example, ion-exchange chromatography, hydrophobic chromatography, gel filtration, reverse phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the invention. In ELISA, the antibody of the present invention is immobilized on a plate, a peptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the peptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of the peptide of the invention, by exposing the antibody of the invention to a sample assumed to contain the peptide of the invention, and detecting or measuring the immune complex formed by the antibody and the peptide. Because the method of detection or measurement of the peptide according to the invention can specifically detect or measure a peptide, the method can find use in a variety of experiments in which the peptide is used.

XI. Vectors and Host Cells

The present invention also provides for vectors and host cells into which a nucleotide encoding the peptide of a present invention is introduced. A vector of the present invention finds utility as a carrier of nucleotides, especially a DNA, of the present invention in host cell, to express the peptide of the present invention, or to administer the nucleotide of the present invention for gene therapy.

When E. coli is selected as the host cell and the vector is amplified and produced in a large amount in E. coli (e.g., JM109, DH5 alpha, HB101 or XL1Blue), the vector should have an "ori" suitable for amplification in E. coli and a marker gene suited for selecting transformed E. coli (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc., can be used. In addition, pGEM-T, pDIRECT and pT7 can also be used for subcloning and extracting cDNA as well as the vectors described above. When a vector is used to produce the protein of the present invention, an expression vector can find use. For example, an expression vector to be expressed in E. coli should have the above characteristics to be amplified in E. coli. When E. coli, such as JM109, DH5 alpha, HB101 or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter or the like, that can efficiently express the desired gene in *E. coli*. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for peptide secretion. An exemplary signal sequence that directs the peptide to be secreted to the periplasm of the *E. coli* is the pelB signal sequence (Lei et al., J Bacteriol 169: 4379 (1987)). Means for introducing of the vectors into the target host cells include, for example, the calcium chloride method, and the electroporation method.

In addition to *E. coli*, for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "*Pichia* Expression Kit" (Invitrogen), pNV11, SP-Q01) and expression vectors derived from *Bacillus subtilis* (e.g., pPL608, pKTH50) can be used for producing the polypeptide of the present invention.

In order to express the vector in animal cells, such as CHO, COS or NIH3T3 cells, the vector should carry a promoter necessary for expression in such cells, for example, the SV40 promoter (Mulligan et al., Nature 277: 108 (1979)), the MMLV-LTR promoter, the EF1 alpha promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

Hereinafter, the present invention is described in more detail with reference to specific Examples. However, while the following materials, methods and examples may serve to assist one of ordinary skill in making and using certain embodiments of the present invention, there are only intended to illustrate aspects of the present invention and thus in no way to limit the scope of the present invention. As one of ordinary skill in the art will readily recognize, methods and materials similar or equivalent to those described herein can be used in the practice or testing of the present invention.

EXAMPLES

Materials and Methods

Patients and Clinical Study.

Two phase I clinical trials of peptide-based cancer immunotherapy were reviewed and approved by the Institutional Review Board of Kumamoto University, Kumamoto, Japan (approval no. 841 and 1124). All patients suffered from head and neck cancer were selected on the basis of HLA-A24 possession after taking written informed consents. Tumor stage and grading were determined according to the International Union against cancer (UICC) clarification. The patients suffered from inoperable advanced head and neck cancer with recurrent or metastatic tumors who had been resistant to standard therapy were enrolled in one trial (841). The patients suffered from operable advanced head and neck cancer were enrolled in another trial (1124). These patients in this trial (1124) had been treated with postoperative peptide-vaccine immunotherapy. The patients suffered from inoperable advanced HNMT with recurrent or metastatic tumors and were resistant to standard therapy; they were enrolled in the trial under University Hospital Medical Information Network Clinical Trials Registry (UMIN-CTR) number 000008379 (CTR-8379). HNMT patients with radical resection were enrolled in the trial under UMIN-CTR number 000008380 (CTR-8380). In the latter trial, HNMT patients were treated with postoperative peptide vaccine combined with S-1, ifosfamide, or doxorubicin. The vaccination cocktail consists of 3 synthetic short peptides (SPs) recognized by HLA-A24-restricted CTL and derived from CDCA1 (CDCA1-A24 (56-64)), KOC1 (KOC1-A24 (508-516)) and LY6K (LY6K-A24 (177-186) (Suda T, et al. Cancer Sci 2007.). Peptides (1 mg each) are emulsified in 500 micro-L Montanide ISA51 and injected subcutaneously (s.c.) on day 0, 7, 14, 28, 42, 56, 63 and 70, and then monthly until the tumor progression or toxicity are observed. These clinical trials and study analysis are still ongoing. Blood samples were collected from 23 patients who took part in these trials, and the immune responses of Th cells reactive to LY6K-derived peptides were investigated.

Cell Lines and Antibodies.

C1R-A2402 cells, an HLA-A24 transfectant of human B lymphoblastoid cell line C1R expressing a trace amount of intrinsic HLA class I molecule (Karaki S, et al. Immunogenetics 1993; 37: 139-42.) were a generous gift from Dr. Masafumi Takiguchi (Kumamoto University, Kumamoto, Japan). As antigen presenting cells (APCs), a mouse fibroblast cell line, L-cell, which have genetically been engineered to express either DR4 (DRB1*04:05); L-DR4, DR8 (DRB1*08:03); L-DR8, DR15 (DRB1*15:02); L-DR15 or DP5 (DPB1*05:01); L-DP5 were used.

Prediction by an Algorism of HLA Class II-Binding Peptides

To predict potential promiscuous HLA-DR and -DP binding human LY6K-derived peptides, the amino acid sequence of the human LY6K protein was analyzed using a computer algorithm (IEBD analysis resource, consensus method, http://tools.immuneepitope.org/analyze/html/mhc_II_binding.html) (Wang P, et al. BMC Bioinformatics; 11: 568. Wang P, et al. PLoS Comput Biol 2008; 4: e1000048.). The program analyzed 15 amino acid-long sequences offset encompassing the entire protein. A 20 amino acids-long peptide that have overlapping high consensus percentile ranks for multiple HLA-class II molecules encoded for by DRB1*09:01 or DRB1*15:02 alleles, and that naturally include LY6K-derived 10-mer CTL epitope was selected and synthesized to identify promiscuous helper T cell epitopes containing CTL epitopes (Harao M, et al. Int J Cancer 2008; 123: 2616-25.). Another 24 amino acids-long LY6K-derived LP was also synthesized that have overlapping high consensus percentile ranks for multiple HLA-class II molecules encoded for by DPB1*05:01, DRB1*08:03, DRB1*09:01 or DRB1*15:02, but doesn't include CTL epitope.

Synthetic Peptides and Recombinant Proteins

The human LY6K-derived short peptide (SP) that bind to HLA-A24, LY6K-A24 (177-186), RYCNLEGPPI (SEQ ID NO: 3) was synthesized (purity>95%, Biomatik, Canada). Two LP, LY6K (119-142), KWTEPYCVIAAVKIFPRFFM-VAKQ (SEQ ID NO: 1); LY6K (172-191) KCCKIRYCN- LEGPPINSSVF (SEQ ID NO: 2), were synthesized (purity>90%) and tested for their capacity to stimulate LY6K-specific human CD4+ T cells. A HIV peptide that binds to HLA-A24 (HIV-A24, RYLRDQQLL) (SEQ ID NO: 4) was used as negative control SP (Tomita Y, et al. Cancer Sci; 102: 697-705. Tomita Y, et al. Cancer Sci; 102: 71-8.). A EBNA (Epstein-Barr virus nuclear antigen)-derived LP that binds to DP5, EBNA-DP5 (FLQTHIFAEVLKDAIKDL) (SEQ ID NO: 5) and promiscuous HIV-derived LP were used as a negative control LP (Fujiki F, et al. J Immunother 2007; 30: 282-93.). Peptides were dissolved in dimethyl-sulfoxide at the concentration of 10 micro-g/microL. The recombinant whole LY6K and CDCA1 protein were expressed by *Escherichia coli* BL21 with a pET28a vector (Novagen). The CDCA1 protein was used as a control. Each recombinant protein was purified and assessed by SDS-PAGE.

Generation of TAAs-Specific CD4+ T Cell Lines from Healthy Donors

The research protocol for collecting and using peripheral blood mononuclear cells (PBMC) from healthy donors was approved by the Institutional Review Board of Kumamoto University. The blood samples were obtained from nine healthy donors after receiving their written informed consents. The HLA-A, DRB1 and DPB1 alleles of the healthy donors investigated in this study are determined by DNA typing of HLA genetic variations with polymerase chain reaction and allele-specific probe hybridization, and described in Table 1. PBMCs from healthy volunteers and patients were isolated as described previously (Inoue M, et al. Int J Cancer; 127: 1393-403.). CD4+ T cells were purified from PBMC by positive selection using magnetic microbeads coupled with anti-CD4 monoclonal antibody (Miltenyi Biotec, Auburn, Calif., USA). Monocyte-derived dendritic cell (DC) was generated from CD14+ cells by in vitro culture as described previously (Harao M, et al. Int J Cancer 2008; 123: 2616-25.) and used as antigen-presenting cell (APC) to induce TAA-specific CD4+ T cells. DCs ($1\times10^4$/well) were pulsed with 10 microg/ml LP for 3 h and irradiated (45 Gy), and then mixed with autologous CD4+ T cells ($3\times10^4$/well) in 200 micro-L of AIM-V supplemented with 5% human decomplemented plasma in each well of a 96-well, flat-bottomed culture plates. After 7 days, half of the medium was removed from each culture, and then the culture was added fresh medium (100 micro-L/well) containing irradiated (50 Gy) autologous PBMCs ($1\times10^5$) pulsed with peptide (10 micro-g/ml) and 5 ng/ml human recombinant (hr) IL-7. Two days after the second stimulation with peptide, hr IL-2 was added to each well at final concentration of 10 IU/ml. One week later, the stimulated CD4+ T cells in each well were analyzed for specificity in interferon (IFN)-gamma enzyme-linked immunospot (ELISPOT) assays. The T cells showing a specific response to the cognate peptide were transferred to 24-well plate and restimulated at weekly intervals with irradiated autologous PBMCs ($1\times10^6$/well) pulsed with the peptide (10 micro-g/ml) in medium supplemented with 10 IU/ml hr IL-2 and 5 ng/ml hr IL-7.

TABLE 1

HLA-A, -DR and -DP genotypes of healthy donors

| | HLA-A genotype | HLA-DRB1 genotype | HLA-DPB1 genotype |
|---|---|---|---|
| Donor HDL1 | A*02:01/24:02 | DRB1*04:05/— | DRB1*05:01/— |
| Donor HDL2 | A*11:01/31:01 | DRB1*08:03/15:02 | DRB1*02:01/09:01 |
| Donor HDL3 | A*24:02/— | DRB1*08:02/15:02 | DRB1*05:01/09:01 |
| Donor HDL4 | A*24:02/31:01 | DRB1*08:03/14:05 | DRB1*02:02/05:01 |
| Donor HDL5 | A*02:01/02:06 | DRB1*04:05/09:01 | DRB1*02:01/04:02 |
| Donor HDL6 | n.t. | DRB1*04:06/08:03 | DRB1*02:01/04:02 |
| Donor HDL7 | A*26:01/33:03 | DRB1*04:05/13:02 | DRB1*04:01/09:01 |
| Donor HDL8 | A*26:01/— | DRB1*04:10/08:02 | DRB1*02:01/05:01 |
| Donor HDL9 | A*31:01/33:03 | DRB1*09:01/13:02 | DRB1*03:01/04:01 |

HLA, human histocompatibility leukocyte antigen.

Assessment of T Cell Responses to Peptides

The immune response of Th cells to APCs pulsed with peptides were assessed by IFN-gamma ELISPOT assays (Human IFN-gamma ELISPOT kit, BD Biosciences) as described previously (Tomita Y, et al. Cancer Sci; 102: 697-705.). Briefly, the frequency of peptide-specific CD4+ T cells producing IFN-gamma per $3\times10^4$ bulk CD4+ T cells upon stimulation with peptide-pulsed PBMCs ($3\times10^4$ cells/well), or $1\times10^4$ bulk CD4+ T cells upon stimulation with peptide-pulsed HLA-DR or DP-expressing L-cells ($5\times10^4$/well) was analyzed. To determine restriction HLA molecules involved in antigen presentation, blocking of antigen-induced IFN-gamma production was investigated by adding anti-HLA-DR mAb (L243, Biolegend), anti-HLA-DP mAb, (B7/21, abcam), anti-human HLA-DQ mAb (SPV-L3, abcam), or anti-HLA class I mAb, (W6/32, abcam). All mAbs were used at a final concentration of 5 micro-g/ml. Cells cultured with HIV-derived peptides were used as negative control. Cells cultured with PMA (100 ng/ml; Sigma-Aldrich) and ionomycin (500 ng/ml; Sigma-Aldrich) were used as positive controls. All assessments of IFN-gamma ELISPOT assays were carried out in duplicate or triplicate, and results corresponded to mean values.

Cytokine Assays

T cells ($1\times10^4$/well) were cultured with L-DP5 ($5\times10^4$/well) in the presence of LY6K (119-142) in 96-well culture plate. After 20 h, culture supernatants were collected and cytokine (IFN-gamma, GM-CSF, TNF-alpha, MIP1beta, IL-2, IL-4, IL-17) level was measured using the Bio-Plex system (Bio-Rad) according to manufacturers' instructions.

LY6K (119-142) LP-specific bulk Th cells ($3\times10^4$ cells/well) and the LY6K (172-191) LP-specific Th cell clone (Th-clone, $1\times10^4$ cells/well) were cultured with autologous PBMCs ($3\times10^4$ cells/well) in the presence of cognate peptide in 96-well culture plates. After 24 h, culture supernatants were collected and cytokine (IL-2, IFN-gamma, GM-CSF, TNF-alpha, and MIP1beta) levels were measured using the Bio-Plex system (Bio-Rad) according to manufacturer's instructions.

CD107a Mobilization Assay

To identify degranulating CD4+ T lymphocytes stimulated with a LP, the CD107a exposed on the cell surface was analyzed by flow cytometry. (Rubio V, et al. Nat Med 2003; 9: 1377-82. Betts M R, et al. J Immunol Methods 2003; 281: 65-78.) Briefly, a CD107a mobilization assay was performed as described previously. (Tomita Y, et al. Cancer Sci 2011; 102(1):71-8.) The LY6K-derived peptide or control peptide (1 micro-g/ml) was added as a stimulant, and FITC-labeled anti-human CD107a mAb or FITC-labeled isotype control mouse IgG1 and monensin were added to each well. Cells were cultured for 5 h at 37 degrees C. After culture, the peptide-stimulated Th cells or CTLs were stained with PE-conjugated anti-human CD4 antibody (eBioscience, San Diego, Calif.), and analyzed by flow cytometry (FACScan; BD Biosciences).

Stimulation of PBMC with the LY6K (172-191) Long Peptide

To assess the induction of LY6K-A24 (177-186) SP-specific CTLs from HLA-A24-positive donors by the simulation with LY6K (172-191) LP in vitro, PBMC ($2\times10^6$/well of 24-well plates) were incubated with LY6K (172-191) LP (7 microM) for 2 weeks without addition of any cytokine. On day 0 and 7, LY6K (172-191) LP (7 microM) was added, then on day 14 of in vitro stimulation with LY6K (172-191) LP, the cells were harvested, stained with a PE-labeled tetramer of the HLA-A24 (A*24:02)/LY6K-A24 (177-186) complex in combination with a FITC-labeled anti-human CD8 mAb, and analyzed by flow cytometry.

Propagation of LY6K-A24 (177-186) SP Specific CTLs by Stimulation with LY6K-LPs in HNMT Patients PBMCs from 11 HNMT patients vaccinated with LY6K-A24 (177-186) SP were cultured with a mixture of LY6K (119-142) LP and LY6K (172-191) LP (10 micro-g/mL each) in a 24-well plate ($2\times10^6$/well); rhIL-2 (20 IU/mL) and rhIL-7 (5 ng/mL) were added on day 0 and day 2. On day 0 (ex vivo) and day 7, the PBMCs were stained with a PE-labeled tetramer of the HLA-A*24:02/LY6K-A24 (177-186)-complex (MBL, Nagoya, Japan) with a FITC-labeled anti-human CD8 mAb.

In Vivo Cross-Priming Assay

HLA-A24 Tgm were kindly provided by Dr. F. A. Lemonnier (Jung K O, et al. J Virol; 86: 7616-24). For peptide vaccination, the mice were intradermally injected at the base of the tail with LY6K (172-191) LP (100 micro-g/mouse) solution emulsified in IFA at 7-day intervals. Seven days after the second vaccinations with LY6K (172-191) LP, mice were sacrificed to obtain inguinal lymphocytes and CD8$^+$ T cells were positively isolated with magnetic microbeads. The number of IFN-gamma producing CD8$^+$ T cells ($3\times10^5$/well) upon stimulation with LY6K-A24 (177-186) SP or HIV-A24 SP-pulsed C1R-A2402 cells ($2\times10^4$/well) was counted by ELISPOT assay.

HLA-A24 (HHH) transgenic mice (Tgm) were kindly provided by Dr. F. A. Lemonnier (Jung K O, et al. J Virol; 86: 7616-24). Mice were intradermally injected at the base of the tail with LY6K (172-191) LP solution (100 micro-g/mouse) emulsified in incomplete Freund's adjuvant (IFA), third times at 7-day intervals. Seven days after the third vaccination with LY6K (172-191) LP, CD8$^+$ T cells were isolated from inguinal lymph nodes by positive selection with magnetic microbeads (Miltenyi Biotec, Auburn, Calif., USA). The number of IFN-gamma producing CD8$^+$ T cells ($1\times10^5$ cells/well) in response to stimulation with LY6K-A24 (177-186) SP-pulsed BM-DCs ($2\times10^4$ cells/well) was counted by ex vivo ELISPOT assay (Inoue M, et al. Immunol Lett 2009; 126:67-72; Harao M, et al. Int J Cancer 2008; 123:2616-25.).

Assessment of LY6K-Specific CD4$^+$ T Cell Responses in Head and Neck Cancer Patients Actively Immunized with the LY6K-Derived SP The PBMCs from cancer patients or healthy donors were cultured with 10 micro-g/ml of mixture of LY6K-derived LPs in a 24-well plate ($2\times10^6$/well) in AIM-V supplemented with 5% human decomplemented plasma and IL-7 and IL-2 were added at day 0 and day 2. After 1 week of cell culture, the PBMCs were collected and the presence of LY6K-specific T cells was measured by IFN-gamma ELISPOT assays. The short time cultured PBMCs ($1\times10^5$/well) were washed and cultured in anti-human IFN-gamma monoclonal antibody precoated ELISPOT plate with LY6K (172-191) or LY6K (119-142) LP in medium for 18 hours. Cells cultured with HIV-A24 were used as negative controls. The number of specific T cells expressed as spot-forming cells/$10^5$ cells was calculated after subtracting negative control values (background). For determination of HLA-class II-restriction, the following blocking antibodies specific to HLA-DR, HLA-DP, or HLA-class I were added in cell culture during the ELISPOT assay. Responses were evaluated to be positive when IFN-gamma were more than 10 and more than 2-fold the background. All the experiments in cancer patients were conducted in single well or duplicate wells. The ELISPOT assays on patients' cells were conducted in single, duplicate, or triplicate wells because of the limited number of available cells. And responses were evaluated to be positive when IFN-gamma were more than 15 and more than 2-fold the background. This study was conducted in a laboratory that operates under exploratory research principles, and was performed using investigative protocols. We acknowledge the recommendations of the Minimal Information About T-cell Assay (MIATA) reporting framework for human T-cell assays (Britten C M et al., Immunity 2012; 37:1-2.).

Tetramer Staining

Expression of LY6K-A24 (177-186) SP specific T cell receptor (TCR) was examined on a FACSCalibur (BD Biosciences) using a PE-labeled tetramer of the HLA-A*24: 02/LY6K-A24 (177-186) SP complex (MBL, Nagoya, Japan) according to the manufacturer's instructions. A PE-labeled tetramer of the HLA-A*24:02/HIV-A24 (RYL-RDQQLL: SEQ ID NO: 4) complex was used as a negative control.

In Vitro Cross-Presentation Assay

Induction of LY6K-A24 (177-186) SP-reactive CTLs from an HLA-A24$^+$ and HLA-DR15$^+$ HDL3 by stimulation with LY6K-A24 (177-186) SP was performed as described (Tomita Y, et al, Cancer Sci 2011; 102:71-8., Imai K, et al., Clin Cancer Res 2008; 14:6487-95.). Monocyte-derived DCs were generated from CD14$^+$ cells by in vitro culture, as described previously (Harao M, et al. Int J Cancer 2008; 123:2616-25.). Autologous immature DCs were kept alive or fixed for 3 min in 0.1% glutaraldehyde (Sigma-Aldrich), pulsed with LY6K-A24 (177-186) SP, LY6K (172-191)-LP, or control LP (16 micro-M each) for 3 h, and washed 3 times. OK432 (0.1 KE/mL) was added during and after the peptide pulse to induce the maturation of DCs. LY6K (119-142) LP, which does not include a known CTL-epitope, was used as a control LP. LY6K-A24 (177-186) SP-reactive bulk CTLs were added at a 2:1 ratio for 6 h in medium containing 10 micro g/mL brefeldin A (Sigma-Aldrich). IFN-gamma production by LY6K-A24 (177-186) SP-specific CTLs was measured by intracellular labeling. The cells were stained with a FITC-labeled anti-human IFN-gamma mAb (BioLegend) in combination with a PerCP-labeled anti-human CD8 mAb (BioLegend) and a PE-labeled LY6K-A24 (177-186) SP-specific tetramer.

Propagation of LY6K-A24 (177-186) SP Specific CTLs by Stimulation with LY6K (172-191)-LP in HNMT Patients PBMCs from 5 HNMT patients vaccinated with LY6K-A24 (177-186) SP were cultured with LY6K (172-191) LP (10 micro-g/mL each) in a 96-well plate ($1\times10^5$/well); rhIL-2 (20 IU/mL) and rhIL-7 (5 ng/mL) were added on day 0 and day 2. On day 0 (ex vivo) and day 7, the PBMCs were stained with a PE-labeled tetramer of the HLA-A*24:02/LY6K-A24 (177-186)-complex with a FITC-labeled anti-human CD8 mAb.

In Vitro Induction of LY6K-A24 (177-186) SP-Specific CTLs by Stimulation of PBMCs with LY6K (172-191)-LP To assess induction of LY6K-A24 (177-186) SP-specific CTLs from HLA-A24+ donors (HDL1, HDL3, and HDL4) by simulation with LY6K (172-191) LP in vitro, PBMCs ($2\times10^6$ cells/well of 24-well plates) were incubated with LY6K (172-191) LP (7 microM) for 2 weeks without addition of cytokines. On day 7, LY6K (172-191) LP (7 microM) was added, then on day 14 of in vitro stimulation with LY6K (172-191) LP, the cells were harvested and stained with a PE-labeled LY6K-A24 (177-186) SP-specific tetramer with a FITC-labeled anti-human CD8 mAb.

The Synergistic Effect of LY6K-LPs on Induction of LY6K-Specific CTLs

To test whether LY6K-LPs could enhance induction of LY6K-A24 (177-186) SP-specific CTLs. LY6K (119-142) LP-specific or LY6K (172-191) LP-specific bulk CD4+ T-cells ($1\times10^5$ cells/well, 48-well plates) and LY6K-A24 (177-186) SP-specific bulk CD8+ T-cells ($1\times10^5$ cells/well) derived from HDL3 were cultured with autologous DCs ($2\times10^4$ cells/well) in the presence of LY6K-A24 (177-186) SP (10 micro-g/mL), LY6K-A24 (177-186) SP+control LP (10 micro-g/mL), or LY6K-A24 (177-186) SP+LY6K-LP (10 micro-g/mL). After 1-week in vitro culture with peptides, the cultured cells were stained with LY6K-A24 (177-186) SP-specific tetramer.

Fresh PBMCs obtained from HNMT patients vaccinated with LY6K-A24 (177-186) SP were plated in a 96-well, round-bottomed culture plate ($1\times10^5$ cells/well), followed by addition of LY6K-A24 (177-186) SP alone (10 micro-g/mL), LY6K-A24 (177-186) SP+control LP (10 micro-g/mL), LY6K-A24 (177-186) SP+LY6K (119-142) LP (10 micro-g/mL), or LY6K-A24 (177-186) SP+LY6K (172-191) LP (10 micro-g/mL) in a final volume of 200 micro-L AIM-V supplemented with 5% human decomplemented plasma without addition of cytokines. On day 7 of culture, cells were stained with a LY6K-A24 (177-186)-specific tetramer.

Statistical Analysis

The data were compared by the Two-tailed Student's t-test (bar graphs), Fisher's exact probability test, or nonparametric Mann-Whitney U test. Differences with a P value of <0.05 were considered statistically significant for all tests.

Results

Prediction and Selection of Potential Promiscuous HLA Class II-Binding Peptides

To identify the potential promiscuous HLA-class II binding Th cell epitopes of LY6K, the present inventors first examined the amino acid sequence of LY6K using a computer algorithm as shown in FIG. 1A and Table 2 (Wang P, et al. BMC Bioinformatics; 11: 568. Wang P, et al. PLoS Comput Biol 2008; 4: e1000048.). Interestingly, the inventors found that one LY6K-derived peptide, LY6K (172-191), predicted to be a potent promiscuous HLA class II-binding peptide by the computer algorithm was very proximal to a CTL epitope, LY6K-A24 (177-186) (FIG. 1B). Therefore, the inventors selected and synthesized a candidate LP, LY6K (172-191) that have overlapping high consensus percentile ranks for multiple HLA-class II molecules HLA-DR9 (DRB1*09:01) and HLA-DR15, and include a natural 10-mer peptide recognized by HLA-A24-restricted CTLs (FIG. 1A and Table 2) for subsequent analyses. Another LP, LY6K (119-142) was also synthesized that don't include CTL epitope but have overlapping high consensus percentile ranks for multiple HLA-class II molecules, and assessed whether this LP was able to generate LY6K-specific Th cells.

TABLE 2

Algorithm scores of long peptides derived from LY6K

| Amino acid residues position of LY6K | Percentile Rank | | | |
|---|---|---|---|---|
| | HLA-DP5 (DPB1*05:01) | HLA-DR8 (DRB1*08:03) | HLA-DR9 (DRB1*09:01) | HLA-DR15 (DRB1*15:02) |
| 119-133 | 35.0 | 20.1 | 1.4 | 5.0 |
| 120-134 | 36.2 | 14.8 | 3.3 | 5.0 |
| 121-135 | 30.9 | 4.1 | 1.1 | 5.0 |
| 122-136 | 8.4 | 3.0 | 1.1 | 5.0 |
| 123-137 | 8.0 | 1.8 | 3.7 | 5.0 |
| 124-138 | 3.0 | 1.0 | 3.4 | 0.02 |
| 125-139 | 1.9 | 1.2 | 15.1 | 0.02 |
| 126-140 | 1.5 | 1.4 | 15.2 | 0.02 |
| 127-141 | 1.2 | 2.3 | 15.4 | 0.02 |
| 128-142 | 1.2 | 4.7 | 28.2 | 0.02 |
| 172-186 | 37.7 | 36.6 | 16.1 | 3.6 |
| 173-187 | 37.9 | 42.7 | 13.2 | 3.6 |
| 174-188 | 43.9 | 45.7 | 10.5 | 3.6 |
| 175-189 | 67.8 | 48.2 | 9.1 | 3.6 |
| 176-190 | 75.5 | 65.6 | 13.7 | 3.6 |
| 177-191 | 90.2 | 72.6 | 18.9 | 3.6 |
| 178-192 | 77.2 | 80.5 | 29.3 | 3.6 |

Peptide-binding algorithm scores for indicated HLA-class II molecules are shown for each 15 amino acid sequence of LY6K (119-142) and LY6K (172-192) peptides.

Identification of a LY6K-Derived and Promiscuous HLA Class II-Binding Th Cell Epitope Naturally Including a CTL Epitope The present inventors assessed whether these two selected synthetic LPs were able to generate LY6K-specific Th cells. CD4+ T cells isolated from PBMCs of 3 healthy donors were stimulated at weekly intervals with autologous DCs and PBMCs pulsed with LY6K (119-142) peptide. After at least three times stimulations, LY6K (119-142)-specific responses of the cultured CD4+ Th cells were examined by IFN-gamma ELISPOT assays. In an HLA-DP5-positive and DR4-positive healthy donor, the generated Th cell line produced a significant amount of IFN-gamma in response to LY6K (119-142) (FIG. 2A). To elucidate HLA-restriction of the Th cell lines, mAb specific to HLA-DR or HLA-DP were used. The IFN-gamma production of Th cell line in response to LY6K (119-142) was significantly reduced when HLA-DP-specific mAb was added, whereas HLA-DR-specific mAb showed no effect (FIG. 2A).

To further analyze the HLA-restriction, the inventors tested the reactivity of Th cells against peptide-pulsed L-DP5 or L-DR4 cells. Bulk LY6K (119-142)-specific Th cell lines generated from a DP5-positive healthy donor specifically recognized L-DP5 cells pulsed with LY6K (119-142), but not L-DR4 cells, an irrelevant peptide (EBNA-DP5)-pulsed L-DP5 cells, LY6K (119-142) peptide-pulsed L-DR4 cells. The IFN-gamma production of Th cell lines in recognition of LY6K (119-142)-pulsed L-DP5 cells were significantly inhibited by addition of anti-HLA-DP mAb, but not anti-HLA-class I mAb (FIG. 2B). These results clearly indicated that LY6K (119-142) was presented by HLA-DP5 in these Th cell lines.

To investigate whether LY6K (119-142) can bind other HLA class II molecules and induce Th cell responses, CD4+ T cells from two other healthy donors were stimulated with LY6K (119-142)-pulsed autologous DCs and PBMCs. The Th cell line generated from an HLA-DR8-positive donor-HDL2 specifically produced a significant amount of IFN-gamma in response to LY6K (119-142)-pulsed PBMCs and L-DR8 cells, but not LY6K (119-142)-pulsed L-DR15 cells. The IFN-gamma production of Th cell line in response to LY6K (119-142)-pulsed PBMCs or L-DR8 cells were significantly inhibited by addition of anti-HLA-DR mAb, but not the HLA-DP- or HLA-class I-specific mAbs (FIGS. 2A and B). These results clearly indicated that LY6K (119-142) was presented by HLA-DR8 in this T cell line.

The Th cell line generated from an HLA-DR15-positive donor-HDL3 by stimulations with LY6K (119-142) also specifically produced a significant amount of IFN-gamma in response to LY6K (119-142)-pulsed PBMCs and L-DR15 cells, but not LY6K (119-142)-pulsed or unpulsed L-DR8 cells. The IFN-gamma production of Th cell line against LY6K (119-142)-pulsed PBMCs or L-DR15 cells were significantly inhibited by addition of anti-HLA-DR mAb, but not the HLA-DP, -DQ or HLA-class I-specific mAbs (FIGS. 2A and B). These results clearly indicate that LY6K (119-142) was presented by HLA-DR15 in this T cell line.

Thus, the LY6K (119-142) has capability of binding to HLA-DP5, HLA-DR8 and HLA-DR15 molecules indicating that LY6K (119-142) is the Th cell epitope presented by promiscuous and frequent HLA class II molecules in the Japanese population.

Next, the present inventors assessed whether another peptide, LY6K (172-191) that contain an epitope recognized by HLA-A24-restricted CTL was able to generate specific Th1 cell. The CD4+ T cells of PBMCs from two healthy donors were stimulated with autologous DCs and PBMCs pulsed with LY6K (172-191).

Figure 3A:
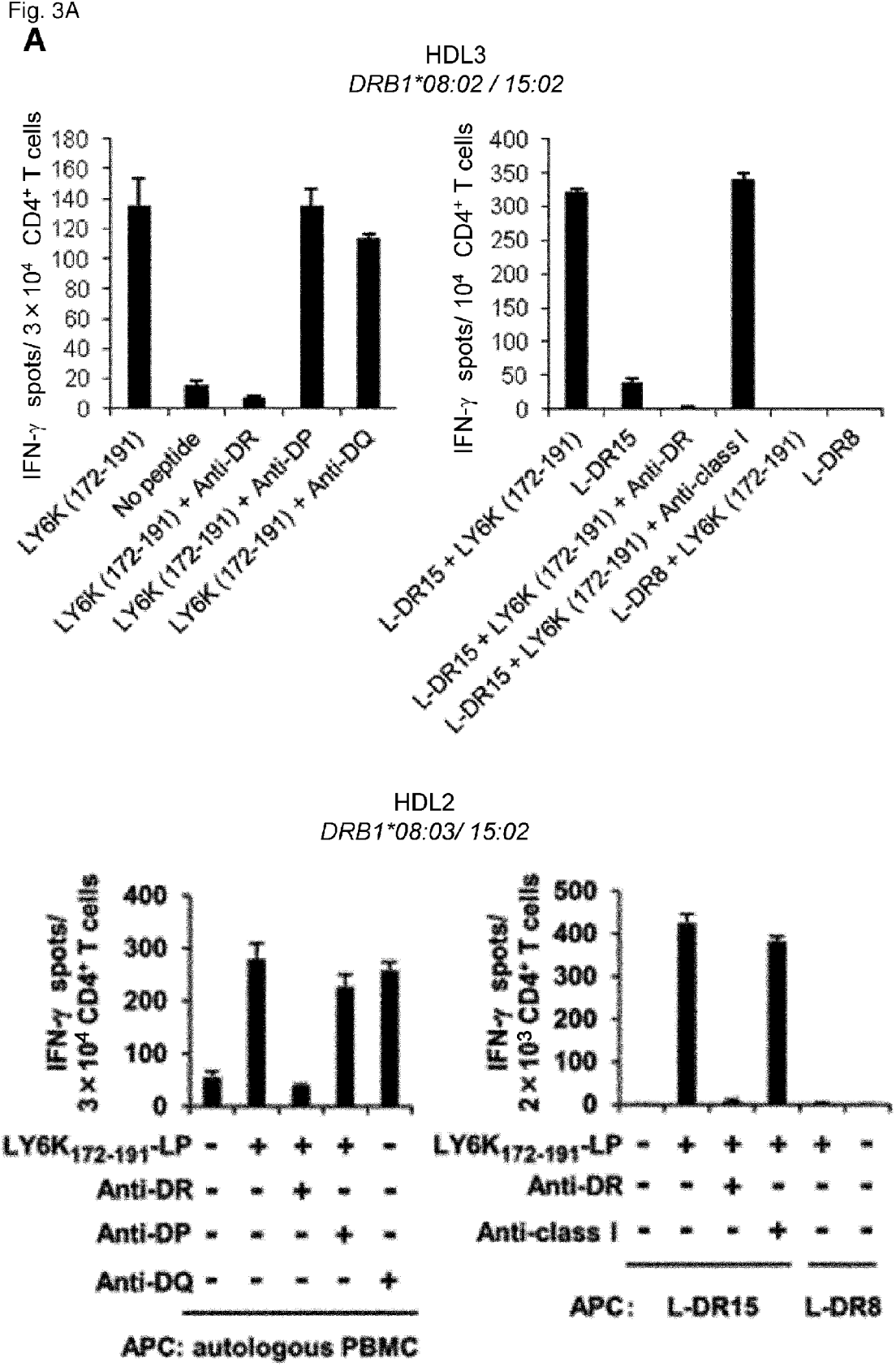

The Th cell line generated from an HLA-DR15-positive donor-HDL3 by stimulations with LY6K (172-191) specifically produced a significant amount of IFN-gamma in response to LY6K (172-191)-pulsed PBMCs and L-DR15 cells, but not LY6K (172-191)-pulsed or unpulsed L-DR8 cells. The IFN-gamma production of Th cell line against LY6K (172-191)-pulsed PBMCs or L-DR15 cells were significantly inhibited by addition of anti-HLA-DR mAb, but not the HLA-DP, -DQ or HLA-class I-specific mAbs (FIG. 3A upper panel). The Th cells generated from HLA-DR15+ donors (HDL2) produced a significant amount of IFN-gamma in response to LY6K (172-191) LP-pulsed PBMCs in an HLA-DR-dependent manner. The bulk Th cells specifically recognized L-DR15 cells pulsed with LY6K (172-191) LP in an HLA-DR-dependent manner (FIG. 3A Lower panel). These results clearly indicate that LY6K (172-191) was presented by HLA-DR15 in this T cell line.

Figure 3B:
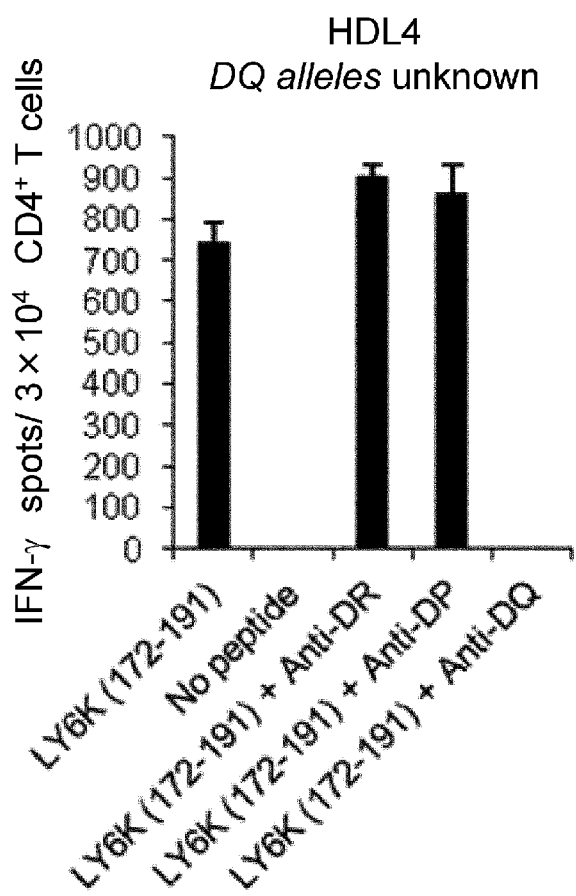

To investigate whether LY6K (172-191) can bind another HLA class II molecule and induce Th cell responses, CD4+ T cell from an HLA-DR15-negative healthy donor was stimulated with LY6K (172-191)-pulsed autologous DC and PBMC. The generated Th cells produced a significant amount of IFN-gamma in response to LY6K (172-191)-pulsed autologous PBMC, but not unpulsed PBMC (FIG. 3B). This IFN-gamma production of Th cell line was significantly inhibited by addition of anti-HLA-DQ mAb, but not anti-HLA-DR or anti-HLA-DP. These results indicated that this Th cell was restricted by HLA-DQ molecule.

A 25 amino acid (aa) long synthetic peptide extended in both the N- and C-termini of the natural corresponding proteins, LY6K (168-192), FFYLKCCKIRYCNLEGP-PIN-SSVFK (SEQ ID NO: 6), was synthesized and also tested for their capacity to stimulate LY6K-specific human CD4+ T cells. Interestingly, this extended LP could induced not only peptide-specific DQ-restricted Th cells but also DR-restricted Th cells in the same donor (FIG. 4). Thus, a longer peptide LY6K (168-192) may be able to more promiscuously induce Th cells than dose LY6K (172-191).

Taken together, these results presented here clearly demonstrate that two peptides, LY6K (119-142) and LY6K (172-191), have capability to stimulate HLA-DP5, -DR8, -DR15 and -DQ-restricted Th cells, suggesting that these peptides can be presented to Th cells by promiscuous HLA class II molecules and would be available for cancer immunotherapy of many patients.

LY6K (119-142) Peptide Stimulates Th1-Type CD4+ T Cells

To further characterize LY6K peptide-induced Th cells, the present inventors measured several cytokines in response to the stimulation of LY6K-specific bulk CD4+ Th cell line with cognate peptide by Bio-Plex system. LY6K-specific bulk Th line generated from the donor-HDL1 produced a large amount of IFN-gamma, TNF-alpha, GM-CSF and MIP-1beta and significantly produced IL-2, but less IL-4 and IL-17 by the restimulation with cognate peptide-pulsed L-DP5 indicating Th1 polarized characteristics of the Th cells induced by the LY6K peptide (FIG. 5A).

Figure 5B:
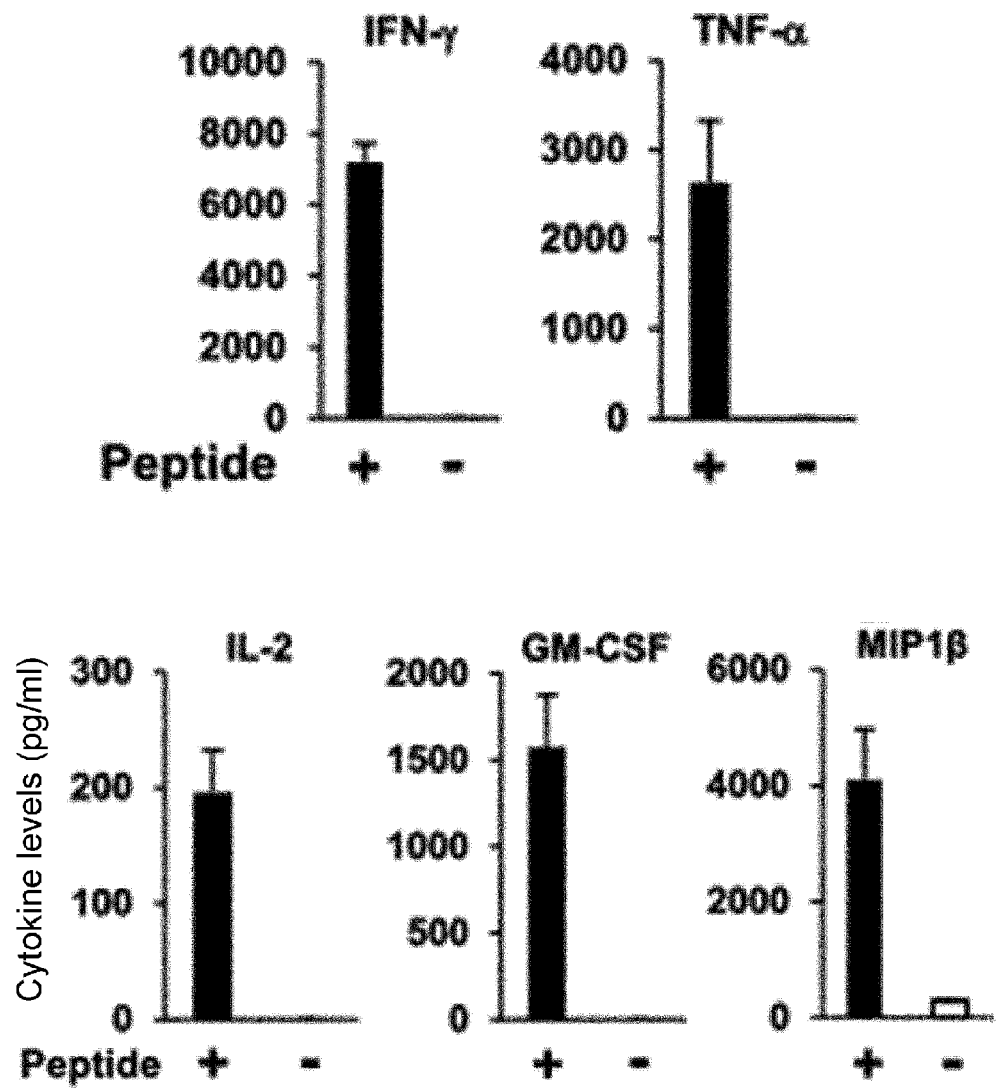

As shown in FIG. 5B, LY6K (172-191) LP-specific Th-clone from HDL4 produced a large amount of these cytokines after stimulation, suggesting LY6K (172-191) LP can induce multifunctional Th1 cells. Similar results were obtained from LY6K (172-191) LP-specific Th cells established from HDL3 (data not shown).

Interestingly, the cytotoxicity marker CD107a could also be detected on LY6K (119-142)-specific bulk Th cell line stimulated with cognate peptide (FIG. 5C Upper panel), as it was shown for antiviral CD4+ effectors and tumor-infiltrating lymphocytes (Casazza J P, et al. J Exp Med 2006; 203: 2865-77. Attig S, et al. Cancer Res 2009; 69: 8412-9. Widenmeyer M, et al. Int J Cancer; 131: 140-9.). In regard to LY6K (172-191) LP, the CD107a was also detected on the LY6K (172-191) LP-specific bulk Th1 cells (HDL4) stimulated with cognate peptides (FIG. 5C lower panel and data nor shown), as was previously demonstrated for antiviral CD4+ effectors and tumor-infiltrating lymphocytes (Casazza J P, et al., J Exp Med 2006; 203:2865-77; Attig S, et al., Cancer Res 2009; 69:8412-9; Widenmeyer M, et al., Int J Cancer 2012; 131:140-9; Martorelli D, et al., Int Rev Immunol 2010; 29:371-402.) Altogether, these data suggest that LY6K-specific Th1 cells can exert helper function and direct cytotoxic activity, which are both advantageous for cancer immunotherapy.

The LY6K (172-191) LP Stimulates the Expansion of LY6K-A24 (177-186) SP-Specific CD8$^+$ T Cells In Vitro and In Vivo.

The capacity of the LY6K (172-191) LP to stimulate the expansion of LY6K-A24 (177-186) SP-specific CD8$^+$ T cells was then examined. Twice stimulations of PBMC with 7 micro-M of the LY6K (172-191) LP induced an expansion of HLA-A24-restricted and LY6K-A24 (177-186) SP-specific CD8$^+$ T cells compared with the stimulations of PBMC with irrelevant peptide (FIG. 6A).

The present inventors also tested whether LY6K (172-191) LP could stimulate the expansion in vitro of LY6K-A24 (177-186) SP-specific CD8$^+$ T cells generated in a head and neck cancer patient actively immunized in vivo with the LY6K-A24 (177-186) SP. The presence of LY6K-A24 (177-186) SP-specific and HLA-A24-restricted CTL in PBMC ex-vivo isolated from this patient was detected by staining with a PE-labeled tetramer of the HLA-A24 (A*24:02)/LY6K-A24 (177-186)-complex (FIG. 6B, left). These PBMCs were cultured for a short period (one week) with LY6K (172-191) LP and the LY6K-A24 (177-186) SP-specific CD8$^+$ T cell was detected by the tetramer. As shown in FIG. 6B right, LY6K-A24 (177-186) SP-specific CTL was significantly expanded by short term in vitro stimulation with LY6K (172-191) LP.

Figure 6C:
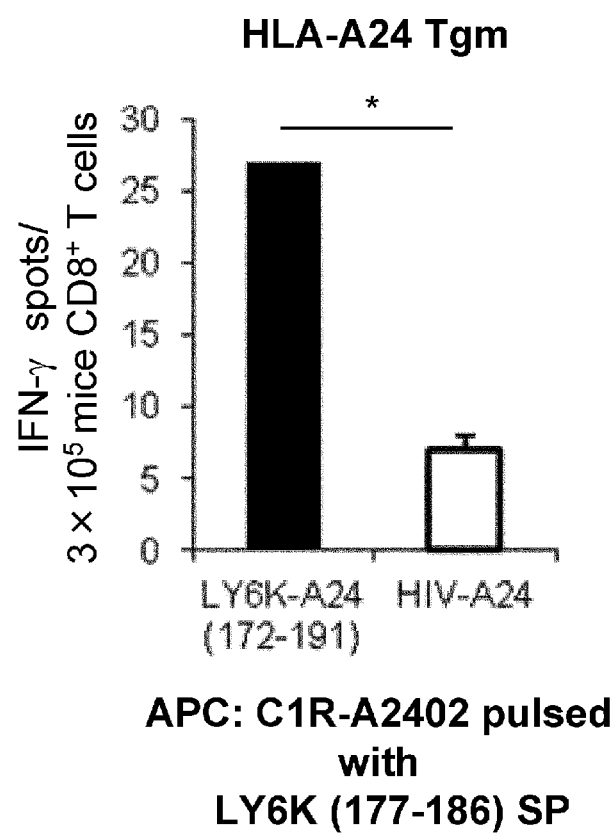

Next, the capacity of the LY6K (172-191) LP to stimulate LY6K-A24 (177-186) SP-specific CD8$^+$ T cell was examined in vivo. HLA-A24 Tgm were immunized twice at the base of the tail with LY6K (172-191) LP emulsified in IFA at 7-day intervals. Seven days after the second vaccinations with the LP, the number of IFN-gamma-secreting CD8$^+$ T cells in inguinal LN was determined by an ex vivo ELISPOT assay. As shown in FIG. 6C, the CD8$^+$ T cells stimulated by twice immunizations of HLA-A24 Tgm with LY6K (172-191) LP produced IFN-gamma specifically in response to re-stimulation with C1R2402 pulsed with the LY6K-A24 (177-186) SP, but not with C1R2402 pulsed with the irrelevant HIV-A24 peptide, suggesting that LY6K (172-191) LP induced a significant proportion of IFN-gamma-producing LY6K-A24 (177-186) SP-specific CTL possibly by cross-presentation in vivo in HLA-A24 Tgm.

Taken together, these results suggest that LY6K (172-191) LP can cross-prime LY6K-A24 (177-186) SP-specific CTLs both in vitro and in vivo.

Presence of LY6K-Specific T Cells in Head and Neck Cancer Patients Vaccinated with a LY6K-A24 (177-186) Short Peptide Recently, Godet Y. et al. reported the presence of spontaneous tumor-specific Th cell responses in lung cancer patients and the naturally occurring TAA-specific Th immune responses impact on clinical outcome (Godet Y, et al. Clin Cancer Res; 18: 2943-53.). Then, the inventors considered that LY6K-specific Th cell responses might be efficiently induced by active immunization of cancer patients with LY6K-derived CTL-epitope vaccine. To detect the antigen-specific responses in patients, PBMCs isolated from 7 head and neck cancer patients were collected, and the LY6K (119-142) LP-specific Th cells were detected by IFN-gamma ELISPOT assay. PBMC isolated from three healthy volunteers were used as control. Responses were considered positive when the number of IFN-gamma-secreting cells was at least 2-fold above the negative control. This experimental design enables us to measure LY6K-specific Th cell memory responses. As shown in FIG. 7A, LY6K (119-142) LP-specific memory immune responses were observed in 5 of 6 patients (83%), and LY6K (172-191) LP-specific memory immune responses were observed in all of patients (100%), whereas no specific IFN-gamma responses against LY6K were detected in 3 consecutive healthy donors and a non-vaccinated cancer patient (FIG. 7A). These IFN-gamma productions of Th cell lines were significantly inhibited by addition of anti-HLA-DR mAb, but not anti-HLA-DP, HLA-DQ or anti-HLA-class I (FIG. 7B). These results clearly indicated that these antigen-specific IFN-gamma productions were derived from CD4$^+$ cells restricted by HLA-DR molecule. The observations also showed that these two LY6K-derived LPs are naturally processed and presented to CD4$^+$ T cells in vivo in cancer patients.

Figure 8A:

Presence of LY6K-Specific Th Cells in HNMT Patients Before and after Vaccination with LY6K-A24 (177-186) SP The present inventors assessed Th cell responses specific for LY6K-LPs in peripheral blood from 21 HNMT patients who were enrolled in two peptide vaccine trials using LY6K-A24 (177-186) SP. The donor characteristics are summarized in FIG. 12. After 1 week of in vitro stimulation of PBMCs with LY6K-LPs, the frequency of individual LY6K-LPs-specific Th cells was detected by IFN-gamma ELISPOT assay (FIG. 8A). Responses were considered positive when the number of IFN-gamma-secreting cells was at least 2-fold above the negative control. It was found that LY6K-specific CD4$^+$ T-cell responses were present in HNMT patients. As shown in FIG. 8B, LY6K-LP-specific IFN-gamma production by Th cells was significantly inhibited by addition of the anti-HLA-class II mAbs, but not by the anti-HLA-class I mAb in 7 HNMT patients. Interestingly, HLA-class II alleles of LY6K (119-142) LP-specific HLA-DR or DQ-restricted Th cells in 3 HNMT patients were not shared by HLA-DR8 or -DR15 (FIG. 8B; LY6K (119-142) LP; HNMT31, 41, and 107). HLA-class II alleles of LY6K (172-191) LP-specific HLA-DR-restricted Th cells in 5 HNMT patients were not shared by HLA-DR15 (FIG. 8B; LY6K (172-191) LP; HNMT31, 41, 42, 107, and 108). These results suggest that LY6K (119-142) LP and LY6K (172-191) LP might encompass some HLA-class II-restricted Th cell epitopes which have not been identified by in vitro experiments in this study and could cover many cancer patients.

Figure 8E:
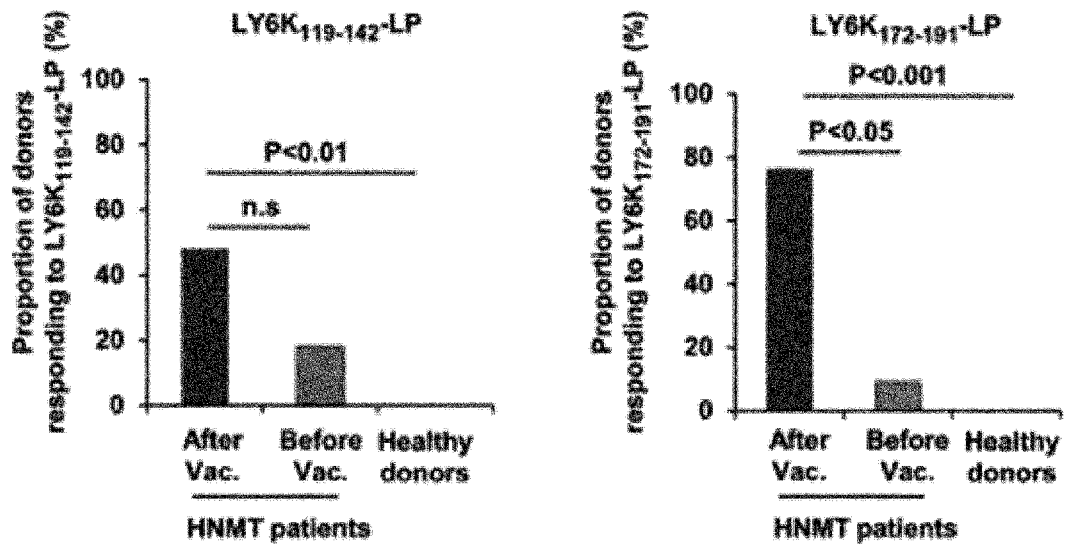
Figure 8F:
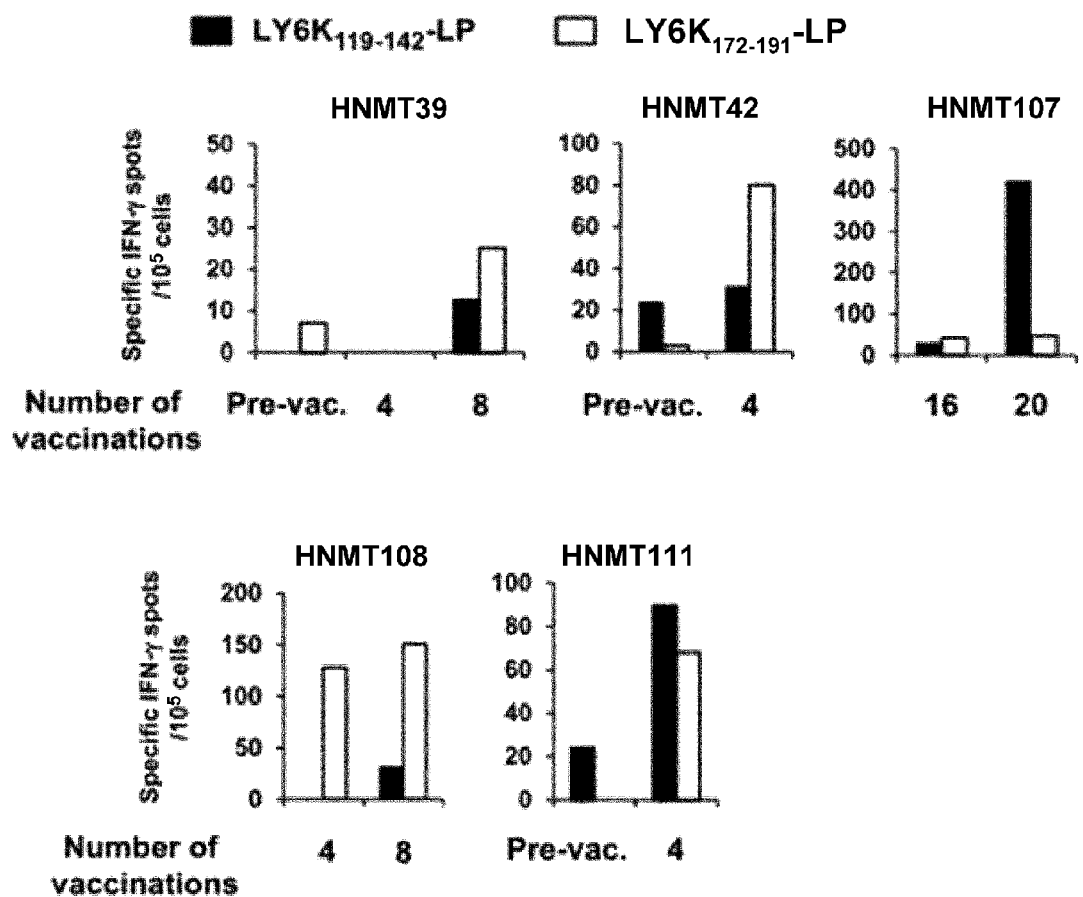
Figure 8G:
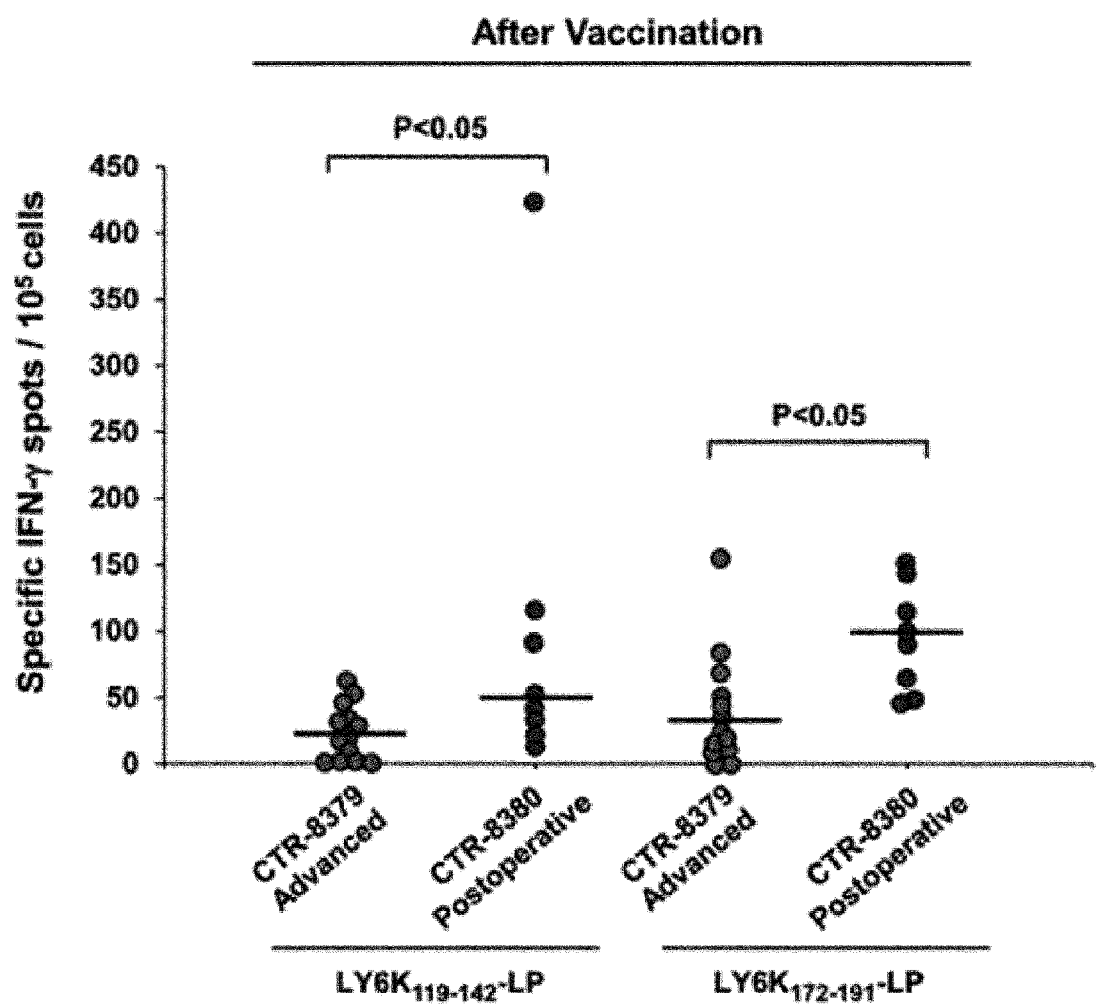

Significant frequency (LY6K (119-142) LP, 10 of 23, 44%; LY6K (172-191) LP, 16 of 23, 70%) of LY6K-LP-specific immune responses were detected in HNMT patients, whereas no specific IFN-gamma responses against LY6K-LPs were detected in the 9 healthy donors after short term in vitro stimulation with LY6K-LPs (FIG. 8C and FIG. 12). The numbers of specific spots against LY6K (119-142) LP and LY6K (172-191) LP in vaccinated patients were also significantly larger than in healthy donors (FIG. 8D). The number of LY6K (172-191) LP-specific spots in vaccinated patients was significantly larger than in HNMT patients before vaccination (FIG. 8D, right panel), although the number of LY6K (119-142) LP-specific spots in vaccinated patients was not significant compared with those in HNMT patients before vaccination (FIG. 8D, left panel). The frequency of LY6K (172-191) LP-specific immune response in HNMT patients after vaccination was significantly higher than those in HNMT patient before vaccination (FIG. 8E). LY6L-LP-specific responses were detected in some patients before vaccination but the frequencies were low (FIG. 12; LY6K (119-142) LP, 2 of 11, 18%; LY6K (172-191) LP, 1 of 11, 9%). Interestingly, specific responses to LY6K-LPs were elicited or augmented by repeated vaccinations (FIG. 8F). In a comparison of the numbers of LY6K-LP-specific IFN-gamma spots in vaccinated HNMT patients with advanced cancer (CTR-8379, n=13) and vaccinated HNMT patients receiving postoperative adjuvant immunotherapy (CTR-8380, n=8), the number of LY6K-LP-specific IFN-gamma spots in HNMT patients receiving postoperative adjuvant immunotherapy were significantly larger than those in vaccinated HNMT patients with advanced cancer (FIG. 8G). Taken together, these observations suggest that patients with HNMT are able to mount LY6K-specific CD4$^+$ T-cell responses.

LY6K-LPs Encompass Naturally Processed Th Cell Epitopes

The present inventors proceeded to assess whether DCs take up and process the LY6K protein to stimulate LY6K-LP specific Th cells. Autologous DCs loaded with recombinant LY6K protein were prepared and used as APCs in IFN-gamma ELISPOT assays (Tomita Y et al., Cancer Sci 2011; 102:71-8; Harao M et al., Int J Cancer 2008; 123:2616-25). An HLA-DP5-restricted LY6K (119-142) LP-reactive bulk Th cells efficiently recognized DC loaded with LY6K protein in an HLA-DP-dependent manner, but did not recognize control protein-loaded DC, indicating that LY6K (119-142) LP encompasses an epitope which is naturally processed and presented by HLA-DP5 molecules (FIG. 9A). HLA-DR15 or HLA-DQ-restricted LY6K (172-191) LP-specific Th-clones also recognized autologous DC loaded with LY6K protein, indicating that LY6K (172-191) LP encompass epitopes naturally processed and presented by HLA-DR15 and HLA-DQ molecules (FIG. 9B).

LY6K-A24 (177-186) SP-Specific CTLs were Stimulated Through Cross-Presentation of LY6K (172-191) LP In Vitro Next, the inventors tested whether LY6K (172-191) LP-pulsed DCs stimulate LY6K-A24 (177-186) SP-specific bulk CTLs through cross-presentation of LY6K (172-191) LP.

IFN-gamma production by LY6K-A24 (177-186) SP-specific CTLs was measured by intracellular labeling. Fixed DCs, unable to cross present but able to present LY6K-A24 (177-186) SP as efficiently as live DCs (FIG. 10A, Fixed DC+SP), were used to exclude or evaluate the contribution of exogenous presentation of LP degradation products in the T-cell response. LY6K (172-191) LP induced a significant proportion of IFN-gamma secreting tetramer$^+$ CD8$^+$ T-cells only when they were cross presented by unfixed DCs (DC+LP). LY6K (172-191) LP-pulsed fixed DCs could not stimulate LY6K-A24 (177-186)-specific CTLs, similar to control LP-pulsed unfixed DCs (Fixed DC+LP and DC+control LP).

The inventors assessed whether the LY6K (172-191) LP can induce expansion of LY6K-A24 (177-186) SP-specific bulk CTLs. LY6K-A24 (177-186) SP-specific bulk CTLs generated from purified CD8$^+$ T-cells of HLA-A24$^+$ HDL3 were restimulated with LY6K (172-191) LP-pulsed autologous DCs. As shown in FIG. 10B, the population of LY6K-A24 (177-186) SP-specific tetramer$^+$ CD8$^+$ cells was significantly expanded by stimulation with LY6K (172-191) LP-pulsed DCs on day 7, but decreased when the LY6K-A24 (177-186) SP-specific bulk CTLs were stimulated with control-LP-pulsed DCs. These results suggest that the expansion of LY6K-A24 (177-186) SP-specific CTLs were induced by cross-presentation of LY6K (172-191) LP by DCs.

Figure 10C:
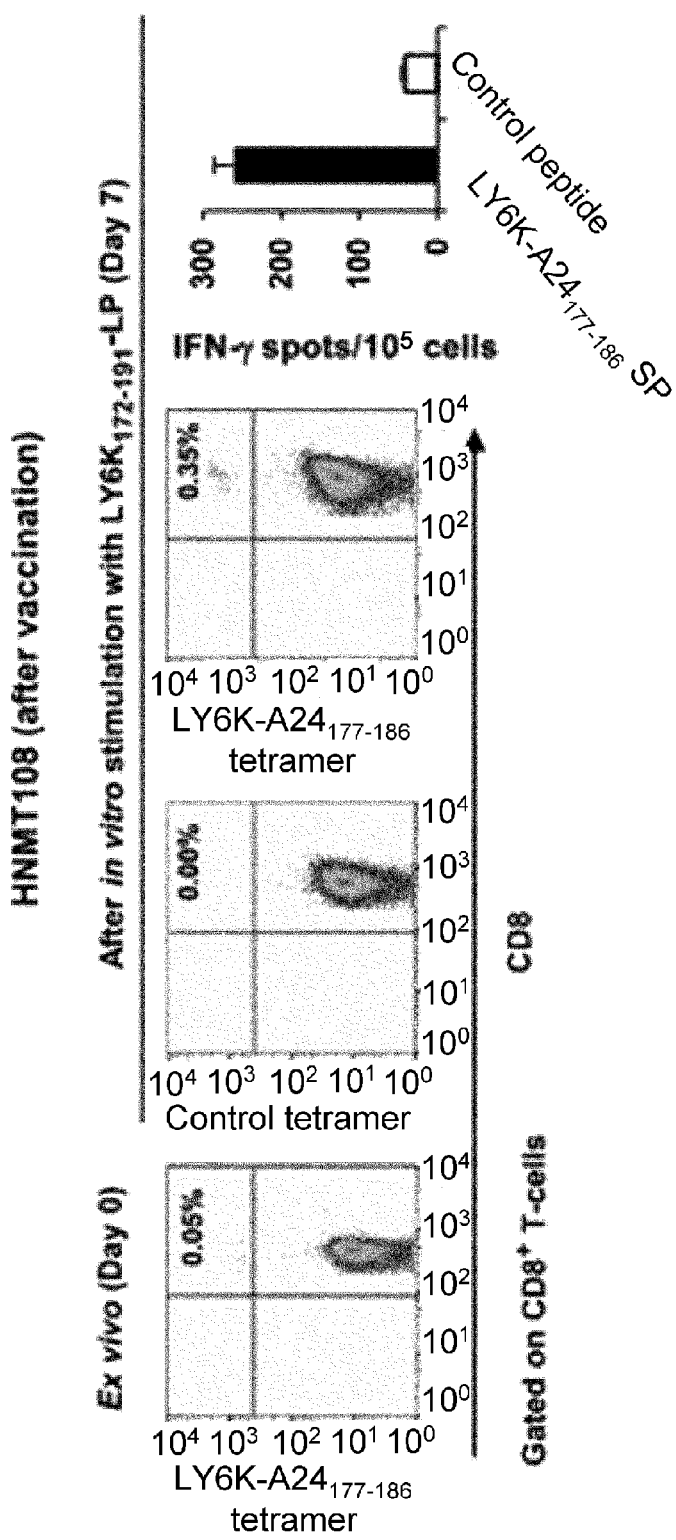
Figure 10D:
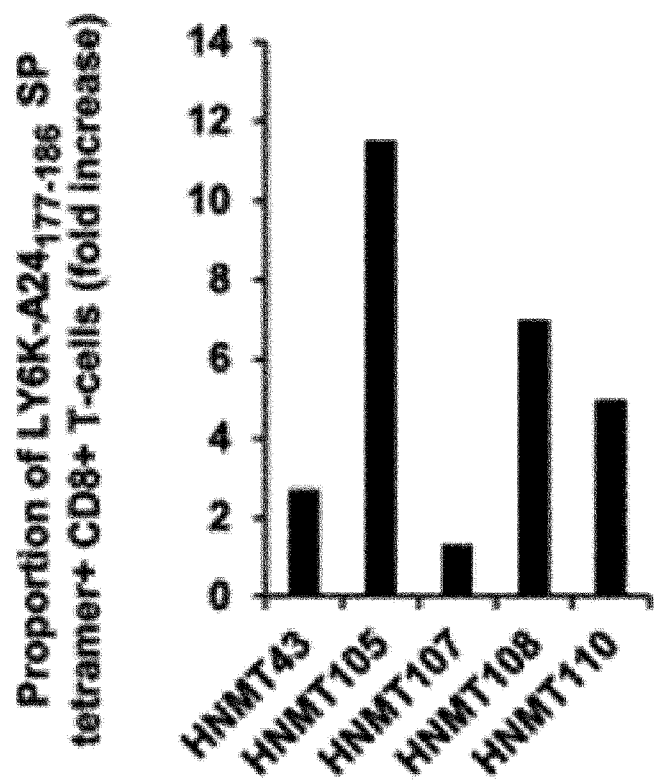
Figure 10E:
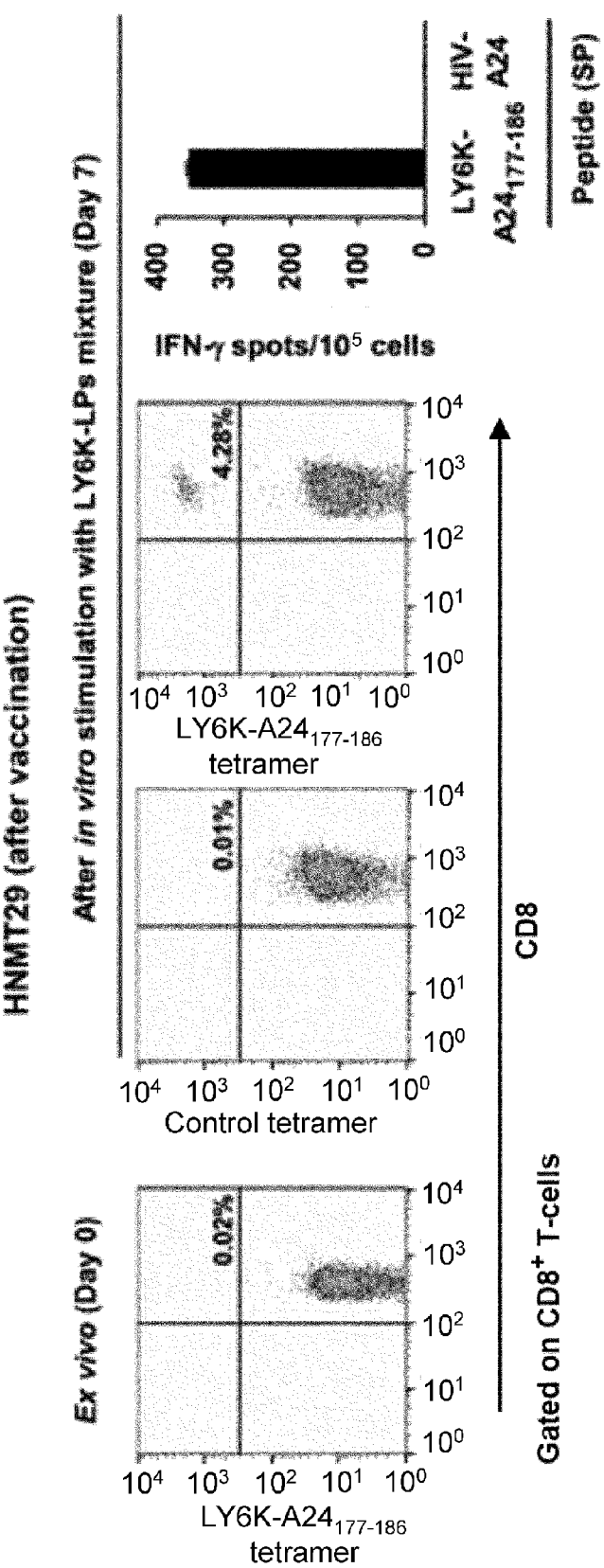
Figure 10F:
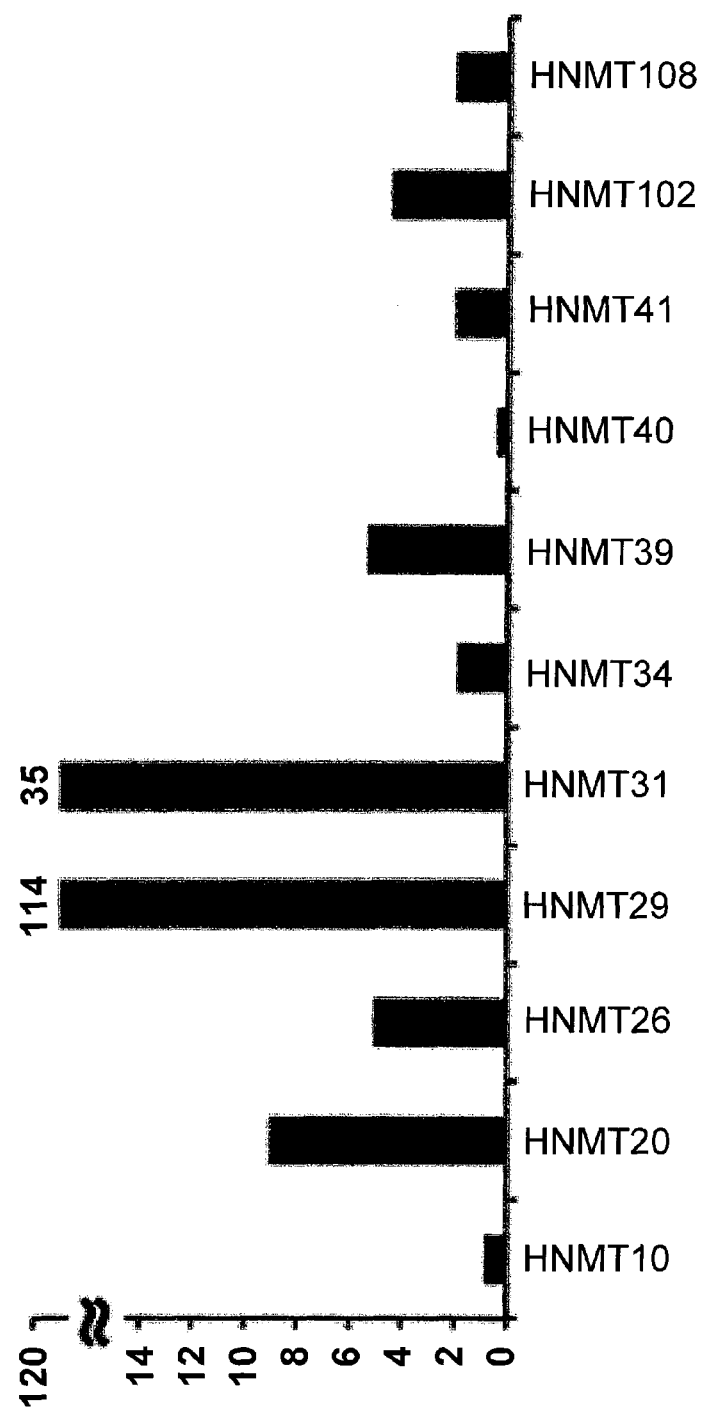

LY6K (172-191) LP Induce Efficient Expansion of LY6K-A24 (177-186) SP Specific CTLs in HNMT Patients The present inventors assessed whether LY6K (172-191) LP could induce in vitro expansion of LY6K-A24 (177-186) SP-specific CTLs in the PBMCs of 6 HNMT patients. Fresh PBMCs from 5 HNMT patients vaccinated with LY6K (177-186) SP were cultured with LY6K (172-191) LP (10 micro-g/mL). The rhIL-2 (20 IU/mL) and rhIL-7 (5 ng/mL) were added on day 0 and day 2. On day 0 (ex vivo) and day 7, the PBMCs were stained with a LY6K-A24 (177-186) SP-specific tetramer. As shown FIG. 10C, when PBMCs isolated from HNMT108 were stained with a LY6K-A24 (177-186) SP-specific tetramer before in vitro culture (ex vivo), the frequency of tetramer$^+$ cells was only 0.05% of CD8$^+$ T-cells. The tetramer$^+$ cells were significantly expanded by 1-week in vitro stimulation of PBMCs with LY6K (172-191) LP without adding LY6K-A24 (177-186) SP. The frequency of LY6K-A24 (177-186)-specific CTLs increased significantly to 0.35% of CD8$^+$ T-cells. Antigen-specific IFN-gamma production was also detected when the cells were stimulated with LY6K-A24 (177-186) SP on day 7. The increase of proportion of tetramer$^+$ CD8$^+$ cells more than 2 times was observed in 4 of 5 HNMT patients after vaccination (FIG. 10D; HNMT43, 105, 108, and 110). These results suggest that expansion of LY6K-A24 (177-186) SP-specific CTLs of HNMT patients might be induced by cross-presentation of LY6K (172-191) LP by DCs. Similar results were obtained from 9 of 11 HNMT patients after vaccination when the PBMCs were cultured with a mixture of LY6K (119-142) LP and LY6K (172-191) LP (10 micro-g/mL each; FIG. 10E-F). Interestingly, LY6K-A24 (177-186) SP-specific tetramer$^+$ cells in HNMT42 before vaccination with LY6K-A24 (177-186) SP were also significantly expanded by stimulation with a mixture of LY6K (119-142) LP and LY6K (172-191) LP (FIG. 10G).

Cross-Presentation of LY6K (172-191) LP Efficiently Primes LY6K-Specific CD8$^+$ T-Cells In Vitro and In Vivo Subsequently, the capacity of LY6K (172-191) LP to induce LY6K-A24 (177-186) SP-specific CTLs was examined by tetramer labeling. HLA-A24-restricted LY6K-A24 (177-186) SP-specific CTLs were significantly induced in PBMCs cultured with LY6K (172-191) LP for 2 weeks in 3 HLA-A24$^+$ healthy donors (HDL1, HDL3, HDL4; FIG. 10H and data not shown).

Figure 10I:
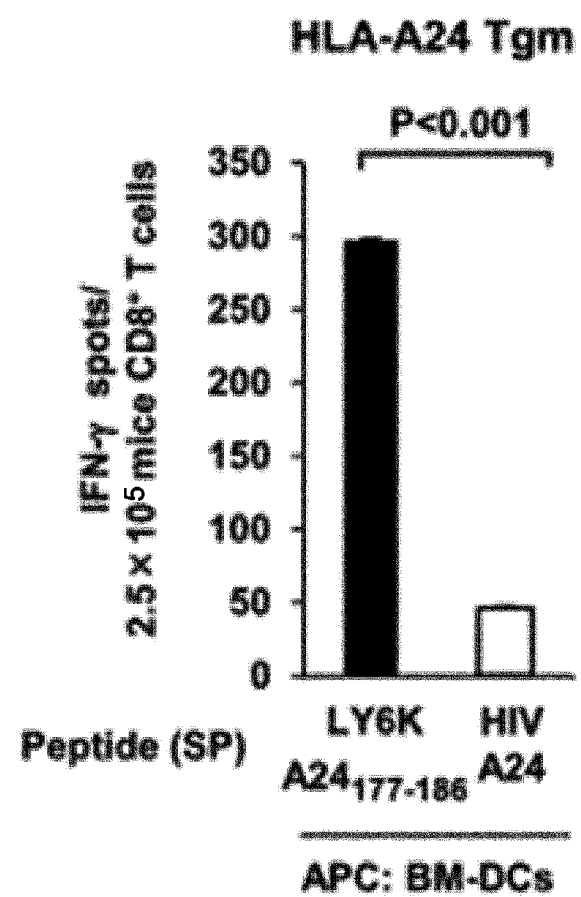

The capacity of LY6K (172-191) LP to prime LY6K-A24 (177-186) SP-specific CTLs was examined by an ex vivo IFN-gamma ELISPOT assay. HLA-A24 Tgm were immunized 3 times with LY6K (172-191) LP. The CD8$^+$ T-cells of HLA-A24 Tgm vaccinated with LY6K (172-191) LP produced IFN-gamma in response to stimulation with BM-DCs pulsed with the LY6K-A24 (177-186) SP (FIG. 10I). These results demonstrate that after uptake of LY6K (172-191) LP, APCs can cross-prime LY6K-A24 (177-186) SP-specific CTLs in vitro and in vivo.

Enhanced Induction of LY6K-A24 (177-186)-Specific CTLs by LY6K-LP-Specific Th Cells The inventors tested whether LY6K-LPs could enhance induction of LY6K-A24 (177-186) SP-specific CTLs. LY6K-LP-specific bulk CD4$^+$ T-cells and LY6K-A24 (177-186) SP-specific bulk CD8$^+$ T-cells derived from HDL3 were cultured with autologous DCs in the presence of LY6K-A24 (177-186) SP, LY6K-A24 (177-186) SP+control LP, or LY6K-A24 (177-186) SP+LY6K-LP. After 1-week in vitro culture with peptides, the cultured cells were stained with LY6K-A24 (177-186) SP-specific tetramer. As shown FIG. 11A, the addition of LY6K-A24 (177-186) SP+LY6K (119-142) LP or LY6K-A24 (177-186) SP+LY6K (172-191) LP significantly increased the absolute number of LY6K-A24 (177-186) SP-specific CD8$^+$ T cells compared with the addition of LY6K-A24 (177-186) SP alone or LY6K-A24 (177-186) SP+control LP. The enhanced induction of LY6K-

A24 (177-186) SP-specific tetramer+ T-cell in HLA-A24+ HDL4 by the activated LY6K (172-191) LP-specific Th cells was observed (data not shown).

Figure 11B:
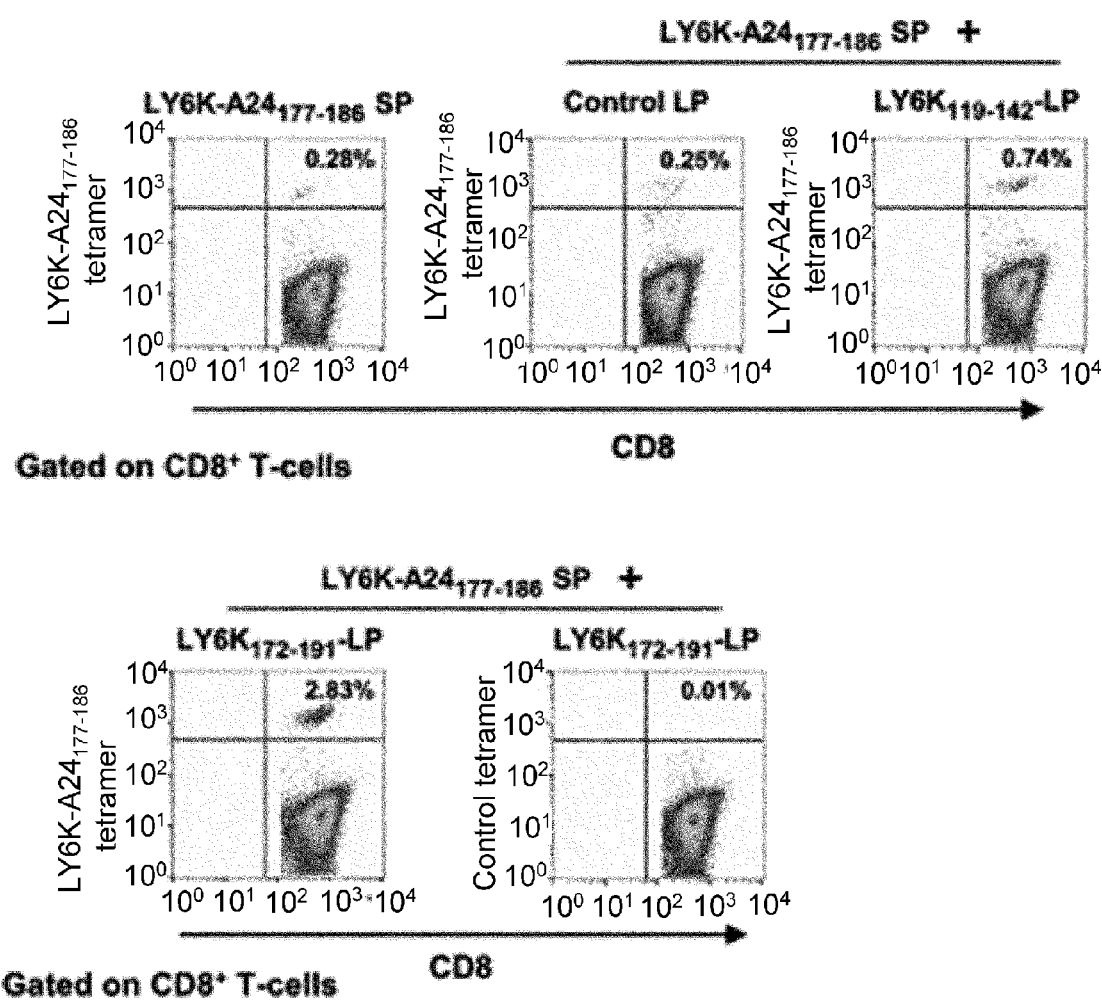
Figure 11C:
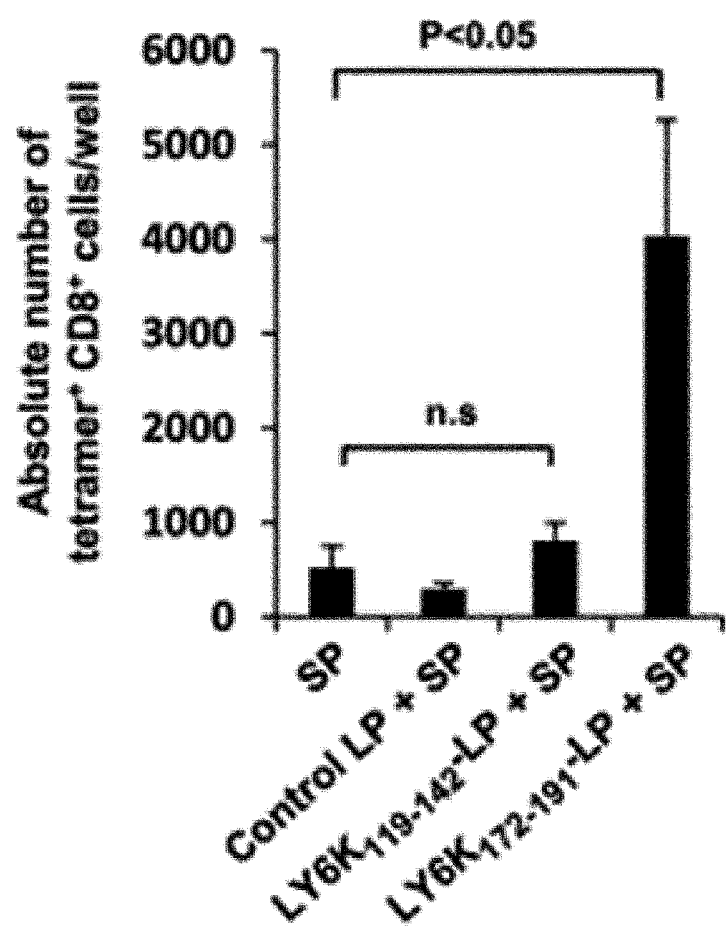

Next, the synergistic effect of LY6K-LP on induction of LY6K-A24 (177-186) SP-specific CTLs in PBMCs from HNMT patients after vaccination (HNMT31, 42, and 43) was assessed. PBMCs collected from HNMT43 at 2 months after immunization were cultured for 7 days with LY6K-A24 (177-186) SP alone, LY6K-A24 (177-186) SP+control LP, LY6K-A24 (177-186) SP+LY6K (119-142) LP, or LY6K-A24 (177-186) SP+LY6K (172-191) LP. After 1-week in vitro culture with peptides, the cells were stained with LY6K-A24 (177-186) SP-specific tetramer (FIG. 11B). When the PBMCs were cultured with LY6K-A24 (177-186) SP+LY6K (172-191) LP, the absolute number of LY6K-A24 (177-186) SP-specific CD8+ T-cells was significantly expanded in comparison with when cultured with LY6K-A24 (177-186) SP alone or LY6K-A24 (177-186) SP+control LP (FIG. 11C). There was no synergistic effect of LY6K (119-142) LP on induction of LY6K-A24 (177-186) SP-specific CTLs in HNMT43. Similar results were obtained when the inventors assessed at 1 month after immunization (data not shown). Similar results in HNMT31 and HNMT 42 by adding LY6K (119-142) LP or LY6K (172-191) LP to LY6K-A24 (177-186) SP were obtained (FIG. 11D). These results suggest that LY6K-LPs could produce synergistic induction of LY6K-A24 (177-186) SP-specific CTLs.

Discussion

It is considered that the most attractive vaccine compounds are synthetic LPs corresponding to the sequence of TAAs that can induce therapeutic immune responses of CD4+ T cells and CD8+ T cells (Kenter G G, et al. N Engl J Med 2009; 361: 1838-47. Melief C J and van der Burg S H. Nat Rev Cancer 2008; 8: 351-60.). Following the injection of these LPs, the patient's DCs will take up the LPs, process them and present all possible CTL-epitopes and Th-epitopes in the context of various HLA class I and HLA class II molecules, respectively. Thus, the present inventors considered that an ideal peptide vaccine for cancer immunotherapy should be a single polypeptide that can induce both CTL and Th1 cell restricted by the most commonly found HLA. In this study, the present inventors identified a LY6K-derived LP including CTL-epitope and found that this LY6K-derived LP can be recognized by promiscuous HLA-class II-restricted Th1 cells. Moreover the inventors observed that the T cell responses against two LY6K-derived LP were found in advanced head and neck cancer patients actively vaccinated with LY6K-derived CTL-epitope peptide. These results suggest that the tumor lysis induced by CTL activated with vaccination accelerate uptake by antigen presenting cell and processing of LY6K protein to present LY6K-derived LPs to CD4+ T cells, and that the synergy between LY6K-specific CTL-responses and Th-responses occurred in vivo.

In conclusion, the inventors first identified two LY6K-derived peptides recognized by promiscuous HLA-class II-restricted CD4+ Th cells, and one of them included a CTL-epitope, suggesting that these Th1-epitopes provide a good tool for propagation of not only LY6K-specific Th1 cell but also LY6K-specific CTLs by possible cross-presentation. These findings would promote a clinical trial of LY6K-peptide-based immunotherapy for various types of cancers in the future.

INDUSTRIAL APPLICABILITY

The present invention describes Th1 cell epitope peptides derived from LY6K that can induce potent anti-tumor immune responses and thus have applicability to a wide array of cancer types. Such peptides warrant further development as peptide vaccines against cancer, especially against cancers expressing LY6K. The peptides of the present invention can induce Th1 cell response and thus cytokines secreted by Th1 cells can help or activate any immune cells responsible for cellular immunity in an antigen independent manner. Therefore, immunotherapeutic strategy provided by the present invention can be applied to any diseases including cancers, as long as the disease can be improved via immune responses mediated by MHC class II molecules. In particular, Th1 cells of the present invention can improve immunological responses raised by CTLs. Therefore, the peptide of the present invention would be beneficial to enhance CTL response against diseases including cancers in a subject.

Moreover, in preferred embodiments, the peptides of the present invention can also induce CTLs against LY6K expressing cells, as well as Th1 cells. Such peptide of the present invention can be also useful for the treatment of diseases associated with LY6K, e.g. cancers, more particularly, bladder cancer, cervical cancer, cholangiocellular carcinoma, esophageal cancer, gastric cancer, non-small cell lung cancer (NSCLC), osteosarcoma, pancreatic cancer, soft tissue tumor, and head-and-neck malignant tumor.

While the present invention is herein described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention, the metes and bounds of which are defined by the appended claims.

The invention claimed is:

1. A composition comprising one or more peptide(s) consisting of an amino acid sequence selected from the group consisting of SEQ ID NO: 1, 2 and 6 having ability to induce T helper type 1 (Th1) cells in combination with an adjuvant in an amount effective to enhance an immune response.

2. The composition of claim 1, wherein said composition further comprises one or more peptide(s) having CTL inducibility.

3. A method for inducing an APC having an ability to induce a Th1 cell, said method comprising a step of contacting an APC with one or more peptide(s) consisting of an amino acid sequence selected from the group consisting of SEQ ID NO: 1, 2 and 6 having ability to induce T helper type 1 (Th1) cells in vitro, ex vivo or in vivo.

4. A method for inducing an APC having an ability to induce a CTL, said method comprising a step selected from the group consisting of:
   (a) contacting an APC with one or more peptide(s) consisting of an amino acid sequence selected from the group consisting of SEQ ID NO: 1, 2 and 6 having ability to induce T helper type 1 (Th1) cells in vitro, ex vivo or in vivo; and
   (b) introducing a polynucleotide encoding the peptide of (a) into an APC.

5. A method for inducing a Th1 cell, said method comprising a step selected from the group consisting of:
   (a) co-culturing a CD4-positive T cell with an APC that presents on its surface a complex of an MHC class II molecule and one or more peptide(s) consisting of an amino acid sequence selected from the group consisting of SEQ ID NO: 1, 2 and 6 having ability to induce T helper type 1 (Th1) cells; and (b) introducing a polynucleotide encoding both of T cell receptor (TCR) subunits, or polynucleotides encoding each of TCR subunits into a CD4-positive T cell, wherein the TCR can bind to a complex of an WIC class II molecule and the peptide of (a) presented on cell surface.

6. A method for inducing a CTL, said method comprising the step selected from the group consisting of:
  (a) co-culturing both of a CD4-positive T cell and a CD8-positive T cell with APCs contacted with one or more peptide(s) consisting of an amino acid sequence selected from the group consisting of SEQ ID NO: 1, 2 and 6 having ability to induce T helper type 1 (Th1) cells; and
  (b) co-culturing a CD8-positive T cell with an APC contacted with one or more peptide(s) consisting of an amino acid sequence selected from the group consisting of SEQ ID NO: 1, 2 and 6 having ability to induce T helper type 1 (Th1) cells.

7. A method for enhancing an immune response mediated by an WIC class II molecule, wherein the method comprises a step of administering to a subject one or more peptide(s) consisting of an amino acid sequence selected from the group consisting of SEQ ID NO: 1, 2 and 6 having ability to induce T helper type 1 (Th1) cells.

8. A method of inducing an immune response against cancer in a subject in need thereof, said method comprising the step of administering to the subject a composition comprising one or more peptide(s) consisting of an amino acid sequence selected from the group consisting of SEQ ID NO: 1, 2 and 6 having ability to induce T helper type 1 (Th1) cells.

\* \* \* \* \*

UNITED STATES PATENT AND TRADEMARK OFFICE
CERTIFICATE OF CORRECTION

PATENT NO.        : 9,644,010 B2
APPLICATION NO.   : 14/413416
DATED             : May 9, 2017
INVENTOR(S)       : Yasuharu Nishimura, Yusuke Tomita and Ryuji Osawa It is certified that error appears in the above-identified patent and that said Letters Patent is hereby corrected as shown below:

In the Claims

Claim 5 should read:
5. A method for inducing a Th1 cell, said method comprising a step selected from
the group consisting of:
(a) co-culturing a CD4-positive T cell with an APC that presents on its surface a complex of
an MHC class II molecule and one or more peptide(s) consisting of an amino acid sequence
selected from the group consisting of SEQ ID NO: 1, 2 and 6 having ability to induce T
helper type 1 (Th1) cells; and
(b) introducing a polynucleotide encoding both of T cell receptor (TCR) subunits, or
polynucleotides encoding each of TCR subunits into a CD4-positive T cell, wherein the TCR
can bind to a complex of an MHC class II molecule and the peptide of (a) presented on
cell surface.

Claim 7 should read:
7. A method for enhancing an immune response mediated by an MHC class II
molecule, wherein the method comprises a step of administering to a subject one or more
peptide(s) consisting of an amino acid sequence selected from the group consisting of SEQ
ID NO: 1, 2 and 6 having ability to induce T helper type 1 (Th1) cells.

Signed and Sealed this
Second Day of January, 2018

Joseph Matal
*Performing the Functions and Duties of the
Under Secretary of Commerce for Intellectual Property and
Director of the United States Patent and Trademark Office*